(12) United States Patent
Deng et al.

(10) Patent No.: US 7,868,001 B2
(45) Date of Patent: Jan. 11, 2011

(54) CYTOKINE INHIBITORS

(75) Inventors: Wei Deng, Shanghai (CN); Wei-Guo Su, Shanghai (CN); Yu Cai, Shanghai (CN); Jeff Duan, Shanghai (CN)

(73) Assignee: Hutchison Medipharma Enterprises Limited (BS)

( * ) Notice: Subject to any disclaimer, the term of this patent is extended or adjusted under 35 U.S.C. 154(b) by 249 days.

(21) Appl. No.: 11/934,154

(22) Filed: Nov. 2, 2007

(65) Prior Publication Data

US 2009/0118292 A1    May 7, 2009

(51) Int. Cl.
- *C07D 487/04* (2006.01)
- *C07D 413/12* (2006.01)
- *A61K 31/4985* (2006.01)
- *A61K 31/5355* (2006.01)
- *A61P 35/00* (2006.01)
- *C07D 513/04* (2006.01)

(52) U.S. Cl. .............. 514/233.2; 514/248; 544/236; 544/117; 546/121; 548/154

(58) Field of Classification Search ............. 544/117, 544/236; 514/233.2, 248
See application file for complete search history.

(56) References Cited

U.S. PATENT DOCUMENTS

| | | | |
|---|---|---|---|
| 4,716,169 | A | 12/1987 | Heider et al. |
| 7,144,872 | B2 | 12/2006 | Zablocki et al. |
| 2004/0127521 | A1 | 7/2004 | Cai et al. |
| 2006/0084650 | A1 | 4/2006 | Dong et al. |
| 2007/0049620 | A1 | 3/2007 | Kimura et al. |
| 2009/0005399 | A1 * | 1/2009 | Kuehnert et al. ......... 514/256 |
| 2009/0156604 | A1 * | 6/2009 | Holder et al. ............ 514/243 |
| 2009/0186902 | A1 * | 7/2009 | Merla et al. ............ 514/253.04 |

FOREIGN PATENT DOCUMENTS

| | | |
|---|---|---|
| EP | 0185345 | 12/1985 |
| EP | 0185346 | 12/1985 |
| WO | WO 89/01478 * | 2/1989 |
| WO | WO 2005/066177 | 7/2005 |
| WO | WO 2007/034278 | 3/2007 |
| WO | WO2007/034278 | 3/2007 |
| WO | WO 2007/056210 * | 5/2007 |
| WO | WO 2007/149395 | 12/2007 |
| WO | WO 2008/104279 | 9/2008 |
| WO | WO 2008/156721 * | 12/2008 |
| WO | WO 2009/016286 * | 2/2009 |
| WO | WO 2009/037394 * | 3/2009 |
| WO | WO 2009/140128 | 11/2009 |

OTHER PUBLICATIONS

English language Abstract of EP 0185346, Dec. 16, 1985.

* cited by examiner

*Primary Examiner*—James O Wilson
*Assistant Examiner*—Cecilia M Jaisle
(74) *Attorney, Agent, or Firm*—Finnegan, Henderson, Farabow, Garrett & Dunner, L.L.P.

(57) ABSTRACT

A compound of Formula I:

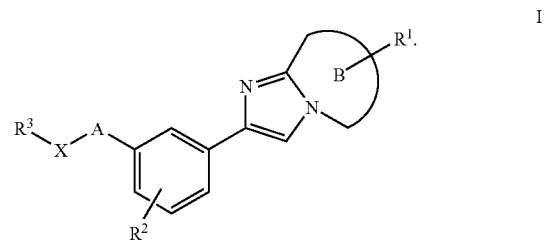

Each variable is defined in the specification. This invention relates to a method of decreasing a level of a cytokine (e.g., TNFα or interlukine such as IL-1β) in a subject with a compound of Formula I. It also relates to a method of treating a disorder mediated by an overproduction of a cytokine with such a compound.

16 Claims, No Drawings

CYTOKINE INHIBITORS

BACKGROUND

Tumor necrosis factor alpha (TNFα), a mononuclear cytokine, is predominately produced by monocytes and macrophages. It possesses various biological activities: (1) killing cancer cells or inhibiting growth of cancer cells, (2) enhancing the phagocytosis of neutrophilic granulocytes, (3) up-regulating the production of peroxide, and (4) killing infection pathogens.

Interleukin-1 beta (IL-1β), a cytokine secreted by cells such as monocyte macrophages and dendritic cells, mediates immune and inflammatory responses.

Nuclear factor-kappa B (NF-κB) is a pro-inflammatory transcription factor. It upregulates cytokines, including TNFα and IL-1β, and thereby mediates the inflammatory response.

Inducible nitric oxide synthase (iNOS) is induced by endotoxins or cytokines (e.g., TNFα). It catalyzes the production of nitric oxide, an important pleiotropic molecule, from L-aginine and oxygen.

TNFα, IL-1β, NF-κB, and iNOS play important roles in many key physiological and pathological processes relating to a wide range of diseases, e.g., autoimmune diseases, cancer, atherosclerosis, and diabetes. Therefore, modulating the expression or activity of TNFα, IL-1β, NF-κB, or iNOS can lead to treatment of these diseases. See, e.g., Ogata H, Hibi T. et al *Curr Pharm Des.* 2003; 9(14): 1107-13; Taylor P C. et al *Curr Pharm Des.* 2003; 9(14): 1095-106; Fan C., et al. *J. Mol. Med* 1999,. 77, 577-592; and Alcaraz et al., *Current Pharmaceutical Design*, 2002: 8, 215.

SUMMARY

This invention is based on surprising discoveries that imidazole compounds significantly inhibited production of cytokines, including TNFα and interleukin (e.g., IL-1β, IL-2, or IL-6) in mice and rats. These compounds are potentially useful in treating disorders mediated by abnormal levels of cytokines, such as inflammation, autoimmune diseases, diabetes, atherosclerosis and cancer.

Accordingly, one aspect of this invention features imidazole compounds of Formula I:

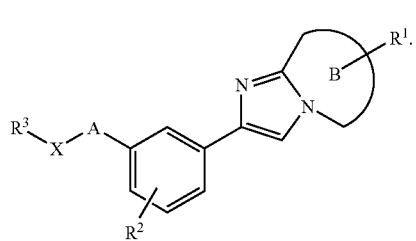

In this formula, A is deleted, $(CR'R'')_n$, in which n is 1, 2, 3, 4, or 5, or a heteroaryl selected from the group consisting of

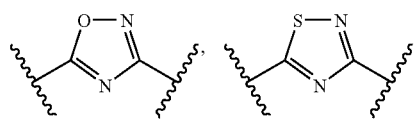

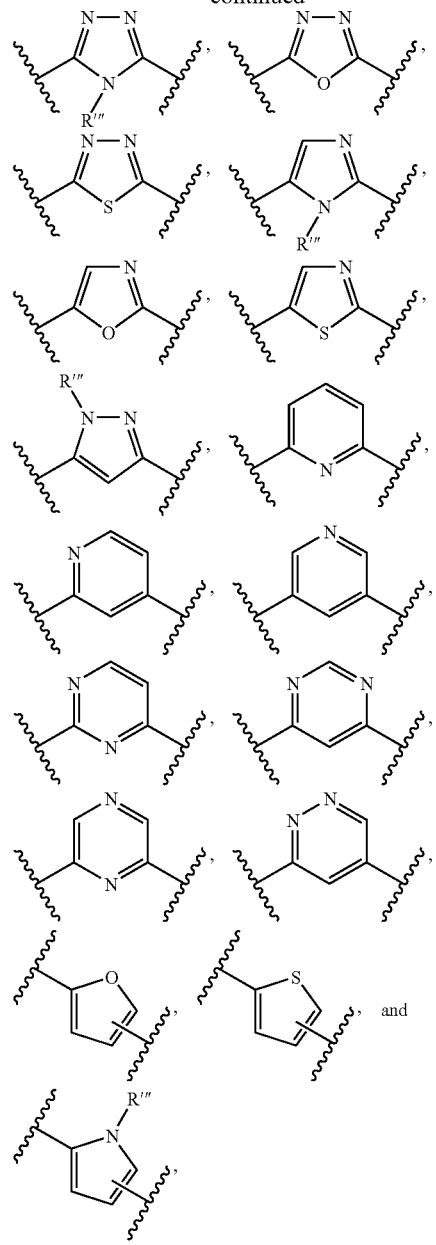

in which each of R' and R''', independently, is H or $C_{1-10}$ alkyl, and R is H or $C_{1-10}$ alkyl, in which $C_{1-10}$ alkyl is optionally substituted by halo, $C(O)R^a$, $OR^b$, $SR^b$, $S(O)_2R^b$, $NR^cR^d$, $C(O)NR^cNR^d$, in which each of $R^a$ and $R^b$, independently, is H, $C_{1-10}$ alkyl, $C_{1-10}$ haloalkyl, aryl, or heteroaryl, and each of $R^c$ and $R^d$, independently, is H, $C_{1-10}$ alkyl, $C_{1-10}$ haloalkyl, aryl, heteroaryl, or $R^c$ and $R^d$ together with the N atom to which they are attached form a 4-, 5-, 6- or 7-membered heterocycloalkyl group; B is a 5-6 membered heteroaryl; X is deleted, $(CR^{a_1}R^{b_1})_m$ in which m is 1, 2, 3, 4, or 5, SO, $SO_2$, CO, COO, $CONR^{c_1}$, $NR^{c_1}$, or $NR^{c_1}CONR^{d_1}$, in which each of $R^{a_1}$, $R^{b_1}$, $R^{c_1}$, and $R^{d_1}$, independently, is H or $C_{1-10}$ alkyl; each of $R^1$ and $R^2$, independently, is H, halo, $NR^{c_1}C(O)R^{a_1}$, $OR^{b_1}$, $NR^{c_1}R^{d_1}$, $NR^{c_1}C(O)OR^{b_1}$, $NR^{c_1}S(O)_2R^{b_1}$, $C_{1-10}$ alkyl, or $C_{1-10}$ haloalkyl, in which each of $R^{a_1}$ and $R^{b_1}$, independently, is H, $C_{1-10}$ alkyl, $C_{1-10}$ haloalkyl, aryl, or heteroaryl, and each of $R^{c1}$ and $R^{d1}$, independently, is H, $C_{1-10}$ alkyl, $C_{1-10}$ haloalkyl, aryl, heteroaryl, or $R^{c1}$ and $R^{d1}$ together with the N atom to which they are attached form a 4-, 5-, 6- or 7-membered heterocycloalkyl group; and $R^3$ is H, halo, $OC(O)R^{a2}$, $C(O)OR^{b2}$, $OR^{b2}$, $SR^{b2}$, $SO_2R^{b2}$, $C(O)NR^{c2}R^{d2}$, $NR^{c2}R^{d2}$, $NR^{c2}C(O)R^{a2}$, $NR^{c2}C(O)C(O)OR^{a2}$, $NR^{c2}S(O)_2R^{b2}$, $C_{1-10}$ alkyl, $C_{1-10}$ haloalkyl, aryl, haloaryl, cycloalkyl, heteroaryl, heterocycloalkyl, arylalkyl, heteroarylalkyl, cycloalkylalkyl or heterocycloalkylalkyl, in which $C_{1-10}$ alkyl, $C_{1-10}$ haloalkyl, aryl, haloaryl, cycloalkyl, heteroaryl, heterocycloalkyl, arylalkyl, heteroarylalkyl, cycloalkylalkyl or heterocycloalkylalkyl is optionally substituted by halo, $C_{1-4}$ alkyl, $C_{1-4}$ haloalkyl, aryl, heteroaryl, CN, $NO_2$, $OR^{b2}$, $C(O)OR^{c2}$, $C(O)NR^{c2}R^2$, or $NR^{c2}R^{d2}$, in which each of $R^{a2}$ and $R^{b2}$, independently, is H, $C_{1-6}$ alkyl, $C_{1-6}$ haloalkyl, aryl, cycloalkyl, heteroaryl, heterocycloalkyl, arylalkyl, or heteroarylalkyl in which $C_{1-6}$ alkyl, $C_{1-6}$ haloalkyl, aryl, cycloalkyl, heteroaryl, heterocycloalkyl, arylalkyl, or heteroarylalkyl is optionally substituted by OH, $C_{1-6}$ alkoxyl, CN, $NO_2$, or halo, and each of $R^{c2}$ and $R^{d2}$, independently, is H, $C_{1-10}$ alkyl, $C_{1-10}$ haloalkyl, aryl, heteroaryl, cycloalkyl, heterocycloalkyl, arylalkyl, heteroarylalkyl, cycloalkylalkyl or heterocycloalkylalkyl, in which $C_{1-10}$ alkyl, $C_{1-10}$ haloalkyl, aryl, heteroaryl, cycloalkyl, heterocycloalkyl, arylalkyl, heteroarylalkyl, cycloalkylalkyl or heterocycloalkylalkyl is optionally substituted by $C_{1-6}$ alkoxyl, OH, amino, $C_{1-4}$ alkylamino, $C_{2-8}$ dialkylamino, $S(O)_2R^{b2}$, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl, or $R^{c2}$ and $R^{d2}$ together with the N atom to which they are attached form a 4-, 5-, 6- or 7-membered heterocycloalkyl group.

Referring to Formula I, a subset of the indazole compounds described above are those in which each A is deleted, $CH_2$, or

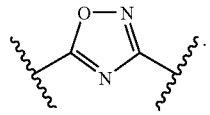

In these compounds, B can be

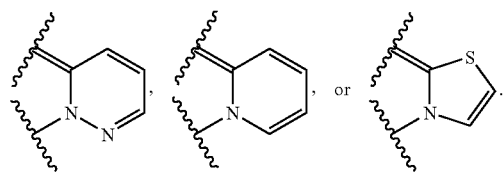

X can be deleted, $(CR^aR^{b1})_m$, CO, COO, $NR^{c1}$, $CONR^{c1}$, or $NR^{c1}CONR^{d1}$. More specifically, X can be $CH_2$, NH, CO, COO, CONH, or NHCONH.

The term "alkyl" herein refers to a straight or branched hydrocarbon, containing e.g. 1-20 carbon atoms. Examples of alkyl groups include, but are not limited to, methyl, ethyl, n-propyl, i-propyl, n-butyl, i-butyl, and t-butyl. The term "alkoxyl" refers to an —O— alkyl. The term "haloakyl" refers to an alkyl group having one or more halogen substituents. Example haloalkyl groups include $CF_3$, $C_2F_5$, $CHF_2$, $CCl_3$, $CHCl_2$, $C_2Cl_5$, and the like. The term "arylalkyl" (or "heteroarylakyl") refers to alkyl substituted by aryl (or heteroaryl) and "cycloalkylalkyl" (or "heterocycloalkylalkyl") refers to alkyl substituted by cycloalkyl (or heterocycloalkyl). An example arylalkyl group is benzyl. The term "cycloalkyl" refers to a saturated, cyclic hydrocarbon moiety, such as cyclohexyl. The term "heterocycloalkyl" refers to a saturated, cyclic moiety having at least one ring heteroatom (e.g., N, O, or S), such as 4-tetrahydropyranyl. The term "aryl" refers to a hydrocarbon moiety having one or more aromatic rings. Examples of aryl moieties include phenyl (Ph), phenylene, naphthyl, naphthylene, pyrenyl, anthryl, and phenanthryl. The term "haloaryl" refers to an aryl group having one or more halogen substituents. The term "heteroaryl" refers to a moiety having one or more aromatic rings that contain at least one heteroatom (e.g., N, O, or S). Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl. The term "halo" or "halogen" includes fluoro, chloro, bromo, and iodo. The term "alkylamino" refers to an amino group substituted by an alkyl group. The term "dialkylamino" refers to an amino group substituted by two alkyl groups.

Alkyl, haloalkyl, alkoxyl, arylalkyl, heteroarylalkyl, cycloalkylakyl, heterocycloalkylalkyl, cycloalkyl, heterocycloalkyl, aryl, and heteroaryl mentioned herein include both substituted and unsubstituted moieties, unless specified otherwise. Possible substituents on cycloalkyl, cycloalkenyl, heterocycloalkyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amido, amidino, guanidine, ureido, thioureido, cyano, nitro, nitroso, azido, acyl, thioacyl, acyloxy, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

Another aspect of this invention relates to a method of decreasing a level of a cytokine (e.g., TNFα or interlukine) by contacting the cytokine (e.g., TNFα or interlukine) with an effective amount of one or more of the imidazole compounds of Formula I. The interlukine include but is not limited to IL-1β, IL-2, and IL-6.

Still another aspect of this invention relates to a method of treating a disorder mediated by an overproduction of a cytokine (e.g., TNFα or interlukine), such as, inflammatory bowel disease (including Crohn's disease and ulcerative colitis), chronic heart failure, diabetes mellitus, systemic lupus erythematosus, polymyositis/dermatomyositis, psoriasis, acute myelogenous leukemia, AIDS dementia complex, hematosepsis, septic shock, graft-versus-host disease, uveitis, asthma, acute pancreatitis, allergy, atherosclerosis, multiple sclerosis, or periodontal disease. The method includes administering to a subject in need of the treatment an effective amount of one or more of the imidazole compounds of Formula I.

The compounds of Formula I as described above include the compounds themselves, as well as their salts, prodrugs, and solvates, if applicable. A salt, for example, can be formed between an anion and a positively charged group (e.g., ammonium) on a compound of Formula I. Suitable anions include chloride, bromide, iodide, sulfate, nitrate, phosphate, citrate, methanesulfonate, trifluoroacetate, acetate, malate, tosylate, tartrate, fumarate, glutamate, glucuronate, lactate, glutarate, and maleate. Likewise, a salt can also be formed between a cation and a negatively charged group (e.g., carboxylate) on a compound of Formula I. Suitable cations include sodium ion, potassium ion, magnesium ion, calcium ion, and an ammonium cation such as tetramethylammonium ion. The compounds also include those salts containing quaternary nitrogen atoms. Examples of prodrugs include esters and other pharmaceutically acceptable derivatives, which, upon administration to a subject, are capable of providing active compounds of Formula I. A solvate refers to a complex formed between an active compound of Formula I and a pharmaceutically acceptable solvent. Examples of pharmaceutically acceptable solvents include water, ethanol, isopropanol, ethyl acetate, acetic acid, and ethanolamine.

In a further aspect, this invention features a chemical process for preparing the aforementioned compounds (including their salts and solvates) and/or their intermediates.

In one implementation, the process includes coupling a compound of the following formula:

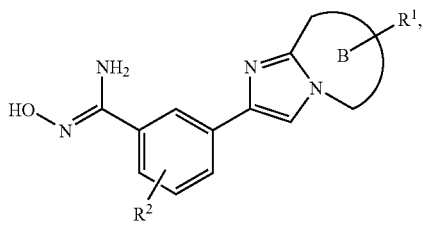

in which B is a 5-6 membered heteroaryl, and each of $R^1$ and $R^2$, independently, is H, halo, $NR^{c1}C(O)R^{a1}$, $OR^{b1}$, $NR^{c1}R^{d1}$, $NR^{c1}C(O)OR^{b1}$, $NR^{c1}S(O)_2R^{b1}$, $C_{1-10}$ alkyl, or $C_{1-10}$ haloalkyl, in which each of $R^{a1}$ and $R^{b1}$, independently, is H, $C_{1-10}$ alkyl, $C_{1-10}$ haloalkyl, aryl, or heteroaryl, and each of $R^{c1}$ and $R^{d1}$, independently, is H, $C_{1-10}$ alkyl, $C_{1-10}$ haloalkyl, aryl, heteroaryl, or $R^{c1}$ and $R^{d1}$ together with the N atom to which they are attached form a 4-, 5-, 6- or 7-membered heterocycloalkyl group; with a compound of the following formula:

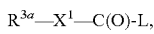

in which L is a leaving group (e.g., chloro, or OC(O)R), $X^1$ is deleted or $(CR^{a'}R^{b'})_m$, in which m is 1, 2, 3, 4, or 5, and each of $R^{a'}$ and $R^{b'}$, independently, is H or $C_{1-10}$ alkyl, and $R^{3a}$ is H, halo, $OC(O)R^{a2}$, $C(O)OR^{b2}$, $C(O)NR^{c2}R^{d2}$, $C_{1-10}$ alkyl, $C_{1-10}$ haloalkyl, aryl, haloaryl, cycloalkyl, heteroaryl, heterocycloalkyl, arylalkyl, heteroarylalkyl, cycloalkylalkyl or heterocycloalkylalkyl, in which $C_{1-10}$ alkyl, $C_{1-10}$ haloalkyl, aryl, haloaryl, cycloalkyl, heteroaryl, heterocycloalkyl, arylalkyl, heteroarylalkyl, cycloalkylalkyl or heterocycloalkylalkyl is optionally substituted by halo, $C_{1-4}$ alkyl, $C_{1-4}$ haloalkyl, aryl, heteroaryl, CN, $NO_2$, $OR^{b2}$, $C(O)OR^{b2}$, $C(O)NR^{c2}R^{d2}$, or $NR^{c2}R^{d2}$, in which each of $R^{a2}$ and $R^{b2}$, independently, is H, $C_{1-6}$ alkyl, $C_{1-6}$ haloalkyl, aryl, cycloalkyl, heteroaryl, heterocycloalkyl, arylalkyl, or heteroarylalkyl in which $C_{1-6}$ alkyl, $C_{1-6}$ haloalkyl, aryl, cycloalkyl, heteroaryl, heterocycloalkyl, arylalkyl, or heteroarylalkyl is optionally substituted by OH, $C_{1-6}$ alkoxyl, CN, $NO_2$, or halo, and each of $R^{c2}$ and $R^{d2}$, independently, is H, $C_{1-10}$ alkyl, $C_{1-10}$ haloalkyl, aryl, heteroaryl, cycloalkyl, heterocycloalkyl, arylalkyl, heteroarylalkyl, cycloalkylalkyl or heterocycloalkylalkyl, in which $C_{1-10}$ alkyl, $C_{1-10}$ haloalkyl, aryl, heteroaryl, cycloalkyl, heterocycloalkyl, arylalkyl, heteroarylalkyl, cycloalkylalkyl or heterocycloalkylalkyl is optionally substituted by $C_{1-6}$ alkoxyl, OH, amino, $C_{1-4}$ alkylamino, $C_{2-8}$ dialkylamino, $S(O)_2R^{b2}$, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl, or $R^{c2}$ and $R^{d2}$ together with the N atom to which they are attached form a 4-, 5-, 6- or 7-membered heterocycloalkyl group.

In another implementation, the process includes coupling a compound of the following formula:

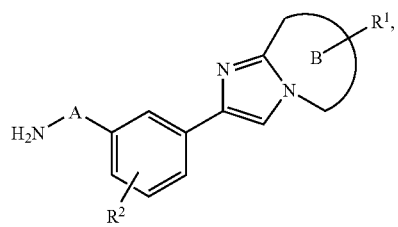

in which A is deleted, $(CR'R'')_n$ in which n is 1, 2, 3, 4, or 5, and each of R' and R'', independently, is H or $C_{1-10}$ alkyl, B, $R^1$, and $R^2$ are defined as above; with a compound of the following formula:

in which L is a leaving group, $X^2$ is deleted, SO, $SO_2$, or CO, and $R^{3b}$ is $NR^{c2}R^{d2}$, $C_{1-10}$ alkyl, $C_{1-10}$ haloalkyl, aryl, haloaryl, cycloalkyl, heteroaryl, heterocycloalkyl, arylalkyl, heteroarylalkyl, cycloalkylalkyl or heterocycloalkylalkyl, in which $C_{1-10}$ alkyl, $C_{1-10}$ haloalkyl, aryl, haloaryl, cycloalkyl, heteroaryl, heterocycloalkyl, arylalkyl, heteroarylalkyl, cycloalkylalkyl or heterocycloalkylalkyl is optionally substituted by halo, $C_{1-4}$ alkyl, $C_{1-4}$ haloalkyl, aryl, heteroaryl, CN, $NO_2$, $OR^{b2}$, $C(O)OR^{b2}$, $C(O)NR^{c2}R^{d2}$, or $NR^{c2}R^{d2}$, in which $R^{c2}$ and $R^{d2}$ are defined above.

In still another implementation, the process includes coupling a compound of the following formula:

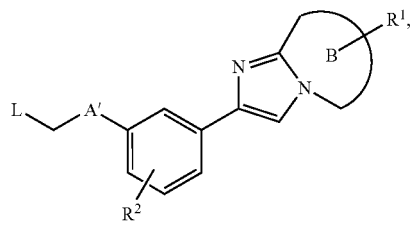

in which L is a leaving group, A' is a heteroaryl selected from the group consisting of

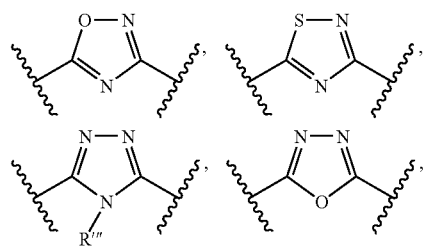

-continued

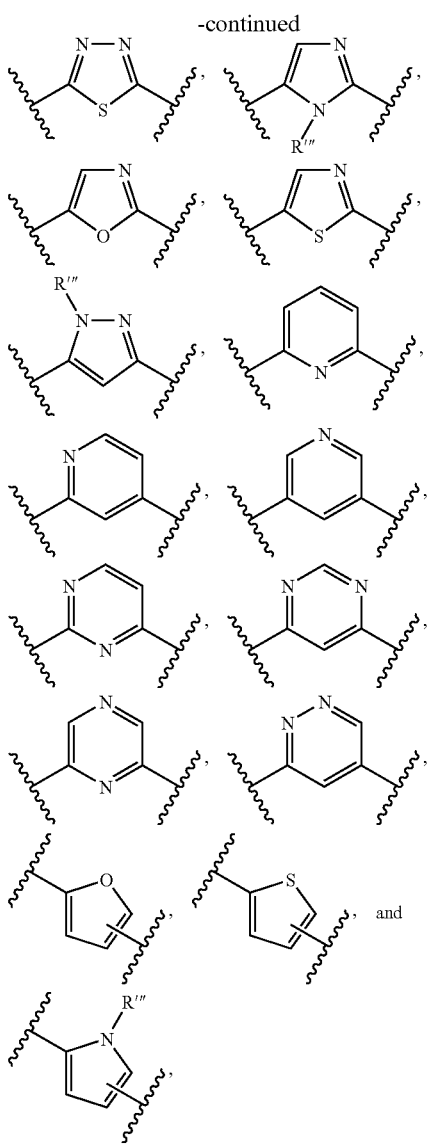

in which each of R' and R", independently, is H or $C_{1-10}$ alkyl, and R''' is H or $C_{1-10}$ alkyl, in which $C_{1-10}$ alkyl is optionally substituted by halo, $C(O)R^a$, $OR^b$, $SR^b$, $S(O)_2R^b$, $NR^cR^d$, $C(O)NR^cNR^d$, in which each of $R^a$ and $R^b$, independently, is H, $C_{1-10}$ alkyl, $C_{1-10}$ haloalkyl, aryl, or heteroaryl, and each of $R^c$ and $R^d$, independently, is H, $C_{1-10}$ alkyl, $C_{1-10}$ haloalkyl, aryl, heteroaryl, or $R^c$ and $R^d$ together with the N atom to which they are attached form a 4-, 5-, 6- or 7-membered heterocycloalkyl group, B, $R^1$, and $R^2$ are defined as above; with a compound of the following formula:

H—$R^{3c}$, wherein $R^{3c}$ is $OC(O)R^{a2}$, $OR^{b2}$, $SR^{b2}$, $SO_2R^{b2}$, $NR^{c2}R^{d2}$, $NR^{c2}C(O)R^{a2}$, $NR^{c2}C(O)C(O)OR^{a2}$, $NR^{c2}S(O)_2R^{b2}$, $C_{1-10}$ alkyl, $C_{1-10}$ haloalkyl, aryl, haloaryl, cycloalkyl, heteroaryl, heterocycloalkyl, arylalkyl, heteroarylalkyl, cycloalkylalkyl or heterocycloalkylalkyl, in which $C_{1-10}$ alkyl, $C_{1-10}$ haloalkyl, aryl, haloaryl, cycloalkyl, heteroaryl, heterocycloalkyl, arylalkyl, heteroarylalkyl, cycloalkylalkyl or heterocycloalkylalkyl is optionally substituted by halo, $C_{1-4}$ alkyl, $C_{1-4}$ haloalkyl, aryl, heteroaryl, CN, $NO_2$, $OR_2$, $C(O)OR^{b2}$, $C(O)NR^{c2}R^{d2}$, or $NR^{c2}R^{d2}$, in which $R^{a2}$, $R^{b2}$, $R^{c2}$, and $R^{d2}$ are defined above.

After each coupling described above, the process can also include forming a pharmaceutically acceptable salt or solvate of the compound of Formula I obtained.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis*, 2d. Ed., Wiley & Sons, 1991, which is incorporated herein by reference in its entirety.

Also within the scope of this invention is a pharmaceutical composition containing one or more of the imidazole compounds of Formula I for use in treating any above-described disorder, as well as this use and use of one or more of the imidazole compounds the for the manufacture of a medicament for the just-mentioned treatment.

The details of one or more embodiments of the invention are set forth in the accompanying description below. Other features, objects, and advantages of the invention will be apparent from the description and the claims.

DETAILED DESCRIPTION

Shown below are exemplary compounds, compounds 1-106, of this invention.

Compound 1

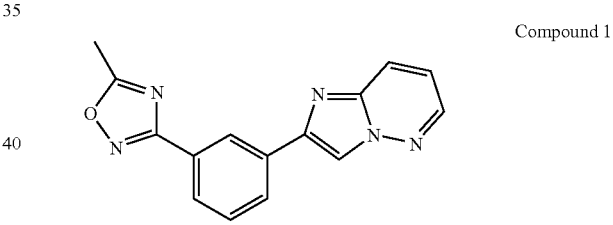

Compound 2

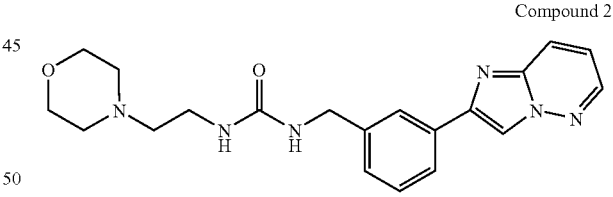

Compound 3

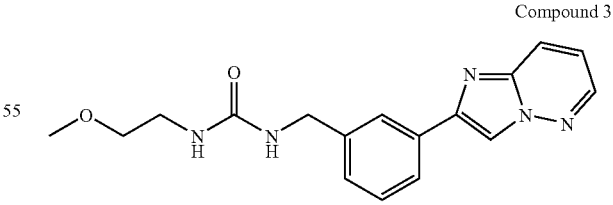

Compound 4

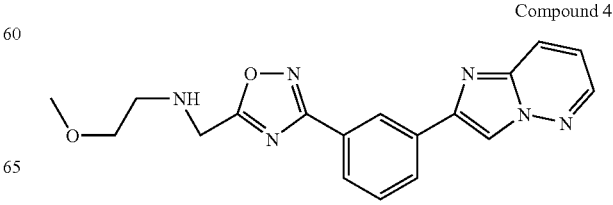

-continued
Compound 5
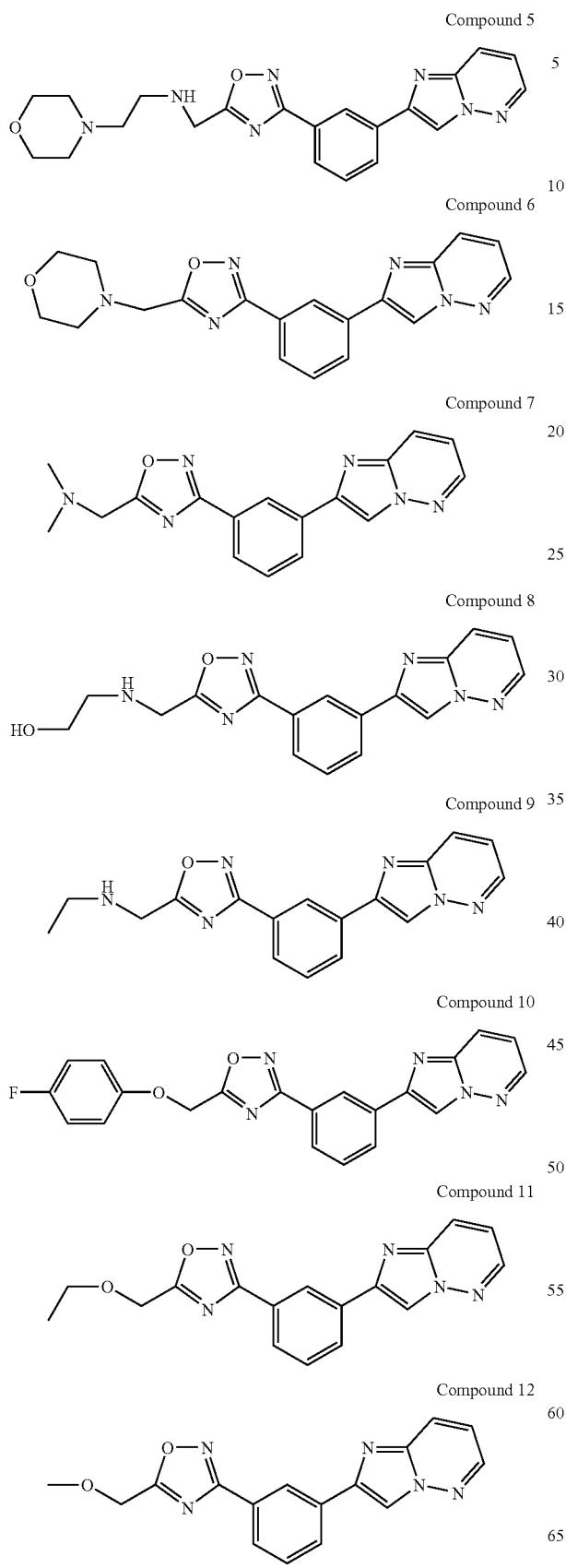
Compound 6
Compound 7
Compound 8
Compound 9
Compound 10
Compound 11
Compound 12
-continued
Compound 13
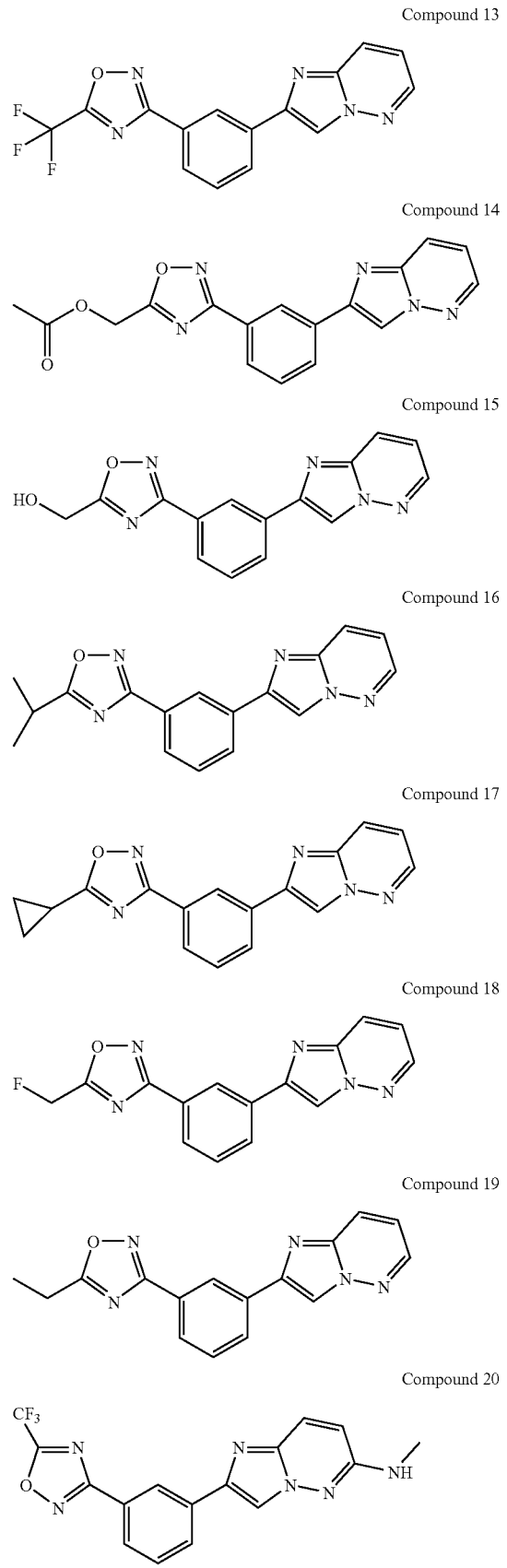
Compound 14
Compound 15
Compound 16
Compound 17
Compound 18
Compound 19
Compound 20

-continued
Compound 21
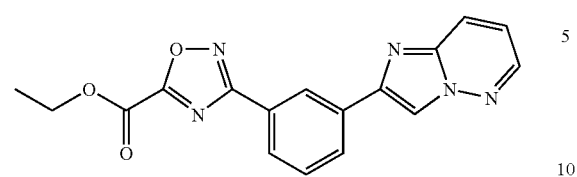
Compound 22
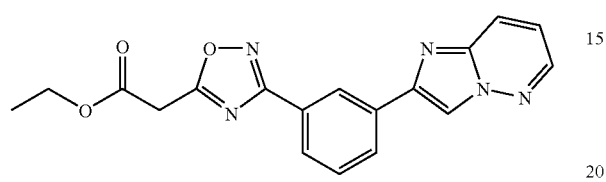
Compound 23
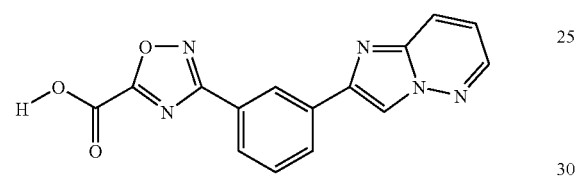
Compound 24
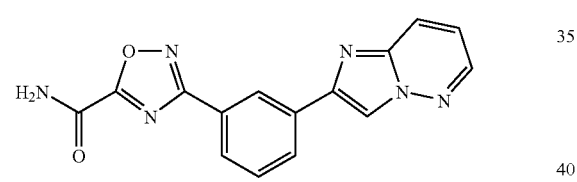
Compound 25
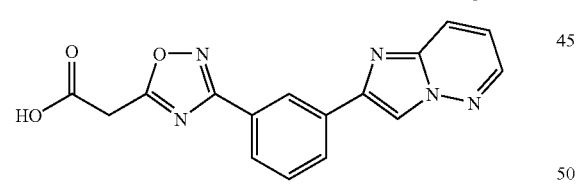
Compound 26
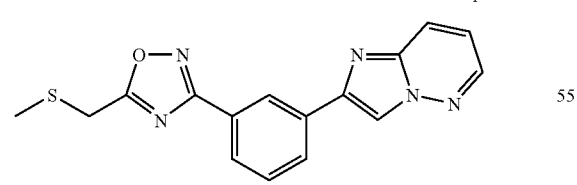
Compound 27
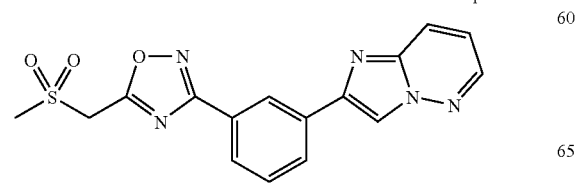
-continued
Compound 28
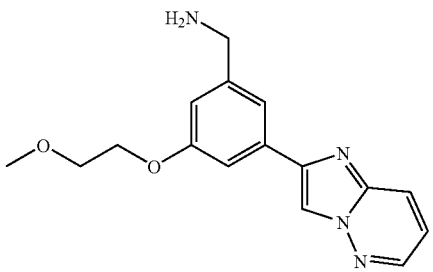
Compound 29
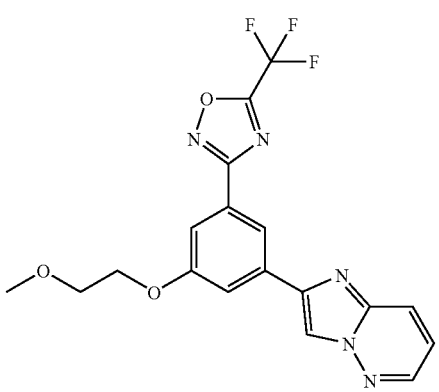
Compound 30
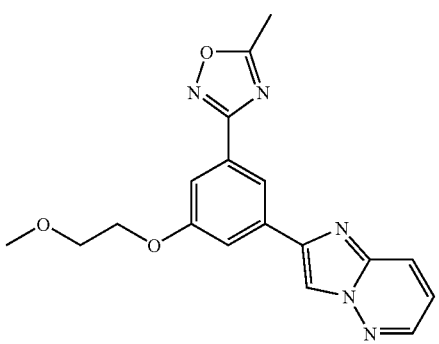
Compound 31
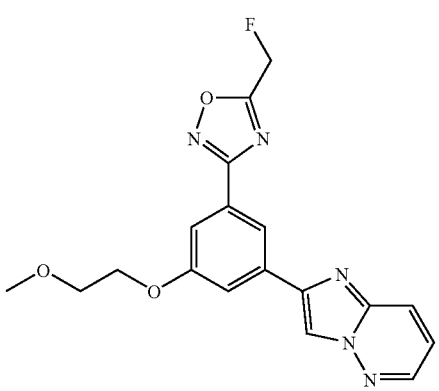

Compound 32
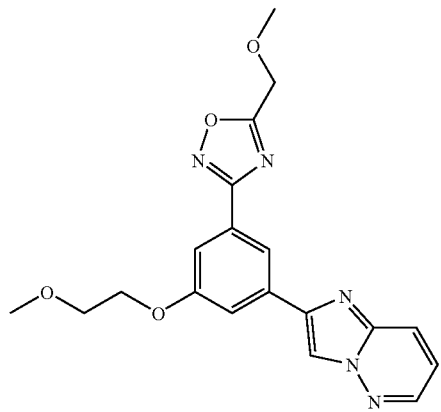
Compound 33
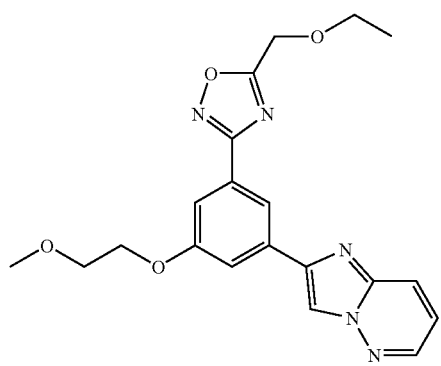
Compound 34
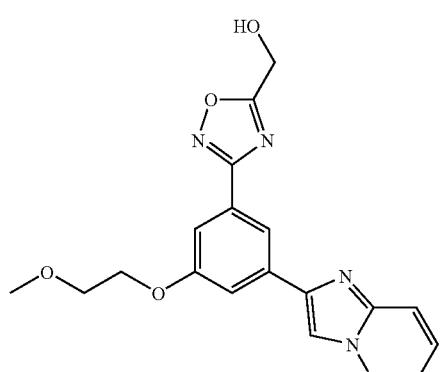
Compound 35
Compound 36
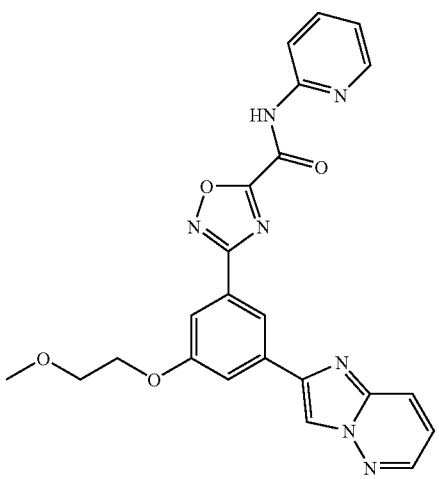
Compound 37
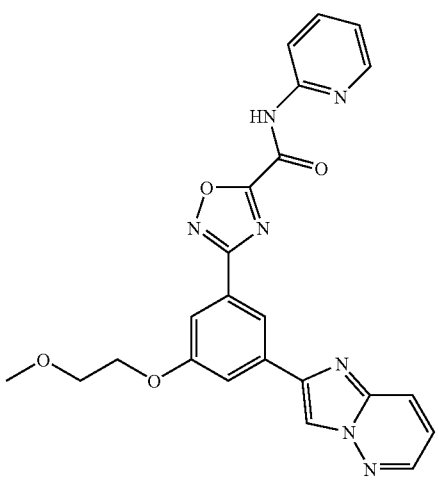
Compound 38
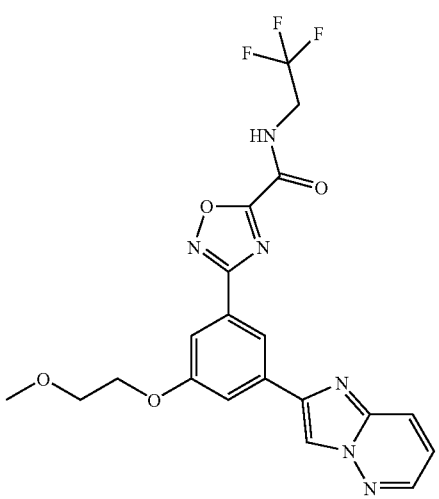

Compound 39
Compound 40
Compound 41
Compound 42
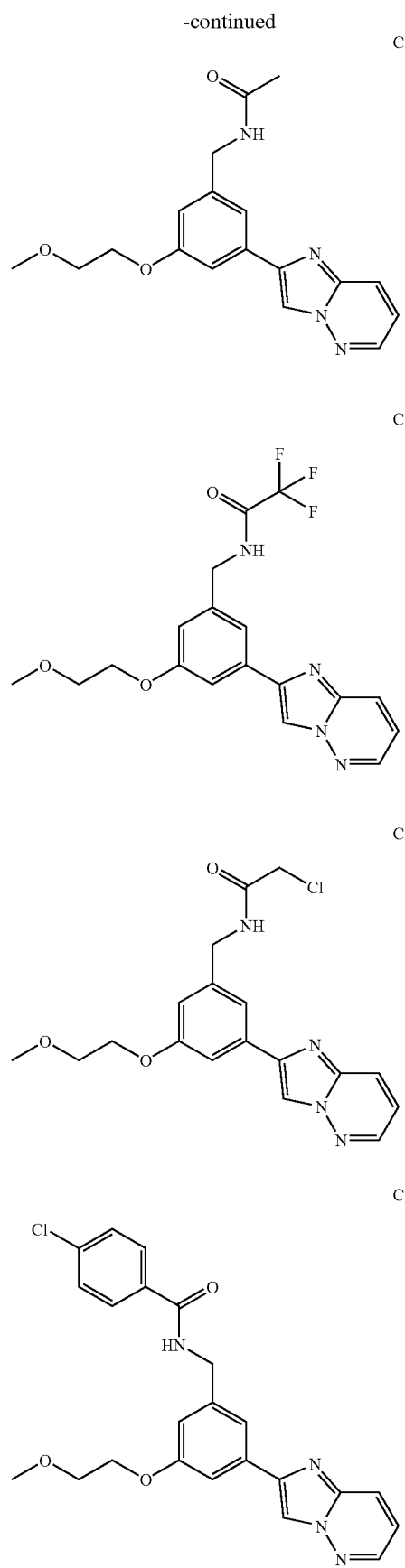
Compound 43
Compound 44
Compound 45
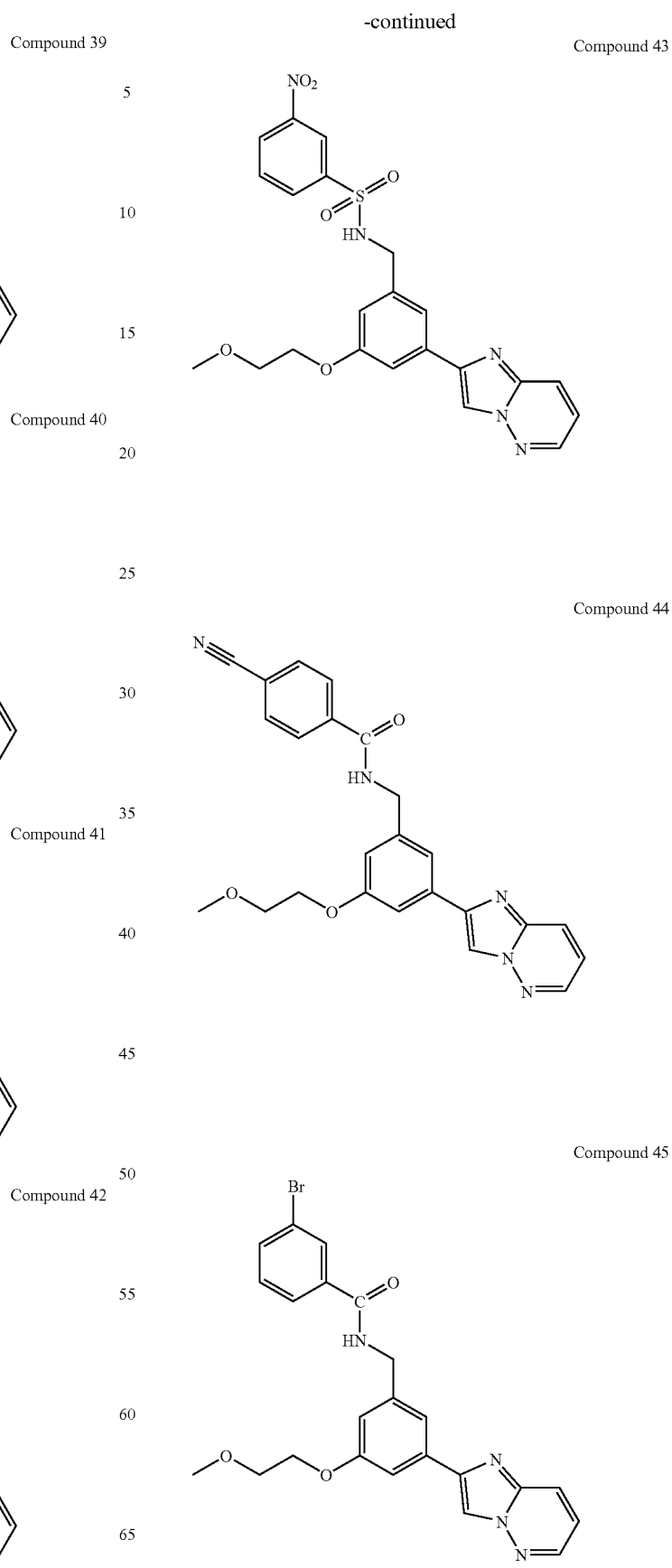

-continued
Compound 46
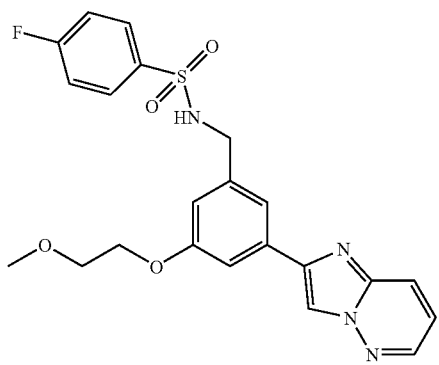
Compound 47
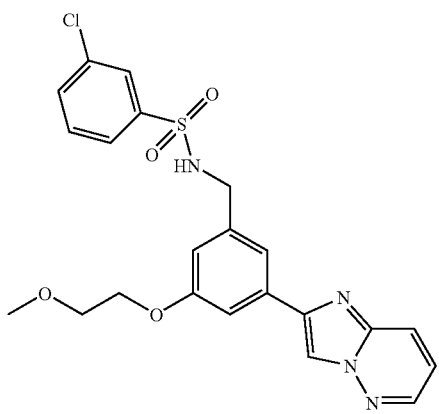
Compound 48
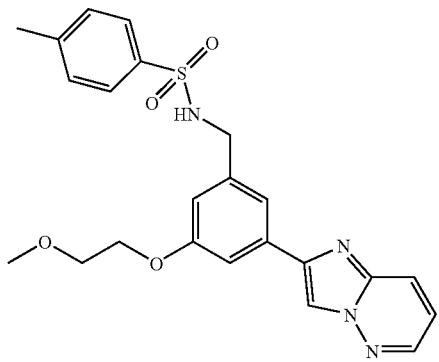
Compound 49
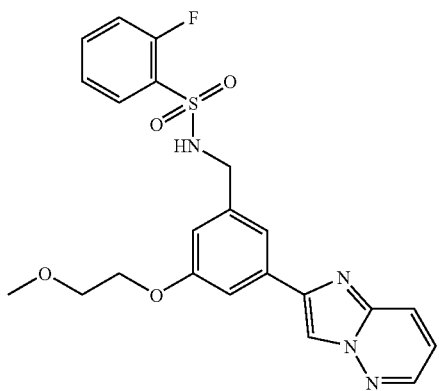
-continued
Compound 50
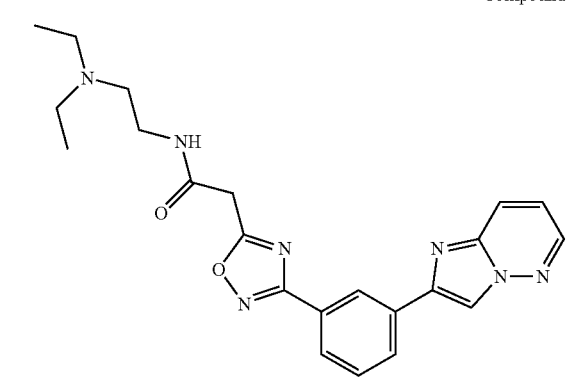
Compound 51
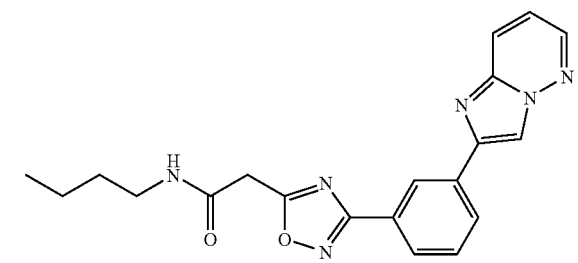
Compound 52
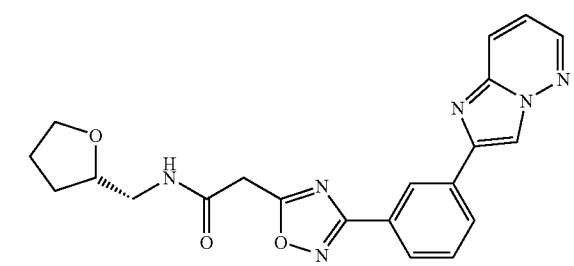
Compound 53
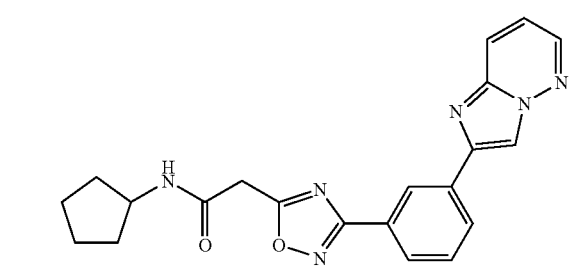
Compound 54
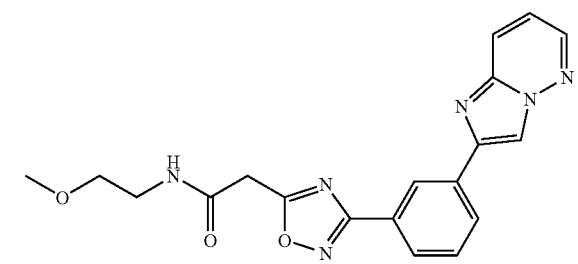

-continued
Compound 55
Compound 56
Compound 57
Compound 58
Compound 59
Compound 60
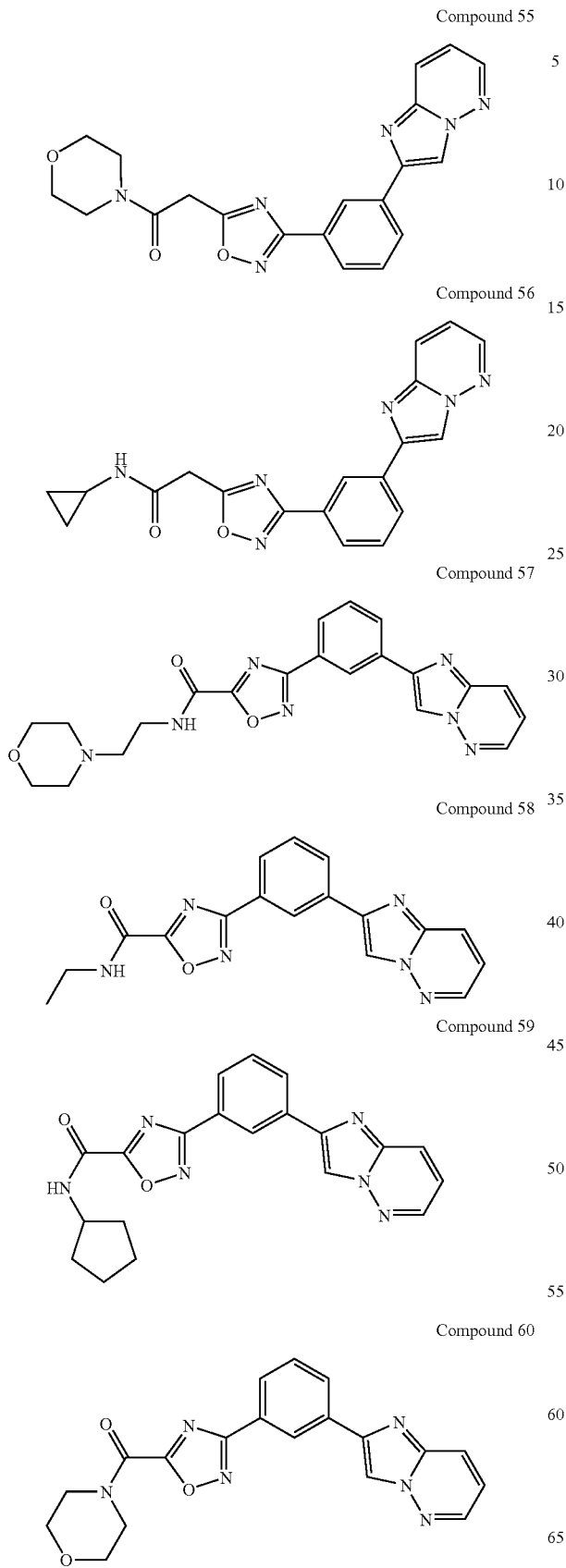
-continued
Compound 61
Compound 62
Compound 63
Compound 64
Compound 65
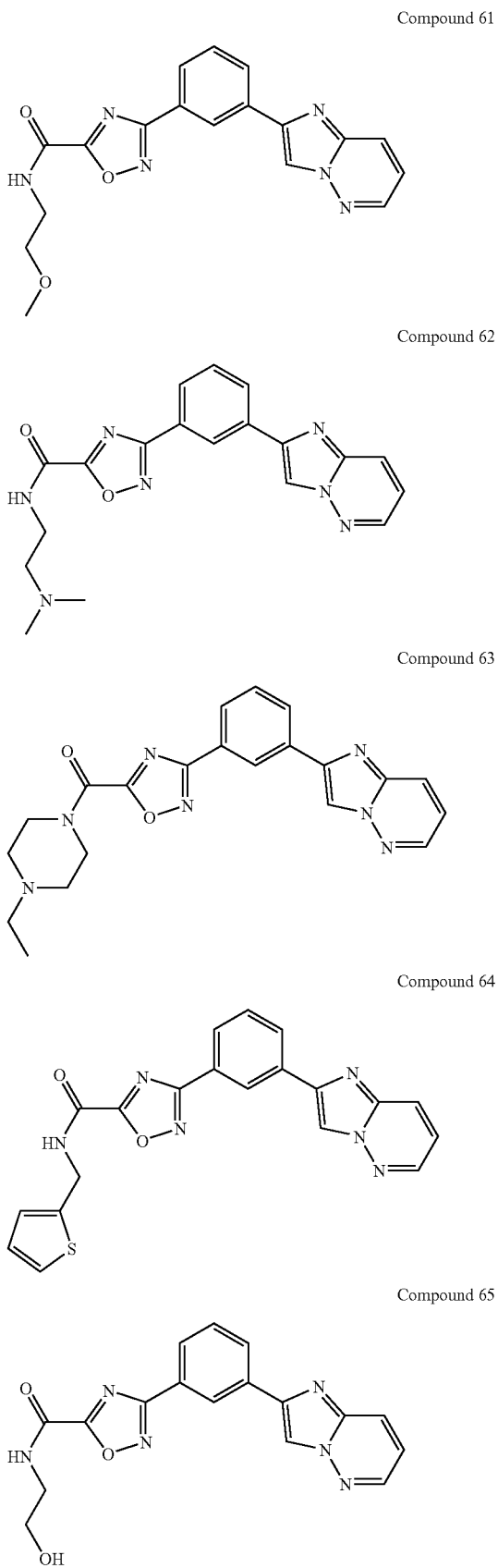

Compound 66
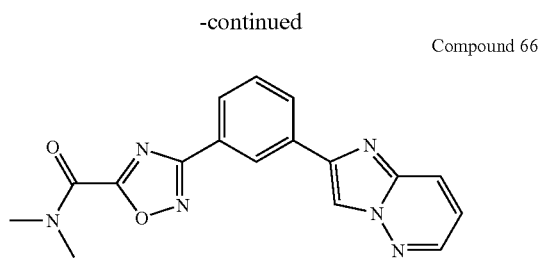
Compound 67
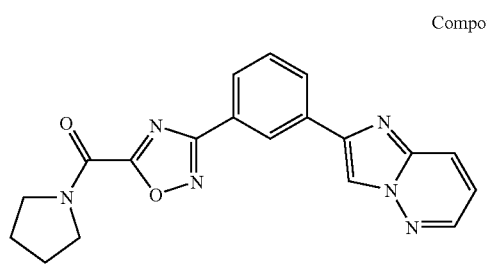
Compound 68
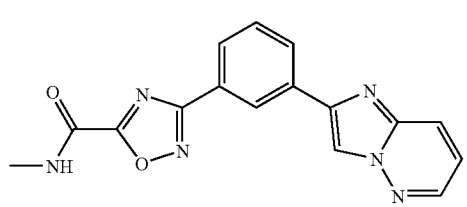
Compound 69
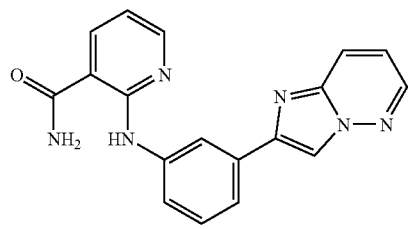
Compound 70
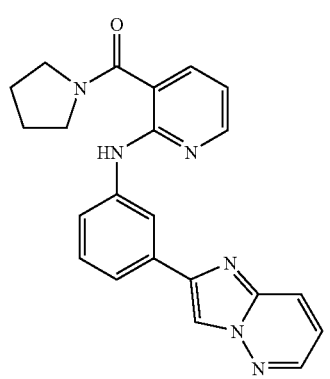
Compound 71
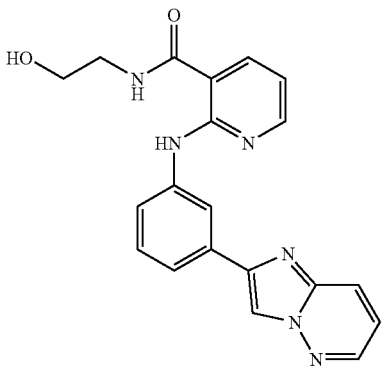
Compound 72
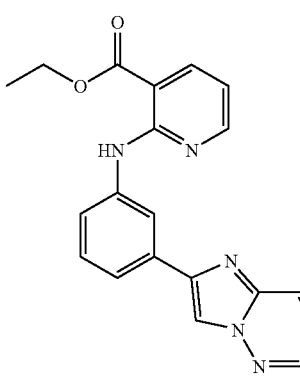
Compound 73
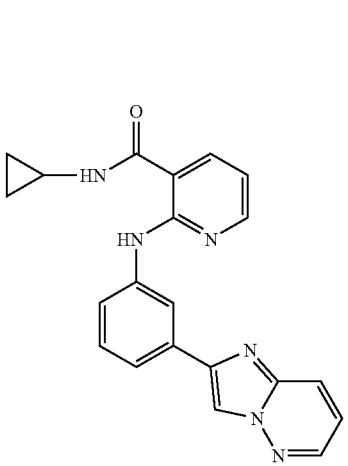
Compound 74
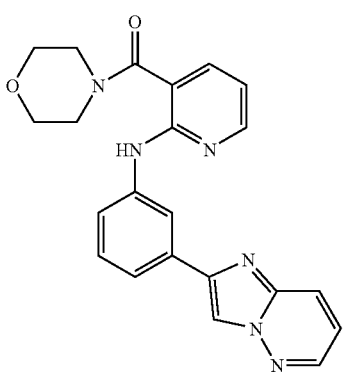

-continued
Compound 75
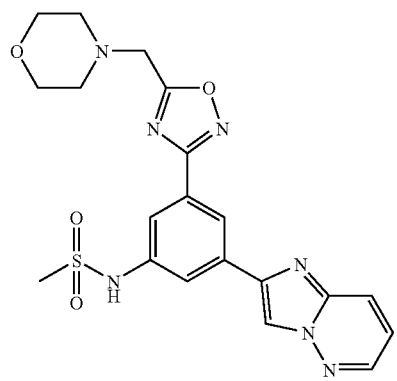
Compound 76
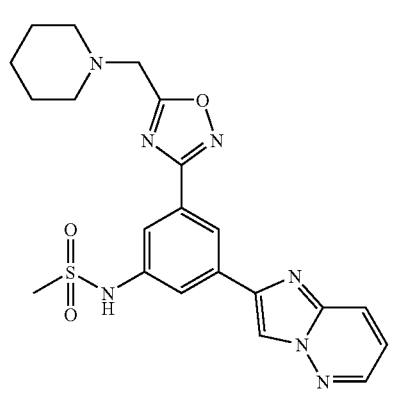
Compound 77
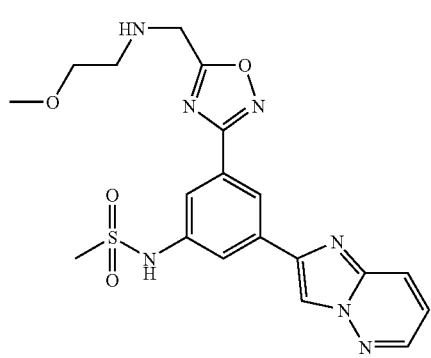
Compound 78
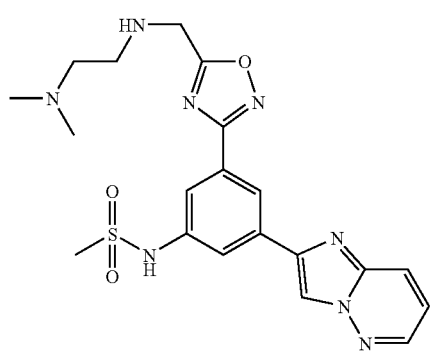
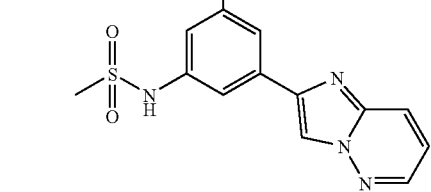
-continued
Compound 79
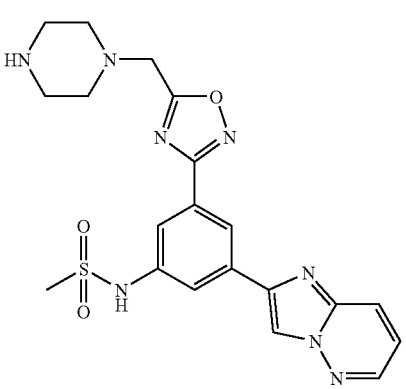
Compound 80
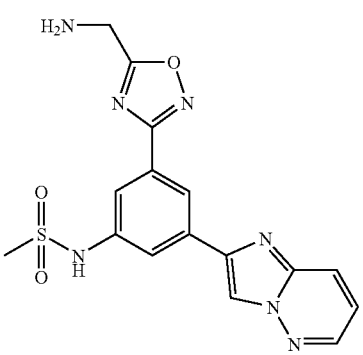
Compound 81
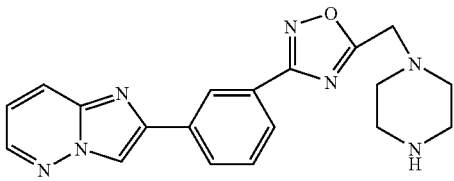
Compound 82
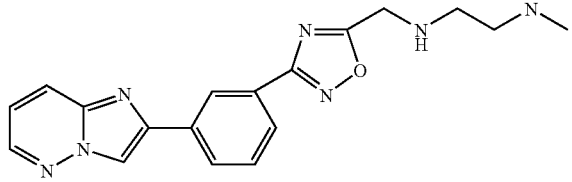
Compound 83
Compound 84
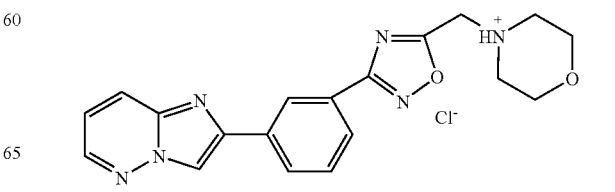

-continued
Compound 85
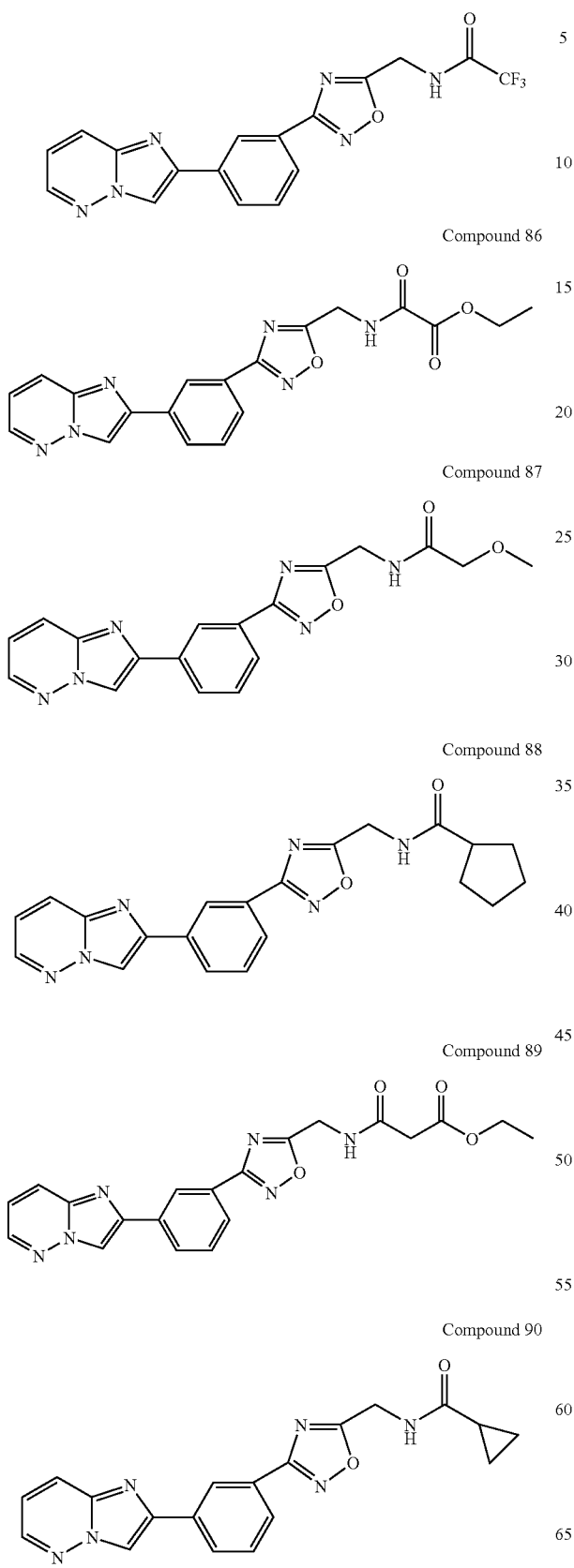
Compound 86
Compound 87
Compound 88
Compound 89
Compound 90
-continued
Compound 91
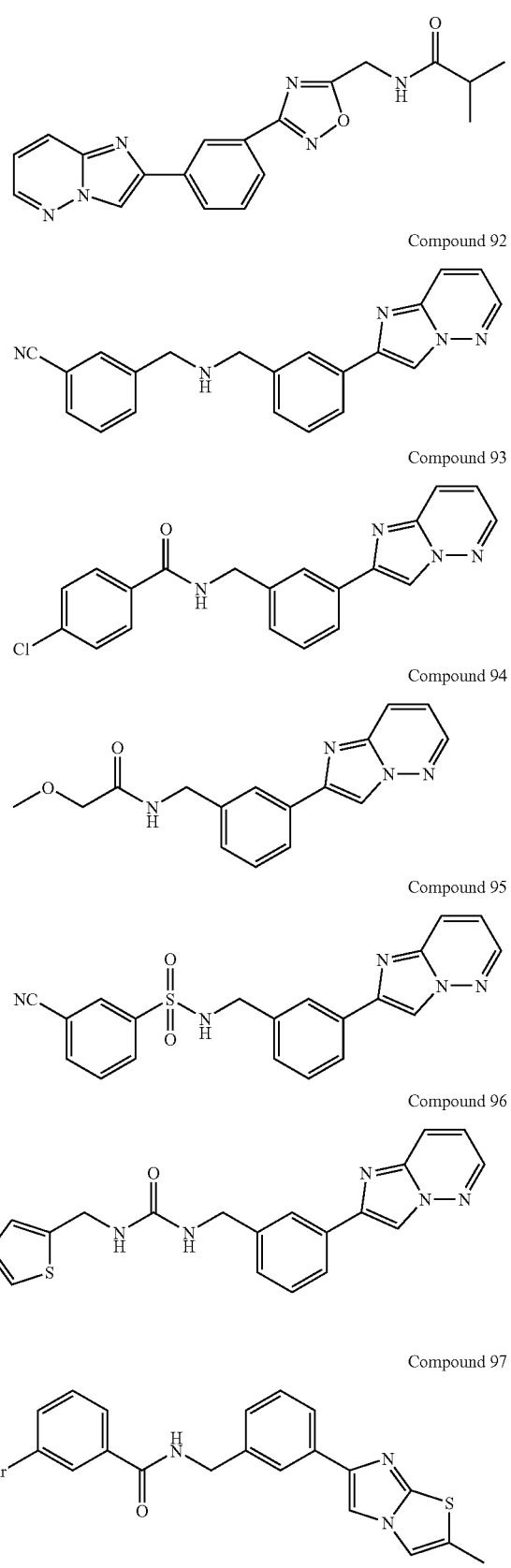
Compound 92
Compound 93
Compound 94
Compound 95
Compound 96
Compound 97

-continued

Compound 98
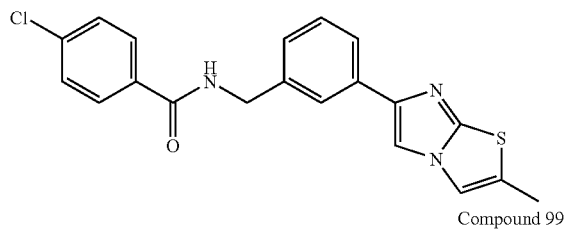

Compound 99
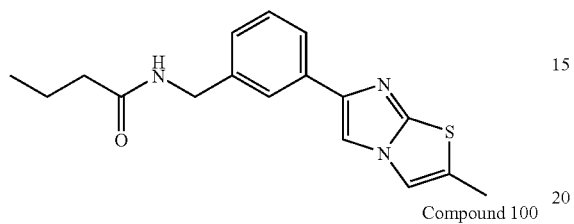

Compound 100
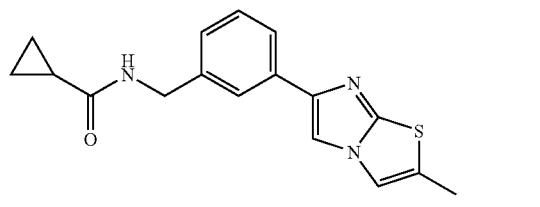

Compound 101
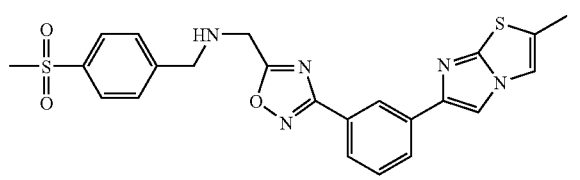

Compound 102
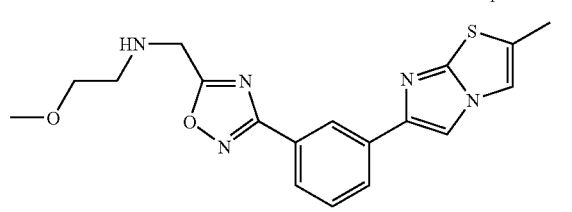

Compound 103
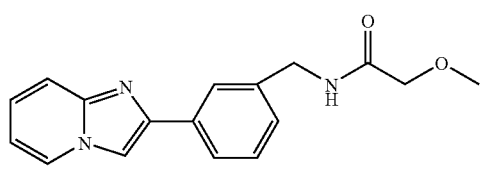

Compound 104

-continued

Compound 105
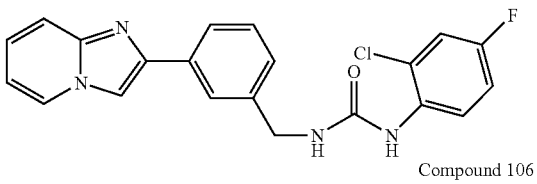

Compound 106
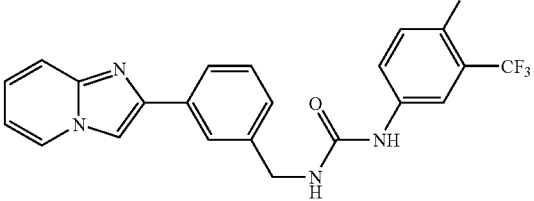

The compounds described above can be prepared by methods well known in the art. Examples 1-106 below provide detailed descriptions of how compounds 1-106 were actually prepared.

The compounds described above have one or more non-aromatic double bonds, and one or more asymmetric centers. They can occur as racemates, racemic mixtures, single enantiomers, individual diastereomers, diastereomeric mixtures, and cis- or trans- or E- or Z-double isomeric forms. Compounds of the invention also include tautomeric forms, such as keto-enol tautomers. Compounds of the invention can also include all isotopes of atoms occurring in the intermediates or final compounds. Isotopes include those atoms having the same atomic number but different mass numbers. For example, isotopes of hydrogen include tritium and deuterium.

One aspect of this invention is a method of lowering the level of a cytokine (e.g., TNFα or IL-1β), e.g., by inhibiting the production of the cytokine in a subject. A subject refers to any animal, including mammals, preferably mice, rats, other rodents, rabbits, dogs, cats, swine, cattle, sheep, horses, or primates, and most preferably humans. The method includes administering to the subject with an effective amount of one or more of the compounds described above. The term "an effective amount" is the amount of the compound which is required to confer the desired effect. Effective amounts may vary, as recognized by those skilled in the art, depending on route of administration, excipient usage, and the possibility of co-usage with other agents.

As the compounds described above lower the level of a cytokine in a subject, they can be used to treat a disorder caused by over-production of the cytokine. Thus, also within the scope of this invention is a method of treating a disorder related to cytokine over-production, i.e., an inflammatory disease, an autoimmune disease, cancer, diabetes, allergy or atherosclerosis. An autoimmune disease includes but is not limited to rheumatoid arthritis, inflammatory bowel disease (including Crohn's disease and ulcerative colitis), multiple sclerosis, psoriasis, or septic shock. The method includes administering to a subject in need of the treatment an effective amount of one of the compounds described above.

The term "treating" or "treatment" refers to the application or administration of a composition including the compound to a subject, who has one of the above-mentioned disorders, a symptom of the disorder, or a predisposition toward the disorder, with the purpose to cure, heal, alleviate, relieve, alter, remedy, ameliorate, improve, or affect the disorder, the symptoms of the disorder, or the predisposition toward the disorder.

To practice the treatment method of this invention, one or more of the compounds described above are mixed with a pharmaceutically acceptable carrier and then administered orally, rectally, parenterally, by inhalation spray, or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A composition for oral administration can be any orally acceptable dosage form including, but not limited to, tablets, capsules, emulsions and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A sterile injectable composition (e.g., aqueous or oleaginous suspension) can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents.

An inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

One or more active compounds can be administered rectally. One example is a suppository, which comprises the active compounds with a suppository base. Suitable suppository bases are, for example, natural or synthetic triglycerides, or paraffin hydrocarbons. Another example is a gelatin rectal capsule which comprise the active compounds and a base. Possible base materials include, for example, liquid triglycerides, polyethylene glycols, or paraffin hydrocarbons.

A composition that is applied to the skin can be formulated in form of oil, cream, lotion, ointment and the like. Suitable carriers for the composition include vegetable or mineral oils, white petrolatum (white soft paraffin), branched chain fats or oils, animal fats and high molecular weight alcohols (greater than C12). The preferred carriers are those in which the active ingredient is soluble. Emulsifiers, stabilizers, humectants and antioxidants may also be included as well as agents imparting color or fragrance, if desired. Additionally, transdermal penetration enhancers may be employed in these topical formulations. Examples of such enhancers can be found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil, such as almond oil, is admixed. An example of such a cream is one which includes about 40 parts water, about 20 parts beeswax, about 40 parts mineral oil and about 1 part almond oil.

Ointments may be formulated by mixing a solution of the active ingredient in a vegetable oil, such as almond oil, with warm soft paraffin and allowing the mixture to cool. An example of such an ointment is one which includes about 30% almond and about 70% white soft paraffin by weight.

A carrier in a pharmaceutical composition must be "acceptable" in the sense of being compatible with the active ingredient of the formulation (and preferably, capable of stabilizing it) and not deleterious to the subject to be treated. For example, solubilizing agents, such as cyclodextrins (which form specific, more soluble complexes with the active compounds), can be utilized as pharmaceutical excipients for delivery of the active compounds. Examples of other carriers include colloidal silicon dioxide, magnesium stearate, cellulose, sodium lauryl sulfate, and D&C Yellow #10.

A suitable in vitro assay can be used to preliminarily evaluate the efficacy of any of the above-described compounds in decreasing the level of a cytokine (e.g., TNFα or IL-1β). Compounds that demonstrate high activity in the preliminary screening can further be screened by in vivo assays (Example 107 below). For example, a test compound is administered to an animal (e.g., a mouse model) and its effects in lowering the level of a cytokine are then assessed. The compounds can further be examined to verify their efficacy in treating a disorder mediated by cytokine overproduction. For example, a compound can be administered to an animal (e.g., a mouse model) having inflammatory bowl disease and its therapeutic effects are then assessed. Based on the results, appropriate dosage ranges and administration routes can also be determined.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Compound 1: 2-(3-(5-methyl-1,2,4-oxadiazol-3-yl)phenyl)imidazo[1,2-b]pyridazine was prepared as outlined and described below.

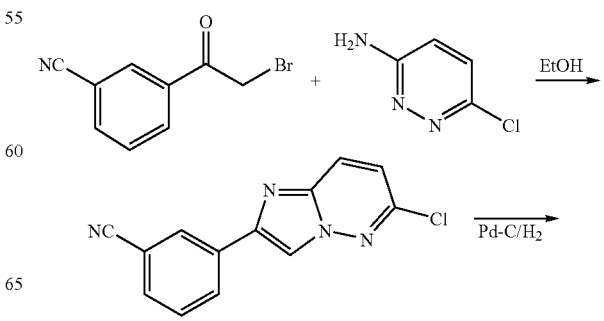

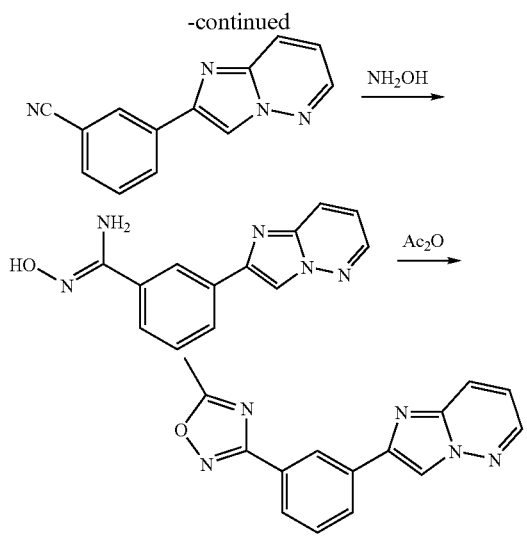

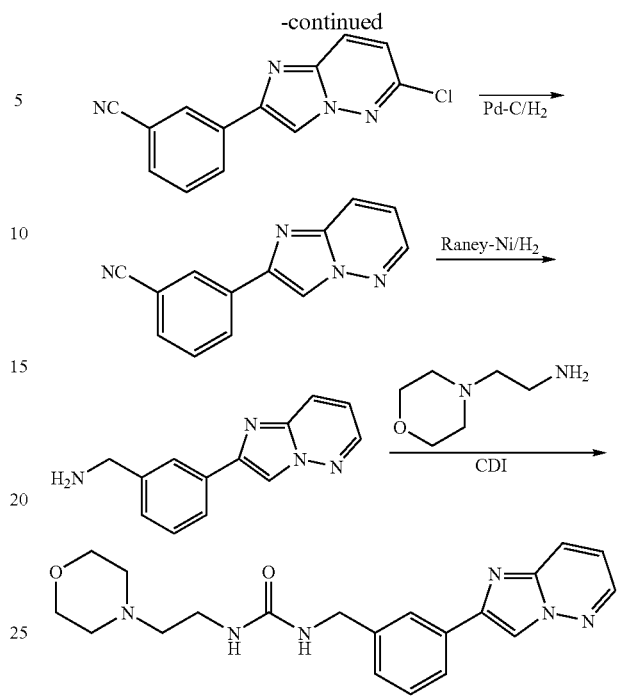

1 mmol 3-(2-bromoacetyl)benzonitrile and 1 mmol 6-chloropyridazin-3-amine in 10 ml EtOH were heated to reflux for 12 h, then cooled to room temperature. The orange-red precipitate was collected by filtration, washed with cold EtOH, and air-dried to give the 3-(6-chloroimidazo[1,2-b]pyridazin-2-yl)benzonitrile (125 mg, 50%).

2.5 mg 10% Pd-C were added to the solution of 3-(6-chloroimidazo[1,2-b]pyridazin-2-yl)benzonitrile (50 mg, 0.2 mmol) in THF/MeOH 25 ml. The reaction mixture was stirred vigorously at room temperature for 4 h under hydrogen and the Pd—C was then removed. The filtrate was concentrated in vacuo to give the 3-(imidazo[1,2-b]pyridazin-2-yl)benzonitrile as a yellow-white solid.

A mixture of 0.5 mmol 3-(imidazo[1,2-b]pyridazin-2-yl)benzonitrile, 1 mmol NH$_2$OH.HCl and 1 mmol Et$_3$N in EtOH were stirred at reflux for 4 h then cooled. Excess of solvent was removed in vacuo to afford the crude product. Acetic anhydride (2 mmol) was added to the mixture solution of the crude product, THF (15 ml), and DMAP (cat.) at room temperature and then the mixture was heated to reflux for 12 h. The mixture was concentrated in vacuo and the crude product was purified by column chromatography on silica gel to give the 2-(3-(5-methyl-1,2,4-oxadiazol-3-yl)phenyl)imidazo[1,2-b]pyridazine.

$^1$H NMR (MeOD, 400 MHz): δ 8.676~8.650 (m, 1H), 8.606 (s, 1H), 8.444~8.424 (dd, J=6.0 Hz, 2.0 Hz, 1H), 8.150~8.113 (m, 1H), 8.041~7.988 (m, 2H), 7.631~7.580 (t, J=6.0 Hz, 1H), 7.266~7.220 (dd, J=6.0 Hz, 2.0Hz, 1H); MS (m/e): 278.4 (M+1).

EXAMPLE 2

Compound 2: 1-(3-(imidazo[1,2-b]pyridazin-2-yl)benzyl)-3-(2-morpholinoethyl)urea was prepared as outlined and described below.

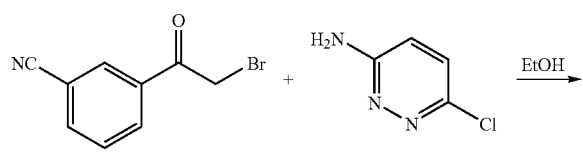

Raney-Ni (cat.) and NH$_3$.H$_2$O (4~5 drops) were added to the solution of 3-(imidazo[1,2-b]pyridazin-2-yl)benzonitrile (25 mg) in MeOH. The mixture was stirred vigorously at room temperature for 1 h under hydrogen and the Raney-Ni was then removed. The filtration was concentrated in vacuo to give the (3-(imidazo[1,2-b]pyridazin-2-yl)phenyl)methanamine.

0.2 mmol (3-(imidazo[1,2-b]pyridazin-2-yl)phenyl)methanamine and 1 mmol K$_2$CO$_3$ in dry Toluene were stirred for 30 min at 30° C., added with CDI (0.2 mmol), and kept to stir for 2 h. Then 0.2 mmol 2-morpholinoethanamine and DMAP (cat.) were added and the solution was heated to 60° C. for 2 h. The reaction was concentrated in vacuo and the residue was purified by column chromatography on silica gel to give the 1-(3-(imidazo[1,2-b]pyridazin-2-yl)benzyl)-3-(2-morpholinoethyl)urea.

$^1$H NMR (MeOD, 400 MHz): δ 8.526 (s,1H), δ 8.430~8.409 (dd, J=6.0 Hz, 2.4 Hz, 1H), 8.001~7.971 (d, J=12 Hz, 1H), 7.910 (s, 1H), 7.866~7.847 (d, J=8 Hz, 1H), 7.445~7.394 (t, J=10 Hz, 1H), 7.325~7.301 (d, J=10.0 Hz, 1H), 7.251~7.206 (dd, J=12.0 Hz, 5.6 Hz, 1H), 3.733~3.666 (m, 4H), 3.336~3.268 (m, 4H), 2.615~2.543 (m, 6H); MS (m/e): 381.4 (M+1).

EXAMPLE 3

Compound 3: 1-(3-(imidazo[1,2-b]pyridazin-2-yl)benzyl)-3-(2-methoxyethyl)urea was prepared in a manner similar to that described in Example 2.

$^1$H NMR (CD$_3$OD, 400 MHz): δ 8.533 (s, 1H), 8.429~8.411 (dd, J=6.0 Hz, 1.2 Hz, 1H), 8.005~7.970 (dd, J=12.4 Hz, 2.0 Hz, 1H), 7.897 (s, 1H), 7.874~7.850 (d, J=10.4 Hz, 1H), 7.444~7.394 (t, J=9.6~10.4 Hz, 1H), 7.321~7.298 (d, J=9.2 Hz, 1H), 7.251~7.206 (dd, J=12.4 Hz, 1.6 Hz, 1H), 3.694~3.662 (m, 3H), 3.440~3.402 (t, J=7.6 Hz, 2H), 3.329 (s, 2H), 3.277~3.240 (t, J=6.8~8.0 Hz, 2H); MS (m/e): 326.3 (M+1).

EXAMPLE 4

Compound 4: N-((3-(3-(imidazo[1,2-b]pyridazin-2-yl)phenyl)-1,2,4-oxadiazol-5-yl)methyl)-2-methoxyethanamine was prepared as outlined and described below.

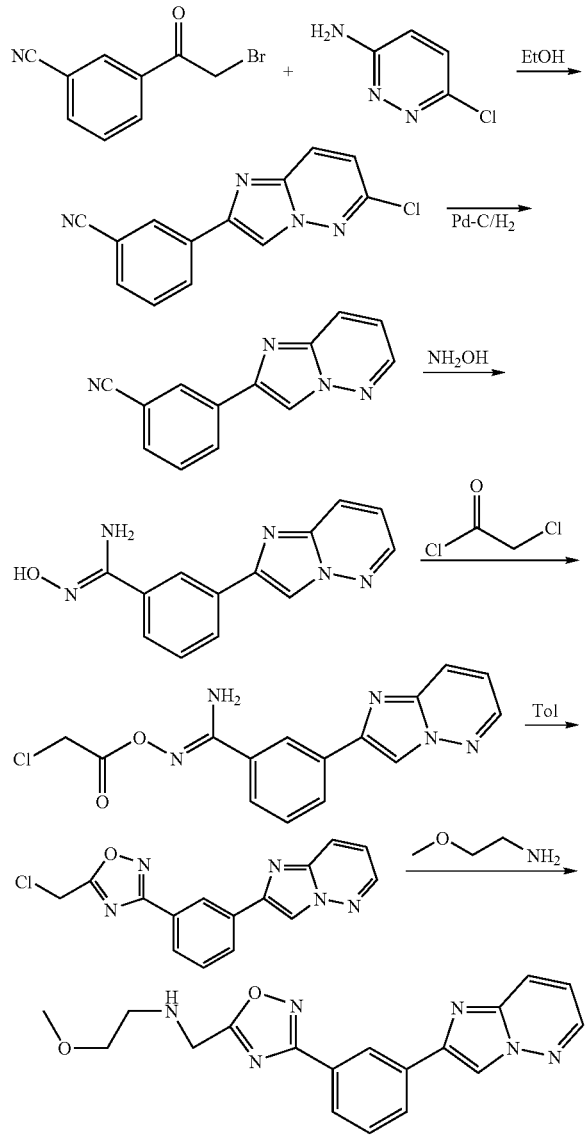

A mixture of 0.5 mmol 3-(imidazo[1,2-b]pyridazin-2-yl)benzonitrile, 1 mmol NH$_2$OH.HCl and 1 mmol Et$_3$N in EtOH was stirred at reflux for 4 h then cooled. Excess of solvent was removed in vacuo to afford the crude product. 2-chloroacetyl chloride (2 mmol) was added to the mixture solution of the crude product in Toluene (15 ml) at room temperature and then the mixture was heated to reflux for 5 h. The mixture was concentrated in vacuo and the crude product was purified by column chromatography on silica gel to give the 2-(3-(5-(chloromethyl)-1,2,4-oxadiazol-3-yl)phenyl)imidazo[1,2-b]pyridazine.

A mixture of 2-(3-(5-(chloromethyl)-1,2,4-oxadiazol-3-yl)phenyl)imidazo[1,2-b]pyridazine(1.5 mmol), sodium iodide(cat.) and 2-methoxyethanamine(3 mmol) in 25 mL EtOH was stirred under reflux for 2 h. The mixture was concentrated in vacuo and the crude product was purified by column chromatography on silica gel to give the N-((3-(3-(imidazo[1,2-b]pyridazin-2-yl)phenyl)-1,2,4-oxadiazol-5-yl)methyl)-2-methoxyethanamine.

$^1$H NMR (CDCl$_3$, 400 MHz): δ 8.667 (s, 1H), 8.386 (s, 1H), 8.326~8.306 (dd, J=6.0 Hz, 2.0 Hz, 1H), 8.211~8.181 (dd, J=10.4 Hz, 1.6Hz, 1H), 8.109~8.080 (dd, J=10.4 Hz, 1.6 Hz, 1H), 7.999~7.969 (d, J=12 Hz, 1H), 7.619~7.566 (t, J=10.4 Hz, 1H), 7.082~7.037 (dd, J=11.6 Hz, 6.0 Hz, 1H), 4.188 (s, 2H), 3.577~3.544 (t, J=6~7.2 Hz, 2H), 3.378 (s, 3H), 2.967~2.935 (t, J=6.4 Hz, 2H); MS (m/e): 351.4 (M+1).

EXAMPLE 5

Compound 5: N-((3-(3-(imidazo[1,2-b]pyridazin-2-yl)phenyl)-1,2,4-oxadiazol-5-yl)methyl)-2-morpholinoethanamine was prepared in a manner similar to that described in Example 4.

$^1$H NMR (CDCl$_3$, 400 MHz): δ 8.663 (s, 1H), 8.370 (s, 1H), 8.323~8.303 (dd, J=6.0 Hz, 2.0 Hz, 1H), 8.177~8.146 (dd, J=6.4 Hz, 2.0 Hz, 1H), 8.077~8.052 (d, J=10.0 Hz, 1H), 8.000~7.967 (d, J=13.2 Hz, 1H), 7.612~7.560 (t, J=10.4 Hz, 1H), 7.082~7.038 (dd, J=12.0 Hz, 6.0 Hz, 1H), 4.188 (s, 2H), 3.811~3.781 (t, J=6.0 Hz, 4H), 2.914~2.875 (t, J=7.2 Hz, 2H), 2.662~2.536 (m, 6H); MS (m/e): 406.4 (M+1).

EXAMPLE 6

Compound 6: 2-(3-(5-(morpholinomethyl)-1,2,4-oxadiazol-3-yl)phenyl)imidazo[1,2-b]pyridazine was prepared in a manner similar to that described in Example 4.

$^1$H NMR (CDCl$_3$, 400 MHz): δ 8.670 (s, 1H), 8.383 (s, 1H), 8.326~8.307 (dd, J=6.0 Hz, 1.6 Hz, 1H), 8.209~8.180 (dd, J=10.4 Hz, 1.2 Hz, 1H), 8.114~8.084 (dd, J=8.8 Hz, 1.6 Hz, 1H), 7.997~7.962 (dd, J=12.0 Hz, 2.0 Hz, 1H), 7.620~7.568 (t, J=10~10.8 Hz, 1H), 7.085~7.040 (dd, J=12.0 Hz, 6.0 Hz, 1H), 3.948 (s, 2H), 3.803~3.772 (m, 4H), 2.704~2.674 (m, 4H); MS (m/e): 363.4 (M+1).

EXAMPLE 7

Compound 7: (3-(3-(imidazo[1,2-b]pyridazin-2-yl)phenyl)-1,2,4-oxadiazol-5-yl)-N,N-dimethylmethanamine was prepared in a manner similar to that described in Example 4.

$^1$H NMR (CDCl$_3$, 400 MHz): δ 8.682~8.671 (t, J=2.0 Hz, 1H), 8.382 (s, 1H), 8.318~8.297 (dd, J=6.0 Hz, 2.4Hz, 1H), 8.210~8.176 (dd, J=14.0 Hz, 2.0 Hz, 1H), 8.125~8.094 (dd, J=8.8 Hz, 2.0 Hz, 1H), 7.990~7.955 (dd, J=12.0 Hz, 2.0 Hz, 1H), 7.614~7.563 (t, J=10~12.0 Hz, 1H), 7.073~7.029 (dd, J=12.0 Hz, 6.0 Hz, 1H), 3.895 (s, 2H), 2.451 (s, 6H); MS (m/e): 321.3 (M+1).

EXAMPLE 8

Compound 8: 2-((3-(3-(imidazo[1,2-b]pyridazin-2-yl)phenyl)-1,2,4-oxadiazol-5-yl)methylamino)ethanol was prepared in a manner similar to that described in Example 4.

$^1$H NMR (CDCl$_3$, 400 MHz): δ 8.656 (s, 1H), 8.376(s, 1H), 8.318~8.298 (dd, J=10.0 Hz, 2.0 Hz, 1H), 8.190~8.164 (d, J=10.4 Hz, 1H), 8.083~8.057 (d, J=10.4 Hz, 1H), 7.993~7.960 (d, J=12.0 Hz, 1H), 7.613~7.561 (t, J=10.4

1H), 7.078~7.032 (dd, J=12.0 Hz, 6.0 Hz, 1H), 4.184 (s, 2H), 3.751~3.718 (t, J=6.0 Hz, 2H), 2.968~2.934 (t, J=6.4~7.8 Hz, 2H); MS (m/e): 337.3 (M+1).

EXAMPLE 9

Compound 9: N-((3-(3-(imidazo[1,2-b]pyridazin-2-yl)phenyl)-1,2,4-oxadiazol-5-yl)methyl)ethanamine was prepared in a manner similar to that described in Example 4.

$^1$H NMR (CDCl$_3$, 400 MHz): δ 8.669~8.659 (t, J=2.0 Hz, 1H), 8.382(s, 1H), 8.321~8.301 (dd, J=6.0 Hz, 2.0 Hz, 1H), 8.202~8.176 (d, J=10.4 Hz, 1H), 8.101~8.075 (d, J=10.4 Hz, 1H), 7.996~7.965 (d, J=12.0 Hz, 1H), 7.615~7.567 (t, J=9.6 Hz, 1H), 7.080~7.033 (dd, J=12.8 Hz, 6.0 Hz, 1H), 4.152 (s, 2H), 2.834~2.762 (q, J=9.6 Hz, 2H), 1.213~1.166 (t, J=9.6 Hz, 3H); MS (m/e): 321.3 (M+1).

EXAMPLE 10

Compound 10: 2-(3-(5-((4-fluorophenoxy)methyl)-1,2,4-oxadiazol-3-yl)phenyl)imidazo[1,2-b]pyridazine was prepared in a manner similar to that described in Example 4.

$^1$H NMR (CDCl$_3$, 400 MHz): δ 8.660 (s, 1H), 8.378(s, 1H), 8.330~8.315 (d, J=6.0 Hz, 1H), 8.211~8.182 (d, J=10.4 Hz, 1H), 8.106~8.079 (d, J=9.2 Hz, 1H), 7.996~7.963 (d, J=11.2 Hz, 1H), 7.625~7.569 (t, J=11.2 Hz, 1H), 7.088~6.764 (m, 5H), 5.340 (s, 2H); MS (m/e): 388.3 (M+1).

EXAMPLE 11

Compound 11: 2-(3-(5-(ethoxymethyl)-1,2,4-oxadiazol-3-yl)phenyl)imidazo[1,2-b]pyridazine was prepared in a manner similar to that described in Example 4.

$^1$H NMR (CDCl$_3$, 400 MHz): δ 8.675 (s, 1H), 8.381(s, 1H), 8.339~8.305 (m, 1H), 8.216~8.180 (dd, J=10.4 Hz, 2.4 Hz, 1H), 8.117~8.088 (d, J=9.2 Hz, 8.0 Hz, 1H), 8.000~7.971 (d, J=11.6 Hz, 1H), 7.619~7.568 (t, J=10.4 Hz, 1H), 7.082~7.038 (dd, J=12 Hz, 5.6 Hz, 1H), 4.819 (s, 2H), 3.776~3.707 (q, J=8.8 Hz, 2H), 1.343~1.278 (t, J=9.2 Hz,3H); MS (m/e): 322.3 (M+1).

EXAMPLE 12

Compound 12 2-(3-(5-(methoxymethyl)-1,2,4-oxadiazol-3-yl)phenyl)imidazo[1,2-b]pyridazine was prepared in a manner similar to that described in Example 4.

$^1$H NMR (CDCl$_3$, 400 MHz): δ 8.673 (s, 1H), 8.378(s, 1H), 8.317~8.298 (dd, J=5.6 Hz, 2.0 Hz, 1H), 8.210~8.183 (d, J=10.8 Hz, 1H), 8.113~8.088 (d, J=10.0 Hz, 1H), 7.988~7.958 (d, J=12.0 Hz, 1H), 7.618~7.566 (t, J=10.4 Hz, 1H), 7.074~7.030 (dd, J=12.0 Hz, 5.6 Hz, 1H), 4.778 (s, 2H), 3.579 (s, 3H); MS (m/e): 308.4 (M+1).

EXAMPLE 13

Compound 13 2-(3-(5-(trifluoromethyl)-1,2,4-oxadiazol-3-yl)phenyl)imidazo[1,2-b]pyridazine was prepared in a manner similar to that described in Example 1.

$^1$H NMR (CDCl$_3$, 400 MHz): δ 8.712 (s, 1H), 8.386(s, 1H), 8.332~8.313 (dd, J=6.0 Hz, 2.0 Hz, 1H), 8.237~8.207 (dd, J=10.4 Hz, 1.6 Hz, 1H), 8.127~8.098 (dd, J=10.0 Hz, 1.6 Hz, 1H), 8.007~7.977 (d, J=12.0 Hz, 1H), 7.653~7.603 (t, J=10.0 Hz, 1H), 7.095~7.050 (dd, J=12.0 Hz, 6.0 Hz, 1H); MS (m/e): 332.2 (M+1).

EXAMPLE 14

Compound 14: (3-(3-(imidazo[1,2-b]pyridazin-2-yl)phenyl)-1,2,4-oxadiazol-5-yl)methyl acetate was prepared in a manner similar to that described in Example 4.

$^1$H NMR (CDCl$_3$, 400 MHz): δ 8.663 (s, 1H), 8.381(s, 1H), 8.327~8.307 (dd, J=6.0 Hz, 2.0 Hz, 1H), 8.214~8.184 (dd, J=12.0 Hz, 2.4 Hz, 1H), 8.096~8.065 (dd, J=10.4 Hz, 2.0 Hz, 1H), 7.999~7.968 (d, J=12.4 Hz, 1H), 7.624~7.571 (t, J=10.4 Hz, 1H), 7.087~7.040 (dd, J=12.8 Hz, 6.0 Hz, 1H), 5.388 (s,2H), 2.241 (s,3H); MS (m/e): 336.3 (M+1).

EXAMPLE 15

Compound 15: 2-(3-(5-isopropyl-1,2,4-oxadiazol-3-yl)phenyl)imidazo[1,2-b]pyridazine was prepared in a manner similar to that described in Example 4.

$^1$H NMR (CDCl$_3$, 400 MHz): δ 8.647 (s, 1H), 8.385(s, 1H), 8.313 (s, 1H), 8.207~8.166 (m, 1H), 8.094~8.068 (d, J=10.4 Hz, 1H), 7.998~7.966 (d, J=12.8 Hz, 1H), 7.652~7.564 (m, 1H), 7.112~7.066 (m, 1H), 3.339~3.292 (m, 1H), 1.496~1.473 (d, J=7.2 Hz, 6H); MS (m/e): 306.3 (M+1).

EXAMPLE 16

Compound 16: (3-(3-(imidazo[1,2-b]pyridazin-2-yl)phenyl)-1,2,4-oxadiazol-5-yl)methanol was prepared in a manner similar to that described in Example 1.

$^1$H NMR (DMSO-d6, 400 MHz): δ 8.979 (s, 1H), 8.735(s, 1H), 8.522~8.507 (dd, J=6.0 Hz, 2.0 Hz, 1H), 8.251~8.229 (d, J=8.8 Hz, 1H), 8.174~8.140 (d, J=12.4 Hz, 1H), 7.996~7.969 (d, J=12.0 Hz, 1H), 7.677~7.623 (t, J=10.8 Hz, 1H), 7.274~7.229 (dd, J=12.0 Hz, 6.0 Hz, 1H), 5.733 (s,2H); MS (m/e): 294.2 (M+1).

EXAMPLE 17

Compound 17: 2-(3-(5-cyclopropyl-1,2,4-oxadiazol-3-yl)phenyl)imidazo[1,2-b]pyridazine was prepared in a manner similar to that described in Example 1.

$^1$H NMR (CDCl$_3$, 400 MHz): δ 8.611~8.602 (t, J=2.0 Hz, 1H), 8.374(s, 1H), 8.318~8.297 (dd, J=6.0 Hz, 2.4 Hz, 1H), 8.185~8.149 (dt, J=10.0 Hz, 2.0Hz, 1H), 8.058~8.024 (dt, J=10.0 Hz, 2.0 Hz, 1H), 7.994~7.958 (dd, J=12.0 Hz, 2.0 Hz, 1H), 7.595~7.543 (t, J=10.4 Hz, 1H), 7.075~7.029 (dd, J=12.4 Hz, 2.0 Hz, 1H), 3.308~3.253 (m, 1H), 1.376~1.229 (m, 4H); MS (m/e): 304.3 (M+1).

EXAMPLE 18

Compound 18: 2-(3-(5-(fluoromethyl)-1,2,4-oxadiazol-3-yl)phenyl)imidazo[1,2-b]pyridazine was prepared in a manner similar to that described in Example 1.

$^1$H NMR (CDCl$_3$, 400 MHz): δ 8.684 (s, 1H), 8.382(s, 1H), 8.327~8.312 (dd, J=10.0 Hz, 2.0 Hz, 1H), 8.222~8.193 (dd, J=10.0 Hz, 2.0 Hz, 1H), 8.111~8.084 (d, J=10.4 Hz, 1H), 7.999~7.958 (m, 1H), 7.635~7.582 (t, J=10.4 Hz, 1H), 7.249~7.192 (dd, J=10.0 Hz, 6.0 Hz, 1H), 5.729~5.717 (d, J=4.8 Hz, 1H), 5.573~5.562 (d, J=4.4Hz, 1H); MS (m/e): 296.2 (M+1).

EXAMPLE 19

Compound 19: 2-(3-(5-ethyl-1,2,4-oxadiazol-3-yl)phenyl)imidazo[1,2-b]pyridazine was prepared in a manner similar to that described in Example 1.

$^1$H NMR (CDCl$_3$, 400 MHz): δ 8.613 (s, 1H), 8.438~8.424 (d, J=6.4Hz, 1H), 8.397(s, 1H), 8.314~8.287 (d, J=10.8 Hz, 1H), 8.241~8.213 (d, J=11.2 Hz, 1H), 8.132~8.106 (d, J=10.4 Hz, 1H), 7.659~7.606 (t, J=10.8 Hz, 1H), 7.249~7.165 (m,

1H), 3.044~2.969 (q, J=10.0 Hz, 1H), 1.504~1.463 (t, J=10.0 Hz, 3H); MS (m/e): 292.3 (M+1).

EXAMPLE 20

Compound 20: N-methyl-2-(3-(5-(trifluoromethyl)-1,2,4-oxadiazol-3-yl)phenyl)imidazo[1,2-b]pyridazin-6-amine was prepared as outlined and described below.

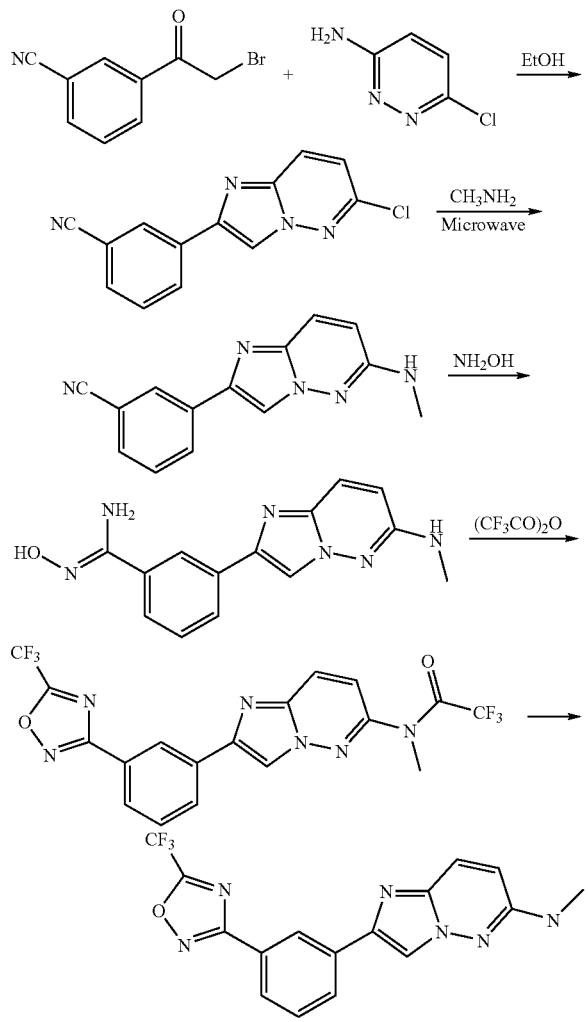

A mixture of 3-(6-chloroimidazo[1,2-b]pyridazin-2-yl)benzonitrile (0.25 mmol) and 10 mL methylamine methanol solution was heated at 125° C. in microwave synthesizer for 30 min. After purification to provide 3-(6-(methylamino)imidazo[1,2-b]pyridazin-2-yl)benzonitrile.

A mixture of 0.2 mmol 3-(6-(methylamino)imidazo[1,2-b]pyridazin-2-yl)benzonitrile, 0.8 mmol NH$_2$OH.HCl and 1 mmol Et$_3$N in EtOH were stirred at reflux for 4 h then cooled. Excess of solvent was removed in vacuo to afford the crude product. Trifluoroacetic anhydride (2 mmol) was added to the mixture solution of the crude product, THF (15 ml), and DMAP (cat.) at room temperature and then the mixture was heated to reflux for 12 h. The mixture was concentrated in vacuo and the crude product was purified by column chromatography on silica gel to give the 2,2,2-trifluoro-N-methyl-N-(2-(3-(5-(trifluoromethyl)-1,2,4-oxadiazol-3-yl)phenyl)imidazo[1,2-b]pyridazin-6-yl)acetamide.

A mixture of 2,2,2-trifluoro-N-methyl-N-(2-(3-(5-(trifluoromethyl)-1,2,4-oxadiazol-3-yl)phenyl)imidazo[1,2-b]pyridazin-6-yl)acetamide(0. 15 mmol) and K$_2$CO$_3$ (0.3 mmol) in 20 mL methanol -water(4:1) was heated at 60° C. for 1 h. The mixture was concentrated in vacuo and the crude product was purified by column chromatography on silica gel to give the N-methyl-2-(3-(5-(trifluoromethyl)-1,2,4-oxadiazol-3-yl)phenyl)imidazo[1,2-b]pyridazin-6-amine.

$^1$H NMR (DMSO-d$_6$, 400 MHz): δ 8.636~8.626 (t, J=2.0 Hz, 1H), 8.513(s, 1H), 8.166~8.130 (dt, J=10.4 Hz, 2.0 Hz, 1H), 7.947~7.916 (dd, J=10.4 Hz, 2.0Hz, 1H), 7.714~7.682 (d, J=12.8 Hz, 1H), 7.652~7.600 (t, J=10.4 Hz, 1H), 6.707~6.674 (d, J=10.0 Hz, 1H), 7.095~7.050 (dd, J=13.2 Hz, 1H), 3.350 (s, 3H); MS (m/e): 360.92 (M+1).

EXAMPLE 21

Compound 21: ethyl 3-(3-(imidazo[1,2-b]pyridazin-2-yl)phenyl)-1,2,4-oxadiazole-5-carboxylate was prepared in a manner similar to that described in Example 1.

$^1$H NMR (DMSO-d$_6$, 400 MHz): δ 9.013 (s, 1H), 8.765 (s, 1H), 8.522~8.511 (d, J=4.4 Hz, 1H), 8.287~8.267 (d, J=8.0 Hz, 1H), 8.173~8.151 (d, J=8.8 Hz, 1H), 8.034~8.015 (d, J=7.6 Hz, 1H), 7.702~7.662 (t, J=8.0 Hz, 1H), 7.273~7.239 (dd, J=9.2 Hz, 4.4 Hz, 1H), 4.492~4.438 (q, J=6.4 Hz, 2H), 1.394~1.359 (t, J=6.8Hz, 3H); MS (m/e): 336.0 (M+1).

EXAMPLE 22

Compound 22: ethyl 2-(3-(3-(imidazo[1,2-b]pyridazin-2-yl)phenyl)-1,2,4-oxadiazol-5-yl)acetate was prepared in a manner similar to that described in Example 1.

$^1$H NMR (DMSO-d$_6$, 400 MHz): δ 9.007 (s, 1H), 8.743~8.736 (t, J=1.6 Hz, 1H), 8.538~8.522 (dd, J=4.8 Hz, 1.6 Hz, 1H), 8.277~8.254 (dd, J=7.6 Hz, 1.6 Hz, 1H), 8.187~8.162 (dd, J=9.6 Hz, 0.8 Hz, 1H), 8.004~7.981 (dd, J=8.0 Hz, 1.6 Hz, 1H), 7.693~7.655 (t, J=7.6 Hz, 1H), 7.288~7.253 (dd, J=9.6 Hz, 4.8 Hz, 1H), 4.408 (s, 2H), 4.218~4.165 (q, J=7.2 Hz, 2H), 1.146~1.210 (t, J=7.2 Hz, 3H); MS (m/e): 350.0 (M+1).

EXAMPLE 23

Compound 23: 3-(3-(imidazo[1,2-b]pyridazin-2-yl)phenyl)-1,2,4-oxadiazole-5-carboxylic acid was prepared in a manner similar to that described in Example 1.

$^1$H NMR (CDCl$_3$, 400 MHz): δ 8.991 (s, 1H), 8.525~8.515 (d, J=4.0 Hz, 1H), 8.452 (s, 1H), 8.378~8.359 (d, J=7.6 Hz, 1H), 8.154~8.131 (d, J=9.2 Hz, 1H), 8.808~7.788 (d, J=8.0 Hz, 1H), 7.689~7.650 (t, J=8.0 Hz, 1H), 7.273~7.239 (dd, J=8.8 Hz, 4.0 Hz, 1H); MS (m/e): 307.8 (M+1).

EXAMPLE 24

Compound 24 3-(3-(imidazo[1,2-b]pyridazin-2-yl)phenyl)-1,2,4-oxadiazole-5-carboxamide was prepared in a manner similar to that described in Example 1.

$^1$H NMR (DMSO-d$_6$, 400 MHz): δ 8.985 (s, 1H), 8.775 (s, 1H), 8.524~8.514 (d, J=4.0 Hz, 1H), 8.275~8.256 (d, J=7.6 Hz, 1H), 8.161~8.139 (d, J=8.8 Hz, 1H), 8.026~8.006 (d, J=8.0 Hz, 1H), 7.701~7.661 (t, J=8.0 Hz, 1H), 7.273~7.240 (dd, J=8.8 Hz, 4.0 Hz, 1H); MS (m/e): 307.0 (M+1).

EXAMPLE 25

Compound 25: 2-(3-(3-(imidazo[1,2-b]pyridazin-2-yl)phenyl)-1,2,4-oxadiazol-5-yl)acetic acid was prepared in a manner similar to that described in Example 1.

$^1$H NMR (DMSO-$d_6$, 400 MHz): δ 9.003 (s, 1H), 8.739 (s, 1H), 8.535~8.520 (dd, J=4.4 Hz, 1.6 Hz, 1H), 8.269~8.249 (d, J=8.0 Hz, 1H), 8.186~8.163 (dd, J=9.2 Hz, 1H), 7.999~7.980 (d, J=7.6 Hz, 1H), 7.688~7.649 (t, J=8.0 Hz, 1H), 7.284~7.251 (dd, J=8.8 Hz, 4.4 Hz, 1H), 4.277 (s, 2H); MS (m/e): 321.8 (M+1).

EXAMPLE 26

Compound 26: 2-(3-(5-(methylthiomethyl)-1,2,4-oxadiazol-3-yl)phenyl)imidazo[1,2-b]pyridazine was prepared in a manner similar to that described in Example 4.

$^1$H NMR (DMSO-$d_6$, 400 MHz): δ 8.881 (s, 1H), 8.728(s, 1H), 8.484~8.469 (dd, J=4.4 Hz, 1.6 Hz, 1H), 8.228~8.221 (m, 1H), 8.128~8.105 (d, J=9.2 Hz, 1H), 7.999~7.980 (d, J=7.6 Hz, 1H), 7.646~7.607 (t, J=8.0 Hz, 1H), 7.245~7.211 (dd, J=9.2 Hz, 4.4 Hz, 1H), 4.112 (s, 2H); MS (m/e): 323.8 (M+1).

EXAMPLE 27

Compound 27: 2-(3-(5-(methylsulfonylmethyl)-1,2,4-oxadiazol-3-yl)phenyl)imidazo[1,2-b]pyridazine was prepared in a manner similar to that described in Example 4.

$^1$H NMR (DMSO-$d_6$, 400 MHz): δ 8.776 (s, 1H), 8.522(s, 1H), 8.302~8.286 (dd, J=4.8 Hz, 1.6 Hz, 1H), 8.051~8.031 (d, J=8.0 Hz, 1H), 7.962~7.936 (d, J=8.8Hz, 1H), 7.789~7.770 (d, J=7.6 Hz, 1H), 7.470~7.431 (t, J=8.0 Hz, 1H), 7.050~7.016 (dd, J=9.2 Hz, 4.4 Hz, 1H), 4.112 (s, 2H); MS (m/e): 355.9 (M+1).

EXAMPLE 28

Compound 28: (3-(imidazo[1,2-b]pyridazin-2-yl)-5-(2-methoxyethoxy)phenyl)methanamine was prepared as outlined and described below.

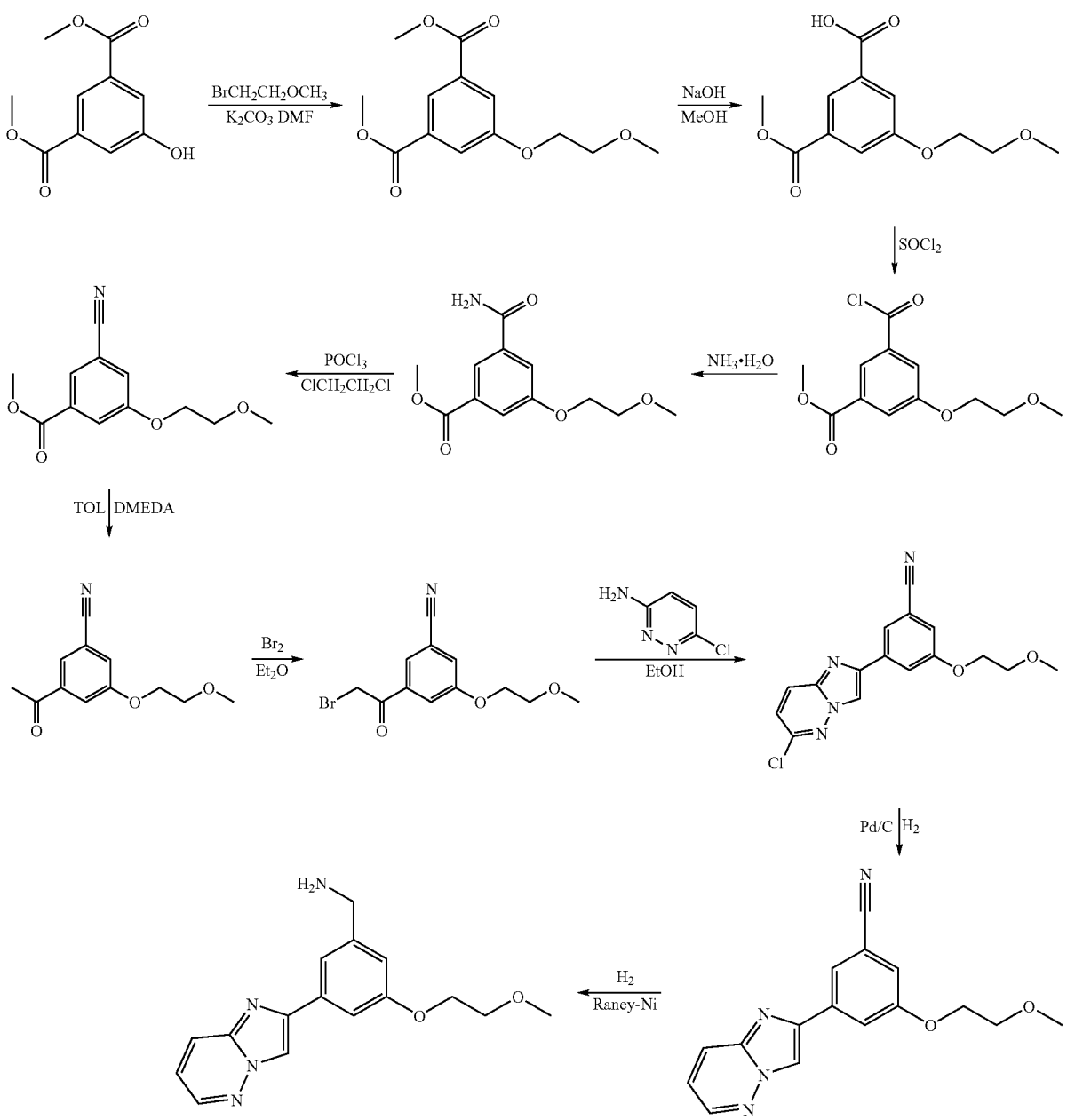

1-bromo-2-methoxyethane(5.8 mmol), dimethyl 5-hydroxyisophthalate(5 mL), $K_2CO_3$ (6 mmol) in DMF(10 mL) were stirred for 12 h at 60° C., then the solution was poured into water and the aqueous phase was extracted with EtOAc. The organic phase was washed with brine, dried ($MgSO_4$), filtered, and concentrated to give dimethyl 5-(2-methoxyethoxy)isophthalate (93.7%).

NaOH (45 mmol) was added to the solution of dimethyl 5-(2-methoxyethoxy)isophthalate (30 mmol) in 50 ml EtOH and stirred for 4 h at 40° C. Excess of solvent was removed in vacuo and the residue was treated with 1N HCl (aqueous) and extracted with EtOAc. The organic phase was washed with brine, dried ($MgSO_4$), filtered, and concentrated to afford 3-(methoxycarbonyl)-5-(2-methoxyethoxy)benzoic acid (87.3%).

3-(methoxycarbonyl)-5-(2-methoxyethoxy)benzoic acid (30 mmol) in 20 mL $SOCl_2$ was stirred at reflux for 4 h. Excess of $SOCl_2$ was removed in vacuo and the residue was dissolved in THF. Ammonia hydrate solution was added and the mixture was stirred at room temperature for 2 h. The solution was poured to the water and extracted with EtOAc. The organic phase was washed with brine, dried ($MgSO_4$), filtered, and concentrated to provide methyl 3-carbamoyl-5-(2-methoxyethoxy)benzoate(69.8%).

$POCl_3$ (20 mmol) was added to the solution of methyl 3-carbamoyl-5-(2-methoxyethoxy)benzoate (15 mmol) in 35 ml 1,2-dichloroethane and stirred for 5 h at reflux. Then the solution was cooled to room temperature, poured to the ice-water and extracted with EtOAc. The combined organic phases were dried ($MgSO_4$), filtered, and concentrated to yield methyl 3-cyano-5-(2-methoxyethoxy)benzoate (90.5%).

Solution of $AlMe_3$ in hexane (19 mmol) was dropped to the solution of DMEDA (24 mmol) in 60 ml dry toluene slowly at 0° C. under $N_2$. The solution was then continued to stir at room temperature for another 1 h and added methyl 3-cyano-5-(2-methoxyethoxy)benzoate (17.3 mmol) and stirred at reflux for 8 h. The mixture was poured to the water and extracted with EtOAc. The combined organic phases were dried ($MgSO_4$), filtered, and concentrated to give 3-acetyl-5-(2-methoxyethoxy)benzonitrile (58.6%).

$Br_2$ (31.5 mmol) was dropped into the solution of 3-acetyl-5-(2-methoxyethoxy)benzonitrile (30 mmol) in 150 ml ether at 0° C., then stirred at room temperature for 5 h. The solution was washed with brine, dried ($MgSO_4$), filtered, and concentrated to afford 3-(2-bromoacetyl)-5-(2-methoxyethoxy)benzonitrile (94.2%).

3-(2-bromoacetyl)-5-(2-methoxyethoxy)benzonitrile (15.3 mmol) and 6-chloropyridazin-3-amine (18 mmol) in 100 ml EtOH were stirred at reflux for 5 h, then cooled, filtered. The filter cake was 3-(6-chloroimidazo[1,2-b]pyridazin-2-yl)-5-(2-methoxyethoxy)benzonitrile (85.7%).

3-(6-chloroimidazo[1,2-b]pyridazin-2-yl)-5-(2-methoxyethoxy)benzonitrile (10 mmol) in 100 ml MeOH was added Pd/C(1 mmol) and stirred at room temperature for 4 h. Pd-C was removed and the filtrate was concentrated to provide 3-(imidazo[1,2-b]pyridazin-2-yl)-5-(2-methoxyethoxy)benzonitrile (98.9%).

3-(imidazo[1,2-b]pyridazin-2-yl)-5-(2-methoxyethoxy) benzonitrile (6 mmol) in 40 ml MeOH and 30 ml THF was added Raney-Ni (0.6mmol) and 1 ml ammonia hydrate solution and stirred at room temperature for 4 h. Raney-Ni was removed and the filtrate was concentrated to yield (3-(imidazo[1,2-b]pyridazin-2-yl)-5-(2-methoxyethoxy)phenyl) methanamine (70.2%).

$^1$H NMR ($CDCl_3$, 400 MHz): δ 3.441 (s,3H), 3.792 (t, J=4.2 Hz, 2H), 4.092 (s,2H), 4.241 (t, J=4.2 Hz, 2H), 7.034 (s,1H), 7.243 (m,1H), 7.601 (s,2H), 7.993 (d,1H), 8.438 (m,1H), 8.581(s,1H); MS (m/e): 299.7 (M+1).

EXAMPLE 29

Compound 29: 2-(3-(2-methoxyethoxy)-5-(5-(trifluoromethyl)-1,2,4-oxadiazol-3-yl)phenyl)imidazo[1,2-b]pyridazine was prepared in a manner similar to that described in Example 28.

$^1$H NMR (DMSO-$d_6$, 400 MHz): δ 3.358 (s,3H), 3.756(t, J=4.4 Hz, 2H), 4.302 (t, J=4.4 Hz, 2H), 7.256 (m, 1H), 7.567 (m, 1H), 7.954 (m, 1H), 8.200 (m, 1H), 8.397 (s, 1H), 8.567(s, 1H), 9.103 (s, 1H); MS (m/e): 406.2 (M+1).

EXAMPLE 30

Compound 30: 2-(3-(2-methoxyethoxy)-5-(5-methyl-1,2,4-oxadiazol-3-yl)phenyl)imidazo[1,2-b]pyridazine was prepared in a manner similar to that described in Example 28.

$^1$H NMR (DMSO-$d_6$, 400 MHz): δ 2.7532 (s,3H), 3.397 (s, 3H), 3.793(t, J=4.4 Hz, 2H), 4.283 (t, J=4.4 Hz, 2H), 7.245 (m, 1H), 7.489 (s, 1H), 7.803 (s, 1H), 8.183 (m, 1H), 8.384 (s, 1H), 8.653(m, 1H), 9.019 (s, 1H); MS (m/e): 352.2 (M+1).

EXAMPLE 31

Compound 31: 2-(3-(5-(fluoromethyl)-1,2,4-oxadiazol-3-yl)-5-(2-methoxyethoxy)phenyl)imidazo[1,2-b]pyridazine was prepared in a manner similar to that described in Example 28.

$^1$H NMR (DMSO-$d_6$, 400 MHz): δ 3.489 (s,3H), 3.822(t, J=4.4 Hz, 2H), 4.305 (t, J=4.4 Hz, 2H), 4.771 (s, 2H), 7.055 (m, 1H), 7.667 (m, 1H), 7.807 (m, 1H), 7.988 (m, 1H), 8.308 (m, 1H), 8.323 (m, 1H), 8.359 (s, 1H); MS (m/e): 370.9 (M+1).

EXAMPLE 32

Compound 32: 2-(3-(2-methoxyethoxy)-5-(5-(methoxymethyl)-1,2,4-oxadiazol-3-yl)phenyl)imidazo[1,2-b]pyridazine was prepared in a manner similar to that described in Example 28.

$^1$H NMR (DMSO-$d_6$, 400 MHz): δ 3.330 (s, 3H), 3.487 (s,3H), 3.714 (t, J=4.4 Hz, 2H), 4.270 (t, J=4.4 Hz, 2H), 4.900 (s, 2H), 7.260(dd, J1=3.6 Hz, J2=8.8 Hz, 1H), 7.471 (s, 1H), 7.834 (s, 1H), 8.155 (d, J=8.8 Hz, 1H), 8.349 (s,1H), 8.515 (d, J=3.6 Hz, 1H), 9.040 (s, 1H); MS (m/e): 382.2 (M+1).

EXAMPLE 33

Compound 33: 2-(3-(5-(ethoxymethyl)-1,2,4-oxadiazol-3-yl)-5-(2-methoxyethoxy)phenyl)imidazo[1,2-b]pyridazine was prepared in a manner similar to that described in Example 28.

$^1$H NMR (DMSO-$d_6$, 400 MHz): δ 1.189 (s, 3H), 3.340 (s, 3H), 3.364 (m, 2H), 3.716 (t, J=4.4 Hz, 2H), 4.271 (t, J=4.4 Hz, 2H), 4.881 (s, 2H), 7.269 (dd, J1=3.6 Hz, J2=8.8 Hz, 1H), 7.488 (s, 1H), 7.845 (s, 1H), 8.165 (d, J=8.8 Hz, 1H), 8.354 (s, 1H), 8.525 (d, J=3.6 Hz, 1H), 9.034 (s, 1H); MS (m/e): 396.4 (M+1).

EXAMPLE 34

Compound 34: (3-(3-(imidazo[1,2-b]pyridazin-2-yl)-5-(2-methoxyethoxy)phenyl)-1,2,4-oxadiazol-5-yl)methanol was prepared in a manner similar to that described in Example 28.

¹H NMR (DMSO-d₆, 400 MHz): δ 3.329 (s, 3H), 3.713 (t, J=4.4 Hz, 2H), 4.259 (t, J=4.4 Hz, 2H), 4.815 (s, 2H), 7.251 (dd, J1=3.6 Hz, J2=8.8 Hz, 1H), 7.469 (s, 1H), 7.829 (s, 1H), 8.150 (d, J=8.8 Hz, 1H), 8.347 (s, 1H), 8.513 (d, J=3.6 Hz, 1H), 9.027 (s, 1H); MS (m/e): 368.3 (M+1).

EXAMPLE 35

Compound 35: 3-(3-(imidazo[1,2-b]pyridazin-2-yl)-5-(2-methoxyethoxy)phenyl)-1,2,4-oxadiazole-5-carboxylic acid was prepared in a manner similar to that described in Example 28.

¹H NMR (DMSO-d₆, 400 MHz): δ 3.325 (s, 3H), 3.702 (t, J=4.4 Hz, 2H), 4.254 (t, J=4.4 Hz, 2H), 7.272 (dd, J=4 Hz, 8.4 Hz, 1H), 7.432 (s, 1H), 7.940 (s, 1H), 8.058 (s, 1H), 8.160 (d, J=8.4 Hz, 1H), 8.536 (d, J=4 Hz, 1H), 9.035 (s, 1H); MS (m/e): 382.3 (M+1).

EXAMPLE 36

Compound 36: 3-(3-(imidazo[1,2-b]pyridazin-2-yl)-5-(2-methoxyethoxy)phenyl)-1,2,4-oxadiazole-5-carboxamide was prepared in a manner similar to that described in Example 28.

¹H NMR (DMSO-d₆, 400 MHz): δ 3.359 (s, 3H), 3.747 (t, J=4.4Hz, 2H), 4.291 (t, J=4.4 Hz, 2H), 7.281 (dd, J=4 Hz, 8.4 Hz, 1H), 7.552 (s, 1H), 7.883 (s, 1H), 8.169 (s, 1H), 8.420 (d, J=8.4 Hz, 1H), 8.540 (d, J=4 Hz, 1H), 9.054 (s, 1H); MS (m/e): 381.3 (M+1).

EXAMPLE 37

Compound 37: 3-(3-(imidazo[1,2-b]pyridazin-2-yl)-5-(2-methoxyethoxy)phenyl)-N-(pyridin-2-yl)-1,2,4-oxadiazole-5-carboxamide was prepared in a manner similar to that described in Example 28.

¹H NMR (DMSO-d₆, 400 MHz): δ 3.333 (s, 3H), 3.704 (t, J=4.4 Hz, 2H), 4.262 (t, J=4.4 Hz, 2H), 5.877 (m, 3H), 6.451 (m, 1H), 7.280 (dd, J=4 Hz, 8.4 Hz, 1H), 7.425 (s, 1H), 7.952 (s, 1H), 8.059 (s, 1H), 8.160 (d, J=8.4 Hz, 1H), 8.547 (d, J=4 Hz, 1H), 9.047 (s, 1H); MS (m/e): 458.4 (M+1).

EXAMPLE 38

Compound 38: 3-(3-(imidazo[1,2-b]pyridazin-2-yl)-5-(2-methoxyethoxy)phenyl)-N-(2,2,2-trifluoroethyl)-1,2,4-oxadiazole-5-carboxamide was prepared in a manner similar to that described in Example 28.

¹H NMR (DMSO-d₆, 400 MHz): δ 3.362 (s, 3H), 3.750 (t, J=4.4 Hz, 2H), 4.171 (m, 2H), 4.304 (t, J=4.4 Hz, 2H), 7.284 (dd, J=4 Hz, 8.4 Hz, 1H), 7.571 (s, 1H), 7.899 (s, 1H), 8.176 (d, J=8.4 Hz, 1H), 8.546 (d, J=4 Hz, 1H), 9.066 (s, 1H); MS (m/e): 463.2 (M+1).

EXAMPLE 39

Compound 39: N-(3-(imidazo[1,2-b]pyridazin-2-yl)-5-(2-methoxyethoxy)benzyl)acetamide was prepared in a manner similar to that described in Example 28.

¹H NMR (CDCl₃, 400 MHz): δ 1.845 (m, 3H), 3.546 (s, 3H), 3.726 (d, J=4.4 Hz, 2H), 4.140 (d, J=4.4 Hz, 2H), 4.278 (m, 2H), 7.815 (s, 1H), 7.210 (m, 1H), 7.546 (m, 2H), 8.143 (m, 1H), 8.514 (m, 1H), 8.846 (s, 1H); MS (m/e): 341.4 (M+1).

EXAMPLE 40

Compound 40: N-(3-(imidazo[1,2-b]pyridazin-2-yl)-5-(2-methoxyethoxy)benzyl)-2,2,2-trifluoroacetamide was prepared in a manner similar to that described in Example 28.

¹H NMR (CDCl₃, 400 MHz): δ 3.389 (s, 3H), 3.678 (d, J=4.4 Hz, 2H), 4.178 (d, J=4.4 Hz, 2H), 4.453 (m, 2H), 6.843 (s, 1H), 7.243 (m, 1H), 7.630 (m, 2H), 8.102 (m, 1H), 8.513 (m, 1H), 8.874 (s, 1H); MS (m/e): 395.3 (M+1).

EXAMPLE 41

Compound 41: N-(3-(imidazo[1,2-b]pyridazin-2-yl)-5-(2-methoxyethoxy)benzyl)-2-chloroacetamide was prepared in a manner similar to that described in Example 28.

¹H NMR (CDCl₃, 400 MHz): δ 3.325 (s, 3H), 3.689 (d, J=4.4 Hz, 2H), 4.193 (m, 4H), 4.348 (m, 2H), 7.813 (s, 1H), 7.212 (m, 1H), 7.547 (m, 2H), 8.144 (m, 1H), 8.511 (m, 1H), 8.843 (s, 1H); MS (m/e): 375.2 (M+1).

EXAMPLE 42

Compound 42: N-(3-(imidazo[1,2-b]pyridazin-2-yl)-5-(2-methoxyethoxy)benzyl)-4-chlorobenzamide was prepared in a manner similar to that described in Example 28.

¹H NMR (CDCl₃, 400 MHz): δ 3.448 (s, 3H), 3.784 (d, J=4.4 Hz, 2H), 4.238 (d, J=4.4 Hz, 2H), 4.702 (m, 2H), 6.954 (s, 1H), 7.084 (m, 1H), 7.430 (m, 3H), 7.600 (s, 1H), 7.901 (m, 3H), 8.304 (m, 2H); MS (m/e): 438.2 (M+1).

EXAMPLE 43

Compound 43: N-(3-(imidazo[1,2-b]pyridazin-2-yl)-5-(2-methoxyethoxy)benzyl)-3-nitrobenzenesulfonamide was prepared in a manner similar to that described in Example 28.

¹H NMR (CDCl₃, 400 MHz): δ 3.447 (s, 3H), 3.785 (d, J=4.4 Hz, 2H), 4.178 (d, J=4.4 Hz, 2H), 4.354 (m, 2H), 5.403 (m, 1H), 6.783 (s, 1H), 7.105 (m, 1H), 7.314 (m,2H), 7.608 (m, 1H), 7.945 (m, 1H), 7.600 (s, 1H), 8.189 (m, 2H), 8.389 (m, 2H), 8.732 (s, 1H); MS (m/e): 484.3 (M+1).

EXAMPLE 44

Compound 44: N-(3-(imidazo[1,2-b]pyridazin-2-yl)-5-(2-methoxyethoxy)benzyl)-4-cyanobenzamide was prepared in a manner similar to that described in Example 28.

¹H NMR (CDCl₃, 400 MHz): δ 3.410 (s, 3H), 3.800 (d, J=4.4 Hz, 2H), 4.223 (d, J=4.4 Hz, 2H), 4.704 (m, 2H), 7.083 (m, 2H), 7.492 (s, 1H), 7.600 (s, 1H), 7.763 (m,2H), 7.845 (m, 1H), 7.904 (m, 1H), 8.154 (m, 1H), 8.304 (m, 2H); MS (m/e): 428.4 (M+1).

EXAMPLE 45

Compound 45: N-(3-(imidazo[1,2-b]pyridazin-2-yl)-5-(2-methoxyethoxy)benzyl)-3-bromobenzamide was prepared in a manner similar to that described in Example 28.

¹H NMR (CDCl₃, 400 MHz): δ 3.454 (s, 3H), 3.783 (d, J=4.4 Hz, 2H), 4.225 (d, J=4.4 Hz, 2H), 4.674 (m, 2H), 6.945 (s, 1H), 7.083 (m, 1H), 7.324 (m, 1H), 7.483 (s, 1H), 7.587 (s, 1H), 7.613 (m, 1H), 7.735 (m, 1H), 8.034 (m, 2H), 8.225 (s, 1H), 8.300 (m, 1H); MS (m/e): 482.3 (M+1).

EXAMPLE 46

Compound 46: N-(3-(imidazo[1,2-b]pyridazin-2-yl)-5-(2-methoxyethoxy)benzyl)-4-fluorobenzenesulfonamide was prepared in a manner similar to that described in Example 28.

¹H NMR (CDCl₃, 400 MHz): δ 3.456 (s, 3H), 3.800 (d, J=4.4 Hz, 2H), 4.206 (m, 4H), 5.034 (m, 1H), 6.800 (s, 1H), 7.107 (m, 1H), 7.203 (m, 2H), 7.453 (m, 2H), 7.904 (m, 3H), 8.200 (s, 1H), 8.367 (m, 1H); MS (m/e): 457.3 (M+1).

EXAMPLE 47

Compound 47: N-(3-(imidazo[1,2-b]pyridazin-2-yl)-5-(2-methoxyethoxy)benzyl)-3-chlorobenzenesulfonamide was prepared in a manner similar to that described in Example 28.
$^1$H NMR (CDCl$_3$, 400 MHz): δ 3.453 (s, 3H), 3.782 (d, J=4.4 Hz, 2H), 4.187 (d, J=4.4 Hz, 2H), 4.213 (m, 2H), 5.934 (m, 1H), 6.800 (s, 1H), 7.083 (m, 1H), 7.425 (m, 2H), 7.500 (m, 1H), 7.760 (m, 1H), 7.900 (m, 1H), 7.968 (m, 1H), 8.200 (s, 1H), 8.324 (m, 1H); MS (m/e): 473.9 (M+1).

EXAMPLE 48

Compound 48: N-(3-(imidazo[1,2-b]pyridazin-2-yl)-5-(2-methoxyethoxy)benzyl)-4-methylbenzenesulfonamide was prepared in a manner similar to that described in Example 28.
$^1$H NMR (CDCl$_3$, 400 MHz): δ 2.400 (s, 3H), 3.456 (s, 3H), 3.753 (d, J=4.4 Hz, 2H), 4.134 (m, 4H), 5.532 (m, 1H), 6.800 (s, 1H), 7.086 (m, 1H), 7.300 (m, 2H), 7.400 (s, 1H), 7.805 (m, 2H), 7.913 (m, 1H), 8.200 (s, 1H), 8.315 (m, 1H); MS (m/e): 453.4 (M+1).

EXAMPLE 49

Compound 49: N-(3-(imidazo[1,2-b]pyridazin-2-yl)-5-(2-methoxyethoxy)benzyl)-2-fluorobenzenesulfonamide was prepared in a manner similar to that described in Example 28.
$^1$H NMR (CDCl$_3$, 400 MHz): δ 3.478 (s, 3H), 3.782 (d, J=4.4 Hz, 2H), 4.187 (d, J=4.4 Hz, 2H), 4.232 (m, 2H), 6.800 (s, 1H), 7.058 (m, 1H), 7.160 (m, 1H), 7.287 (m, 1H), 7.400 (m, 2H), 7.545 (m, 1H), 7.964 (m, 2H), 8.200 (s, 1H), 8.342 (m, 1H); MS (m/e): 457.4 (M+1).

EXAMPLE 50

Compound 50: N-(2-(diethylamino)ethyl)-2-(3-(3-(imidazo[1,2-b]pyridazin-2-yl)phenyl)-1,2,4-oxadiazol-5-yl)acetamide was prepared in a manner similar to that described in Example 1.
$^1$H NMR (DMSO-d$_6$, 400 MHz): δ 1.007 (m, 6H), 1.244 (m, 2H), 2.607 (m, 4H), 3.241 (m, 2H), 4.086 (s, 2H), 7.280 (dd, 1H, J=8 Hz, J=8.4 Hz), 7.674 (t, 1H, J=8 Hz), 7.984 (d, 1H, J=8 Hz), 8.177 (d, 1H, J=8.4 Hz), 8.263 (d, 1H, J=8 Hz), 8.540 (dd, 1H, J$_1$=J$_2$=8 Hz), 8.742 (s, 1H), 9.014 (s,1H); MS (m/e): 420.3 (M+1).

EXAMPLE 51

Compound 51: N-butyl-2-(3-(3-(imidazo[1,2-b]pyridazin-2-yl)phenyl)-1,2,4-oxadiazol-5-yl)acetamide was prepared in a manner similar to that described in Example 1.
$^1$H NMR (DMSO-d$_6$, 400 MHz): δ 0.898 (t, 3H, J=7.2 Hz), 1.338 (m, 2H), 1.443 (m, 2H), 3.125 (m, 2H), 4.050 (s, 2H), 7.280 (dd, 1H, J=8 Hz, J=8.4 Hz), 7.674 (t, 1H, J=8 Hz), 7.984 (d, 1H, J=8 Hz), 8.177 (d, 1H, J=8.4 Hz), 8.263 (d, 1H, J=8 Hz), 8.540 (dd, 1H, J$_1$=J$_2$=8 Hz), 8.742 (s, 1H), 9.014 (s,1H); MS (m/e): 377.3 (M+1).

EXAMPLE 52

Compound 52: 2-(3-(3-(imidazo[1,2-b]pyridazin-2-yl)phenyl)-1,2,4-oxadiazol-5-yl)-N-(((S)-tetrahydrofuran-2-yl)methyl)acetamide was prepared in a manner similar to that described in Example 1.
$^1$H NMR (DMSO-d$_6$, 400 MHz): δ 1.844 (m, 4H, ), 3.209 (m, 3H), 3.651 (m, 2H), 4.105 (s, 2H), 7.279 (dd, 1H, J=8 Hz, J=8.4 Hz), 7.670 (t, 1H, J=8 Hz), 7.984 (d, 1H, J=8 Hz), 8.176 (d, 1H, J=8.4 Hz), 8.260 (d, 1H, J=8 Hz), 8.538 (dd, 1H, J$_1$=J$_2$=8 Hz), 8.741 (s, 1H), 9.011 (s,1H); MS (m/e): 350.2 (M+1).

EXAMPLE 53

Compound 53: N-cyclopentyl-2-(3-(3-(imidazo[1,2-b]pyridazin-2-yl)phenyl)-1,2,4-oxadiazol-5-yl)acetamide was prepared in a manner similar to that described in Example 1.
$^1$H NMR (DMSO-d$_6$, 400 MHz): δ 1.491 (m, 4H), 1.658 (m, 2H), 1.821 (m, 2H), 4.031 (m, 1H), 4.067 (s, 2H), 7.279 (dd, 1H, J=8 Hz, J=8.4 Hz), 7.669 (t, 1H, J=8 Hz), 7.983 (d, 1H, J=8 Hz), 8.186 (d, 1H, J=8.4 Hz), 8.263 (d, 1H, J=8 Hz), 8.540 (dd, 1H, J$_1$=J$_2$=8 Hz), 8.731 (s, 1H), 9.018 (s,1H); MS (m/e): 389.3 (M+1).

EXAMPLE 54

Compound 54: 2-(3-(3-(imidazo[1,2-b]pyridazin-2-yl)phenyl)-1,2,4-oxadiazol-5-yl)-N-(2-methoxyethyl)acetamide was prepared in a manner similar to that described in Example 1.
$^1$H NMR (CDCl$_3$, 400 MHz): δ 3.423 (s, 3H), 3.572 (m, 4H), 4.020 (s, 2H), 7.100 (dd, 1H, J=8 Hz, J=8.4 Hz), 7.629 (t, 1H, J=8 Hz), 8.004 (d, 1H, J=8 Hz), 8.110 (d, 1H, J=8.4 Hz), 379.2 (M+1).

EXAMPLE 55

Compound 55: 2-(3-(3-(imidazo[1,2-b]pyridazin-2-yl)phenyl)-1,2,4-oxadiazol-5-yl)-1-morpholinoethanone was prepared in a manner similar to that described in Example 1.
$^1$H NMR (DMSO-d$_d$, 400 MHz): δ 3.594 (m, 8H), 4.443 (s, 2H), 7.266 (dd, 1H, J=8 Hz, J=8.4 Hz), 7.668 (t, 1H, J=8 Hz), 7.979 (d, 1H, J=8 Hz), 8.170 (d, 1H, J=8.4 Hz), 8.254 (d, 1H, J=8 Hz), 8.526 (dd, 1H, J$_1$=J$_2$=8 Hz), 8.736 (s, 1H), 8.991 (s, 1H); MS (m/e): 391.4 (M+1).

EXAMPLE 56

Compound 56: N-cyclopropyl-2-(3-(3-(imidazo[1,2-b]pyridazin-2-yl)phenyl)-1,2,4-oxadiazol-5-yl)acetamide was prepared in a manner similar to that described in Example 1.
$^1$H NMR (DMSO-dd, 400 MHz): δ 0.631 (m, 2H), 0.864 (m, 2H), 2.820 (m, 1H), 3.986 (s, 2H), 7.100 (dd, 1H, J=8 Hz, J=8.4 Hz), 7.636 (t, 1H, J=8 Hz), 8.014 (d, 1H, J=8 Hz), 8.077 (d, 1H, J=8.4 Hz), 8.213 (d, 1H, J=8 Hz), 8.351 (dd, 1H, J$_1$=J$_2$=8 Hz), 8.396 (s, 1H), 8.680 (s,1H); MS (m/e): 361.2 (M+1).

EXAMPLE 57

Compound 57: 3-(3-(imidazo[1,2-b]pyridazin-2-yl)phenyl)-N-(2-morpholinoethyl)-1,2,4-oxadiazole-5-carboxamide was prepared in a manner similar to that described in Example 1.
$^1$H NMR (CD$_3$Cl$_3$, 400 MHz): δ 8.769 (t, J=1.6 Hz, 1H), 8.406 (s, 1H), 8.354 (dd, J=1.6-4.4 Hz, 1H), 8.199 (dt, J=1.2-7.6 Hz, 1H), 8.143 (dt, J=1.2-7.6 Hz, 1H), 8.016 (m,1H), 7.644 (t, J=8 Hz, 1H), 7.099 (dd, J=4.4 Hz, 1H), 3.811 (t, J=4.4 Hz,4H), 3.656 (dd, J=6-12 Hz,2H), 2.682 (t, J=6 Hz,2H), 2.577 (m,4H); MS (m/e): 420 (M+1).

EXAMPLE 58

Compound 58: N-ethyl-3-(3-(imidazo[1,2-b]pyridazin-2-yl)phenyl)-1,2,4-oxadiazole-5-carboxamide was prepared in a manner similar to that described in Example 1.

$^1$H NMR (DMSO-d$_6$, 400 MHz): δ 9.020(d, J=0.8 Hz, 1H), 8.820(dd, J=1.2, 1.6 Hz, 1H), 8.550(dd, J=1.6, 4.8 Hz, 1H), 8.300(m, 1H), 8.186(m, 1H), 8.063(m, 1H), 7.712(m, 1H), 7.290(dd, J=4.8, 9.6 Hz, 1H), 3.323(m, 2H), 1.180(t, J=7.2 Hz, 3H); MS (m/e): 335.3 (M+1).

EXAMPLE 59

Compound 59: N-cyclopentyl-3-(3-(imidazo[1,2-b]pyridazin-2-yl)phenyl)-1,2,4-oxadiazole-5-carboxamide was prepared in a manner similar to that described in Example 1.

$^1$H NMR (CDCl$_3$, 400 MHz): δ 8.737(s, 1H), 8.409(s, 1H), 8.350(d, J=4.4 Hz, 1H), 8.180(d, J=8.4 Hz, 1H), 8.136(d, J=7.2 Hz, 1H), 8.016(d, J=8.8 Hz, 1H), 7.626(t, J=8.0 Hz, 1H), 7.098(dd, J=4.4, 9.6 Hz, 1H), 1.802(m, 2H), 1.674(m, 6H); MS (m/e): 375.4 (M+1).

EXAMPLE 60

Compound 60: (3-(3-(imidazo[1,2-b]pyridazin-2-yl)phenyl)-1,2,4-oxadiazol-5-yl)(morpholino)methanone was prepared in a manner similar to that described in Example 1.

$^1$H NMR (CDCl$_3$, 400 MHz): δ 8.717(t, J=1.6 Hz, 1H), 8.400(s, 1H), 8.347(dd, J=1.6, 4.4 Hz, 1H), 8.228(m, 1H), 8.136(m, 1H), 7.996(m, 1H), 7.639(t, J=7.6 Hz, 1H), 7.096 (dd, J=4.4, 9.2 Hz, 1H), 3.983(m, 2H), 3.899(m, 4H), 3.828 (m, 2H); MS (m/e): 377.3 (M+1).

EXAMPLE 61

Compound 61: 3-(3-(imidazo[1,2-b]pyridazin-2-yl)phenyl)-N-(2-methoxyethyl)-1,2,4-oxadiazole-5-carboxamide was prepared in a manner similar to that described in Example 1.

$^1$H NMR (CDCl$_3$, 400 MHz): δ 8.746(t, J=1.6 Hz, 1H), 8.420(s, 1H), 8.355(dd, J=1.6, 4.4 Hz, 1H), 8.189(m, 1H), 8.154(m, 1H), 8.021(dd, J=1.6, 9.2 Hz, 1H), 7.639(t, J=8.0 Hz, 1H), 7.107(dd, J=4.8, 9.6 Hz, 1H), 3.747(dd, J=4.8, 10.4 Hz, 2H), 3.639(t, J=5.6 Hz, 2H), 3.467(s, 3H); MS (m/e): 365.3 (M+1).

EXAMPLE 62

Compound 62: N-(2-(dimethylamino)ethyl)-3-(3-(imidazo[1,2-b]pyridazin-2-yl)phenyl)-1,2,4-oxadiazole-5-carboxamide was prepared in a manner similar to that described in Example 1.

$^1$H NMR (CD$_3$OD, 400 MHz): δ 8.774(s, 1H), 8.665(s, 1H), 8.478(dd, J=2.0, 4.8 Hz, 1H), 8.218(d, J=8.0 Hz, 1H), 8.155(d, J=8.0 Hz, 1H), 8.058(m, 1H), 7.676(t, J=8.0 Hz, 1H), 7.280(dd, J=4.0, 8.8 Hz, 1H), 3.666(t, J=6.4 Hz, 2H), 2.790(t, J=6.4 Hz, 2H), 2.472(s, 6H); MS (m/e): 378.4 (M+1).

EXAMPLE 63

Compound 63: (4-ethylpiperazin-1-yl)(3-(3-(imidazo[1,2-b]pyridazin-2-yl)phenyl)-1,2,4-oxadiazol-5-yl)methanone was prepared in a manner similar to that described in Example 1.

$^1$H NMR (DMSO-d$_6$, 400 MHz): δ 9.034(s ,1H), 8.757(t, J=1.6 Hz, 1H), 8.549(dd, J=1.6, 4.8 Hz, 1H), 8.315(m, 1H), 8.157(m, 1H), 8.046(m, 1H), 7.712(t, J=8.0 Hz, 1H), 7.290 (dd, J=4.4, 8.8 Hz, 1H), 3.741(m, 4H), 2.487(m, 4H), 2.398 (dd, J=7.2, 14 Hz, 2H), 2.091(s, 3H); MS (m/e): 404.4 (M+1).

EXAMPLE 64

Compound 64: 3-(3-(imidazo[1,2-b]pyridazin-2-yl)phenyl)-N-(thiophen-2-ylmethyl)-1,2,4-oxadiazole-5-carboxamide was prepared in a manner similar to that described in Example 1.

$^1$H NMR (CDCl$_3$, 400 MHz): δ 8.703(s, 1H), 8.388(s, 1H), 8.344(m, 1H), 8.186(d, J=8.0 Hz, 1H), 8.113(d, J=8.0 Hz, 1H), 8.007(d, J=8.4 Hz, 1H), 7.611(t, J=8.0 Hz, 1H), 7.336(d, J=5.6 Hz, 1H), 7.154(d, J=3.6 Hz, 1H), 7.084(dd, J=4.4, 8.8 Hz, 1H), 7.040(dd, J=3.6, 5.2 Hz, 1H), 4.914(d, J=5.2 Hz, 2H); MS (m/e): 403.4 (M+1).

EXAMPLE 65

Compound 65: N-(2-hydroxyethyl)-3-(3-(imidazo[1,2-b]pyridazin-2-yl)phenyl)-1,2,4-oxadiazole-5-carboxamide was prepared in a manner similar to that described in Example 1.

$^1$H NMR (DMSO-d$_6$, 400 MHz): δ 9.034(s, 1H), 8.757(s, 1H), 8.549(s, 1H), 8.315(s, 1H), 8.157(s, 1H), 8.046(s, 1H), 7.712(s, 1H), 7.290(s, 1H), 3.625(m, 2H), 3.380(m, 2H); MS (m/e): 351.3 (M+1).

EXAMPLE 66

Compound 66: 3-(3-(imidazo[1,2-b]pyridazin-2-yl)phenyl)-N,N-dimethyl-1,2,4-oxadiazole-5-carboxamide was prepared in a manner similar to that described in Example 1.

$^1$H NMR (DMSO-d$_6$, 400 MHz): δ 9.100(s, 1H), 8.757(s, 1H), 8.549(s, 1H), 8.315(s, 1H), 8.157(s, 1H), 8.046(s, 1H), 7.712(s, 1H), 7.290(s, 1H), 3.100(s, 3H), 3.281(s, 3H); MS (m/e): 335.3 (M+1).

EXAMPLE 67

Compound 67: (3-(3-(imidazo[1,2-b]pyridazin-2-yl)phenyl)-1,2,4-oxadiazol-5-yl)(pyrrolidin-1-yl)methanone was prepared in a manner similar to that described in Example 1.

$^1$H NMR (DMSO-d$_6$, 400 MHz): δ 9.034(s, 1H), 8.757(s, 1H), 8.549(s, 1H), 8.315(s, 1H), 8.157(s, 1H), 8.046(s, 1H), 7.712(s, 1H), 7.290(s, 1H), 3.952(m, 2H), 3.590(m, 2H), 1.967(m, 4H); MS (m/e): 361.1 (M+1).

EXAMPLE 68

Compound 68: 3-(3-(imidazo[1,2-b]pyridazin-2-yl)phenyl)-N-methyl-1,2,4-oxadiazole-5-carboxamide was prepared in a manner similar to that described in Example $^1$H NMR (DMSO-d$_6$, 400 MHz): δ 9.034(s, 1H), 8.757(s, 1H), 8.549(s, 1H), 8.315(s, 1H), 8.157(s, 1H), 8.046(s, 1H), 7.712(s, 1H), 7.290(s, 1H), 2.875(s, 3H); MS (m/e): 321.3 (M+1).

EXAMPLE 69

Compound 69: 2-(3-(imidazo[1,2-b]pyridazin-2-yl)phenylamino)nicotinamide was prepared as outlined and described below.

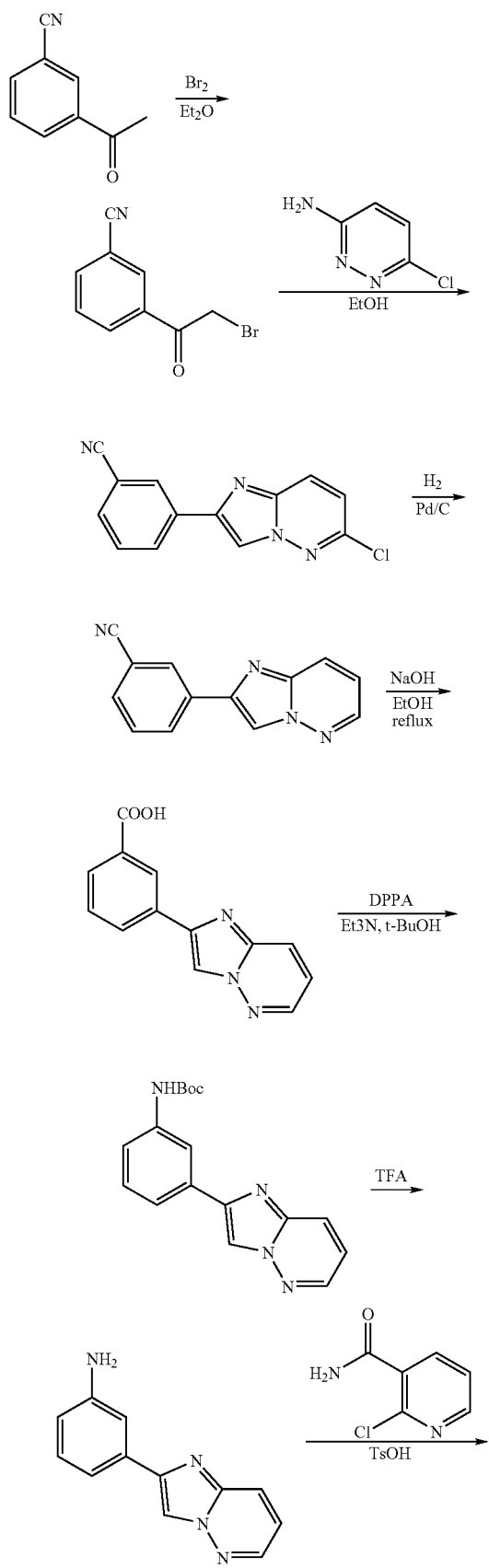

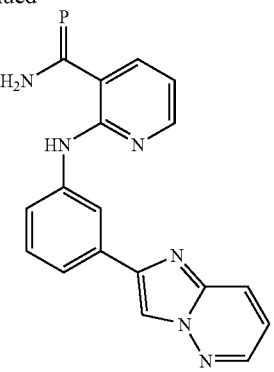

Br$_2$ (1 mmol) was dropwise added to a solution of 3-acetylbenzonitrile (1 mmol) in Et$_2$O (15 ml) at 0° C., and then the mixture was stirred at r.t. for 4 h. Water was added, and the mixture was extracted with EtOAc. The organic layer was dried over Na$_2$SO$_4$, and was concentrated to give an oil, i.e., 3-(2-bromoacetyl)benzonitrile, which was directly used for the next step without purification.

A solution of 3-(2-bromoacetyl)benzonitrile and 6-chloropyridazin-3-amine (1 mmol) in EtOH was heated to reflux overnight. Then the mixture was cooled to r.t., and the precipitate was filtered to give 3-(6-chloroimidazo[1,2-b]pyridazin-2-yl)benzonitrile with a yield of 52.8%.

A mixture of 3-(6-chloroimidazo[1,2-b]pyridazin-2-yl) benzonitrile (1 mmol) and Pd/C (20 mg) in DMF/THF (10 ml/10 ml) was stirred at r.t. for 6 h equipped with a H$_2$ balloon. Then the solvent was removed under reduced pressure and 3-(imidazo[1,2-b]pyridazin-2-yl)benzonitrile was obtained with a yield of 88.5%.

A solution of 3-(imidazo[1,2-b]pyridazin-2-yl)benzonitrile (1 mmol) and 6M NaOH (2 ml) in EtOH was heated to reflux for 2 h. Then the mixture was diluted with water and acidified with HCl. The precipitate was filtered to give 3-(imidazo[1,2-b]pyridazin-2-yl)benzoic acid with a yield of 60%.

A solution of 3-(imidazo[1,2-b]pyridazin-2-yl)benzoic acid (1 mmol), DPPA (3 mmol) and Et$_3$N (3 mmol) in toluene was heated to reflux for 4 h. Then t-BuOH (1 ml) was added and reflux was continued overnight. Water was added, and the mixture was extracted with EtOAc. The organic layer was washed with diluted HCl, brine and NaHCO$_3$ (aq), and was concentrated to give a solid. After purification by chromatography, tert-butyl 3-(imidazo[1,2-b]pyridazin-2-yl)phenylcarbamate was obtained with a yield of 38.5%.

A solution of tert-butyl 3-(imidazo[1,2-b]pyridazin-2-yl) phenylcarbamate (1 mmol) and TFA (4 mmol) in CH$_2$Cl$_2$ (10 ml) was stirred at 35° C. overnight. Then 1 M NaOH (4 ml) was added, and the mixture was extracted with EtOAc. The organic layer was concentrated to give 3-(imidazo[1,2-b]pyridazin-2-yl)aniline with a yield of 75%.

A solution of 3-(imidazo[1,2-b]pyridazin-2-yl)aniline (1 mmol) and 2-chloronicotinamide (1.2 mmol) in C$_4$H$_9$OH was added TsOH (1.2 mmol). The mixture was stirred at 160° C. overnight. Then water was added, and the reaction solution was extracted with EtOAc. The organic layer was washed with brine and solvent was removed. 2-(3-(imidazo[1,2-b] pyridazin-2-yl)phenylamino)nicotinamide was purified by TLC with a yield of 31%.

$^1$H NMR (DMSO, 400 MHz): δ 11.287(s, 1H), 8.854(s, 1H), 8.506(dd, J=2, 4.4 Hz, 1H), 8.363(dd, J=1.6, 4.8 Hz, 1H), 8.227(t, J=2 Hz, 1H), 8.163(m, 2H), 7.859(dd, J=1.2, 4

Hz, 1H), 7.650(d, J=8.0 Hz, 1H), 7.394(t, J=8.0 Hz, 1H), 7.242(dd, J=4.4, 9.2 Hz, 1H), 6.871(dd, J=4.8, 8.0 Hz, 1H); MS (m/e): 331.3 (M+1).

EXAMPLE 70

Compound 70: (2-(3-(imidazo[1,2-b]pyridazin-2-yl)phenylamino)pyridin-3-yl)(pyrrolidin-1-yl)methanone was prepared in a manner similar to that described in Example 69.

$^1$H NMR (CD$_3$OD, 400 MHz): δ 8.544 (s, 1H), 8.264(m, 1H), 8.146(s, 1H), 8.029(d, J=9.2 Hz, 1H), 7.765(m, 1H), 7.663(d, J=6.8 Hz, 1H), 7.572(m, 1H), 7.418(t, J=8 Hz, 1H), 7.263(dd, J=4.8, 8.8 Hz, 1H), 6.944(s, 1H), 6.907(dd, J=5.2, 7.6 Hz, 1H), 3.619(m,2H), 3.552(m, 2H), 1.952(m, 4H); MS (m/e): 385.4 (M+1).

EXAMPLE 71

Compound 71: N-(2-hydroxyethyl)-2-(3-(imidazo[1,2-b]pyridazin-2-yl)phenylamino)nicotinamide was prepared in a manner similar to that described in Example 69.

$^1$H NMR (CD$_3$OD, 400 MHz): δ 8.541(s, 1H), 8.447(dd, J=1.2, 4.4 Hz, 1H), 8.318(m, 2H), 8.056(dd, J=1.6, 7.6 Hz, 1H), 8.016(d, J=9.6 Hz, 1H), 8.687(dd, J=1.6, 8.0 Hz, 1H), 7.640(d, J=7.6 Hz, 1H), 7.422(t, J=8.0 Hz, 1H), 7.253(dd, J=4.4, 9.2 Hz, 1H), 6.943(s,1H), 6.851(dd, J=4.4, 7.6 Hz, 1H), 3.764(t, J=6 Hz, 2H), 3.554(t, J=6 Hz, 2H); MS (m/e): 375.4 (M+1).

EXAMPLE 72

Compound 72: ethyl 2-(3-(imidazo[1,2-b]pyridazin-2-yl)phenylamino)nicotinate was prepared in a manner similar to that described in Example 69.

$^1$H NMR (DMSO, 400 MHz): δ 10.261(s, 1H), 8.872(d, J=4 Hz, 1H), 8.484(m, 2H), 8.307(m, 2H), 8.149(d, J=9.2 Hz, 1H), 7.864(d, J=8.0 Hz, 1H), 7.728(d, J=8.0 Hz, 1H), 7.430(t, J=8.4 Hz, 1H), 7.248(dd, J=4.8, 9.2 Hz, 1H), 6.937(dd, J=4.4, 8.0 Hz, 1H), 4.414(m, 2H), 1.384(t, J=6.8 Hz, 3H); MS (m/e): 360.3 (M+1).

EXAMPLE 73

Compound 73: N-cyclopropyl-2-(3-(imidazo[1,2-b]pyridazin-2-yl)phenylamino)nicotinamide was prepared in a manner similar to that described in Example 69.

$^1$H NMR (CD$_3$OD, 400 MHz): δ 8.545(s, 1H), 8.456(d, J=4.4 Hz, 1H), 8.322(m, 2H), 8.030(dd, J=0.8, 8.8 Hz, 1H), 7.981(m, 1H), 7.667(m, 2H), 7.429(t, J=8.0 Hz, 1H), 7.248 (m, 1H), 6.943(s, 1H), 6.826(m, 1H), 2.892(m, 1H), 0.901(m, 2H), 0.682(m, 2H); MS (m/e): 371.4 (M+1).

EXAMPLE 74

Compound 74: (2-(3-(imidazo[1,2-b]pyridazin-2-yl)phenylamino)pyridin-3-yl)(morpholino)methanone was prepared in a manner similar to that described in Example 69.

$^1$H NMR (CD$_3$OD, 400 MHz): δ 8.539(s, 1H), 8.452(dd, J=1.6, 4.4 Hz, 1H), 8.273(dd, J=2, 4.8 Hz, 1H), 8.112(m, 1H), 8.024(m, 1H), 7.666(m, 2H), 7.555(m, 1H), 7.420(t, J=8.4 Hz, 1H), 7.263(dd, J=4.4, 9.2 Hz, 1H), 6.937(m, 2H), 3.704 (m, 4H), 3.633(m, 4H); MS (m/e): 401.4 (M+1).

EXAMPLE 75

Compound 75: N-(3-(imidazo[1,2-b]pyridazin-2-yl)-5-(5-(morpholinomethyl)-1,2,4-oxadiazol-3-yl)phenyl)methanesulfonamide was prepared as outlined and described below.

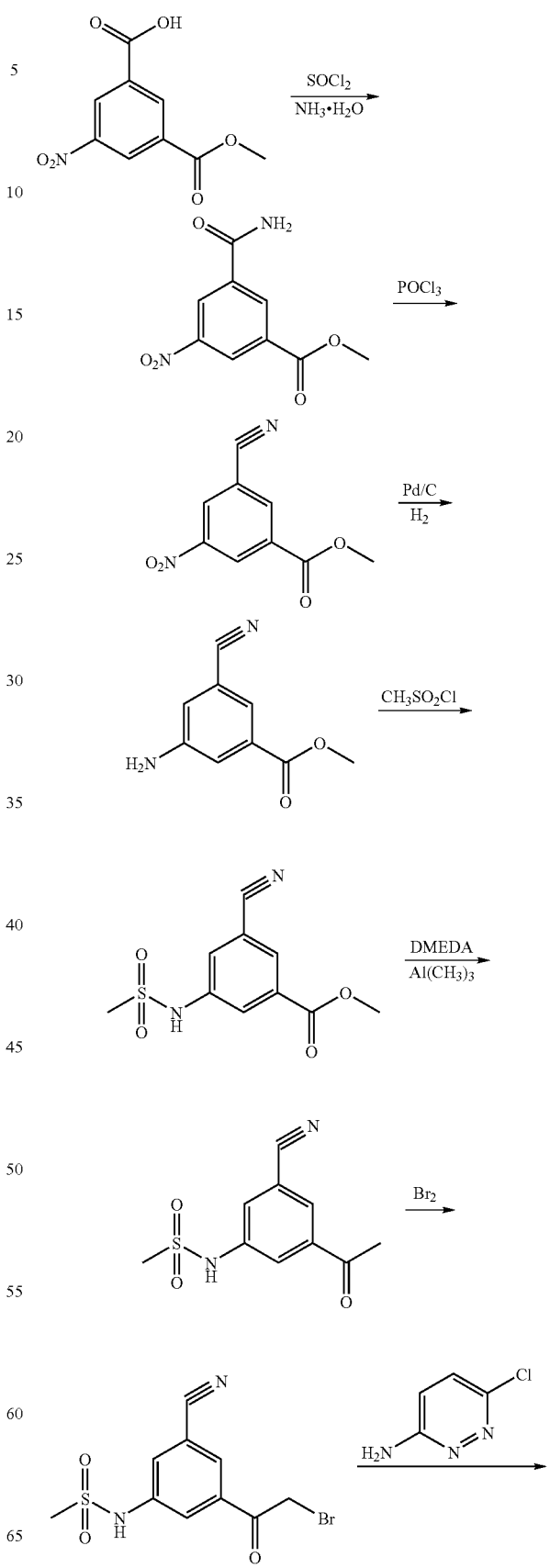

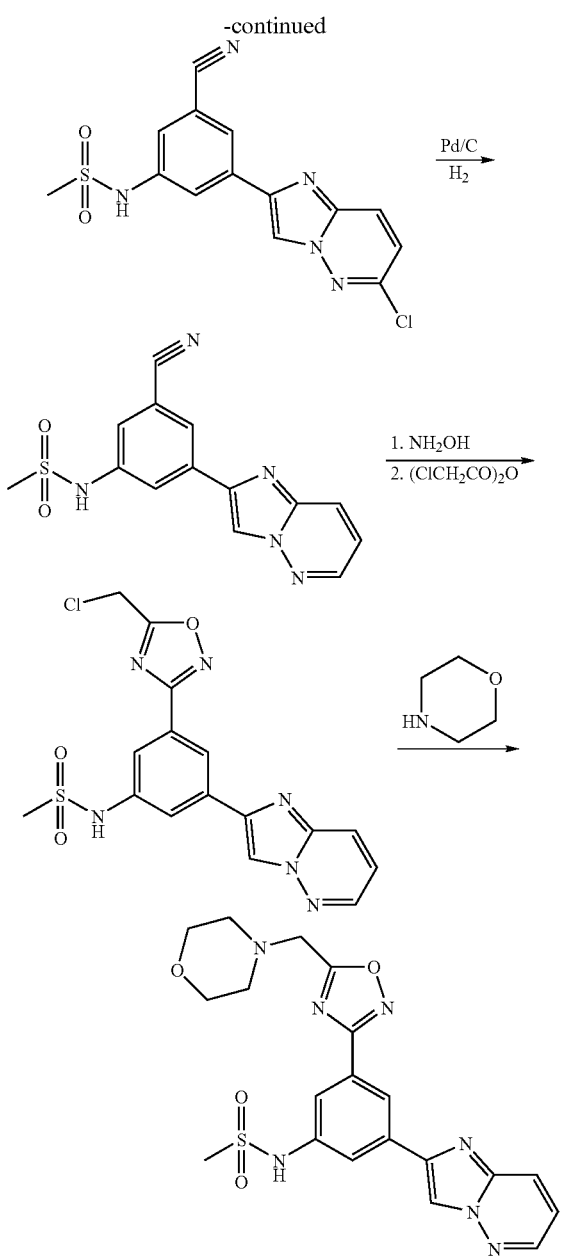

A mixture of 3-methoxycarbonyl-5-nitrobenzoic acid (44 mmol), SOCl$_2$ (40 mL) and DMF (1 mL) was heated to reflux for 2 hours. Then the excessive SOCl$_2$ was removed under reduced pressure. The residue was dissolved in DCM (80 mL), and added with NH3.H2O (15 mL) dropwise after cooling by ice-water. After addition, it was continued to stir 5 min. The resulting mixture was filtrated to give methyl-3-carbamoyl-5-nitrobenzoate in 85% yield.

POCl$_3$ (33 mmol) was added to the solution of methyl-3-carbamoyl-5-nitrobenzoate (30 mmol) in 1,2-dichloroethane (100 mL). Then the solution was heated to reflux for 3 hours. After cooling, it was poured into water. The organic layer was washed with saturated NaHCO$_3$ solution and brine sequentially, dried over anhydrous Na$_2$SO$_4$, and concentrated to give methyl-3-cyano-5-nitrobenoate in 90% yield. 10% Pd/C (0.9 g) was added to the solution of methyl-3-cyano-5-nitrobenoate (25 mmol) in MeOH (200 mL) and THF (100 mL). Then the solution was stirred at room temperature for 4 hours. After filtration, it was concentrated to give methyl-3-amine-5-cyanobenoate in 95% yield.

CH$_3$SO$_2$Cl (40 mmol) was added to the solution of methyl-3-amine-5-cyanobenoate (10 mmol), pryridine (50 mmol) and DMAP (1 mmol) in DCM (150 mL). The solution was then heated to reflux for 4 hours. After cooling, diluted hydrochloric acid was poured into the solution. The organic layer was washed with water and brine sequentially, dried over anhydrous Na$_2$SO$_4$, and concentrated. The crude product was purified by column chromatography to afford methyl-3-cyano-5-(methylsulfonamido)benoate in 70% yield.

Al(CH$_3$)$_3$ (20 mmol) was added dropwise to the ice-water cooled solution of DMEDA (4.4 mmol) in dry toluene (60 mL) under nitrogen. After addition, it was continued to stir for 2 hours at room temperature. Then, methyl-3-cyano-5-(methylsulfonamido)benzoate (4 mmol) was added, and the reaction mixture was heated to reflux overnight. After cooling, it was poured into diluted hydrochloric acid, the mixture was extracted with EtOAc, the combined organic layer was washed with water and brine sequentially, dried over anhydrous Na$_2$SO$_4$, and concentrated to afford N-(3-acetyl-5-cyanophenyl)methanesulfonamide with a yield of 35%. Br$_2$ (1.2 mmol) was added dropwise to the solution of N-(3-acetyl-5-cyanophenyl)methanesulfonamide (1 mmol) in Et$_2$O (50 mL). After addition, it was continued to stir for 1.5 hours. Then the reaction mixture was washed with water and brine sequentially, dried over anhydrous Na$_2$SO$_4$, and concentrated to afford N-(3-(2-bromoacetyl)-5-cyanophenyl)methanesulfonamide with a yield of 85%.

A mixture of N-(3-(2-bromoacetyl)-5-cyanophenyl)methanesulfonamide (0.8 mmol) and 6-chloropyridazin-3-amine (0.8 mmol) in EtOH (8 mL) was refluxed for 4 hours. After cooling, the resulting mixture was filtrated to give N-(3-(6-chloroimidazo[1,2-b]pyridazin-2-yl)-5-cyanophenyl)methanesulfonamide in 50% yield. 10% Pd/C (20 mg) was added to the solution of N-(3-(6-chloroimidazo[1,2-b]pyridazin-2-yl)-5-cyanophenyl)methanesulfonamide (0.3 mmol) in THF (25 mL). Then it was stirred at room temperature for 4 hours. After filtration, it was concentrated to give N-(3-cyano-5-(imidazo[1,2-b]pyridazin-2-yl)phenyl)methanesulfonamide in 95% yield.

A mixture of N-(3-cyano-5-(imidazo[1,2-b]pyridazin-2-yl)phenyl)methanesulfonamide (0.25 mmol), hydroxylamine hydrochloride (0.75 mmol) and triethylamine (1 mmol) in EtOH (12 mL) was refluxed for 4 hours. After removal of the solvent in vacuo, the residue was dissolved in THF (12 mL), added with (ClCH$_2$CO)$_2$O (0.75 mmol) and triethylamine (1 mmol), and stirred at room temperature for 1 hours. Then it was heated to reflux for another 8 hours. After removal of the solvent in vacuo and addition of water, the mixture was extracted with EtOAc. The combined organic layer was washed with water and brine sequentially, dried over anhydrous Na$_2$SO$_4$ and concentrated. The resulting residue was purified by column chromatography to give N-(3-(5-(chloromethyl)-1,2,4-oxadiazol-3-yl)-5-(imidazo[1,2-b]pyridazin-2-yl)phenyl)methanesulfonamide in 90% yield.

A mixture of N-(3-(5-(chloromethyl)-1,2,4-oxadiazol-3-yl)-5-(imidazo[1,2-b]pyridazin-2-yl)phenyl)methanesulfonamide (0.1 mmol), morpholine (0.4 mmol) and K$_2$CO$_3$ (0.2 mmol) in DMF (2 mL) was stirred at 80° C. for 1.5 hours. After cooling, it was poured into water, and extracted with CH$_2$Cl$_2$. The combined organic layer was washed with brine, dried over anhydrous Na$_2$SO$_4$ and concentrated. The resulting residue was purified by column chromatography to give the title product in 60% yield.

¹H NMR (DMSO, 400 MHz): δ 8.933 (s, 1H), 8.547 (d, J=4.4 Hz, 1H), 8.334 (s, 1H), 8.204 (d, J=10.0 Hz, 1H), 8.075 (s, 1H), 7.862 (s, 1H), 7.295 (dd, J₁=9.2 Hz, J₂=4.4 Hz, 1H), 4.015 (s, 2H), 3.634 (t, J=4.4 Hz, 4H), 3.043 (s, 3H), 2.591 (t, J=4.4 Hz, 4H); MS (m/e): 456.3 (M+1).

EXAMPLE 76

Compound 76: N-(3-(imidazo[1,2-b]pyridazin-2-yl)-5-(5-(piperidin-1-ylmethyl)-1,2,4-oxadiazol-3-yl)phenyl)methanesulfonamide was prepared in a manner similar to that described in Example 75.
¹H NMR (DMSO, 400 MHz): δ 8.959 (s, 1H), 8.551 (m, 1H), 8.386 (s, 1H), 8.207 (d, J=9.2 Hz, 1H), 8.125 (s, 1H), 7.888 (s, 1H), 7.302 (dd, J₁=9.6 Hz, J₂=4.8 Hz, 1H), 3.958 (s, 2H), 3.089 (s, 3H), 2.528 (m, 4H), 1.555 (m, 4H), 1.393 (m, 2H); MS (m/e): 454.3 (M+1).

EXAMPLE 77

Compound 77: N-(3-(imidazo[1,2-b]pyridazin-2-yl)-5-(5-((2-methoxyethylamino)methyl)-1,2,4-oxadiazol-3-yl)phenyl)methanesulfonamide was prepared in a manner similar to that described in Example 75.
¹H NMR (DMSO, 400 MHz): δ 10.178 (s, 1H), 9.002 (s, 1H), 8.587 (m, 1H), 8.451 (s, 1H), 8.246 (d, J=9.2 Hz, 1H), 8.163 (s, 1H), 7.930 (s, 1H), 7.341 (dd, J₁=9.2 Hz, J₂=4.4 Hz, 1H), 4.192 (s, 2H), 3.491 (t, J=5.6 Hz, 2H), 3.295 (s, 3H), 3.142 (s, 3H), 2.866 (t, J=5.6 Hz, 2H); MS (m/e): 444.3 (M+1).

EXAMPLE 78

Compound 78: N-(3-(5-((2-(dimethylamino)ethylamino)methyl)-1,2,4-oxadiazol-3-yl)-5-(imidazo[1,2-b]pyridazin-2-yl)phenyl)methanesulfonamide was prepared in a manner similar to that described in Example 75.
¹H NMR (DMSO, 400 MHz): δ 8.971 (s, 1H), 8.557 (m, 1H), 8.416 (s, 1H), 8.211 (d, J=9.2 Hz, 1H), 8.117 (s, 1H), 7.898 (s, 1H), 7.308 (dd, J₁=9.2 Hz, J₂=5.2 Hz, 1H), 4.175 (s, 2H), 3.107 (s, 3H), 2.855 (m, 2H), 2.789 (m, 2H), 2.488 (s, 6H); MS (m/e): 457.3 (M+1).

EXAMPLE 79

Compound 79: N-(3-(imidazo[1,2-b]pyridazin-2-yl)-5-(5-(piperazin-1-ylmethyl)-1,2,4-oxadiazol-3-yl)phenyl)methanesulfonamide was prepared in a manner similar to that described in Example 75.
¹H NMR (DMSO, 400 MHz): δ 8.949 (s, 1H), 8.547 (m, 1H), 8.337 (s, 1H), 8.203 (d, J=8.8 Hz, 1H), 8.100 (s, 1H), 7.875 (s, 1H), 7.297 (dd, J₁=8.8 Hz, J₂=4.4 Hz, 1H), 3.973 (s, 2H), 3.080 (s, 3H), 2.760 (m, 4H), 2.511 (m, 4H); MS (m/e): 455.3 (M+1).

EXAMPLE 80

Compound 80: N-(3-(5-(aminomethyl)-1,2,4-oxadiazol-3-yl)-5-(imidazo[1,2-b]pyridazin-2-yl)phenyl)methanesulfonamide was prepared in a manner similar to that described in Example 75.
¹H NMR (CD₃OD, 400 MHz): δ 8.540 (s, 1H), 8.382 (m, 1H), 8.351 (s, 1H), 7.956 (d, J=9.2 Hz, 1H), 7.908 (m, 2H), 7.203 (dd, J₁=9.2 Hz, J₂=4.4 Hz, 1H), 4.124 (s, 2H), 3.007 (s, 3H); MS (m/e): 386.3 (M+1)

EXAMPLE 81

Compound 81: 2-(3-(5-(piperazin-1-ylmethyl)-1,2,4-oxadiazol-3-yl)phenyl)imidazo[1,2-b]pyridazine was prepared in a manner similar to that described in Example 4.
¹H NMR (DMSO, 400 MHz): δ 9.211 (s, 1H), 8.777 (s, 1H), 8.695-8.710 (m, 1H), 8.313 (t, J=9.6 Hz, 1H), 8.082 (d, J=8.4 Hz, 1H), 7.740 (t, J=7.8 Hz, 1H), 7.457-7.491 (m, 1H), 4.433 (s, 1H), 3.244(bro s, 4H), 3.164(bro s, 4H); MS (m/e): 362.3(M+1).

EXAMPLE 82

Compound 82: N1-((3-(3-(imidazo[1,2-b]pyridazin-2-yl)phenyl)-1,2,4-oxadiazol-5-yl)methyl)ethane-1,2-diamine was prepared in a manner similar to that described in Example 4.
¹H NMR (CD₃OD, 400 MHz): δ 8.749 (t, J=1.8 Hz, 1H), 8.705 (s, 1H), 8.514-8.529 (m, 1H), 8.180-8.206 (m, 1H), 8.110-8.137 (m, 1H), 8.071-8.100 (m, 1H), 7.678 (t, J=7.8 Hz, 1H), 7.324-7.358 (m, 1H), 4.369 (s,2H), 3.191 (bro s, 2H), 1.306 (bro s, 2H); MS (m/e): 336.2 (M+1).

EXAMPLE 83

Compound 83: N1-((3-(3-(imidazo[1,2-b]pyridazin-2-yl)phenyl)-1,2,4-oxadiazol-5-yl)methyl)-N2,N2-dimethylethane-1,2-diamine was prepared in a manner similar to that described in Example 4.
¹H NMR (CD₃OD, 400 MHz): δ 8.782 (t, J=1.6 Hz, 1H), 8.696 (s, 1H), 8.509-8.524 (m, 1H), 8.207-8.234 (m, 1H), 8.114-8.140 (m, 1H), 8.075-8.104 (m, 1H), 7.699 (t, J=7.8 Hz, 1H), 7.312-7.346 (m, 1H), 4.275 (s,2H), 3.307-3.339 (m, 2H), 3.164-3.192 (m, 2H), 2.983 (s, 6H); MS (m/e): 364.2 (M+1).

EXAMPLE 84

Compound 84: 2-(3-(5-(morpholinomethyl)-1,2,4-oxadiazol-3-yl)phenyl)imidazo[1,2-b]pyridazine was prepared in a manner similar to that described in Example 4.
¹H NMR (DMSO, 400 MHz): δ 8.686 (t, J=1.4 Hz, 1H), 8.397 (s, 1H), 8.320-8.335 (m, 1H), 8.192-8.219 (m, 1H), 8.097-8.124 (m, 1H), 7.977-8.002 (m, 1H), 7.607 (t, J=7.8 Hz, 1H),7.056-7.089 (m, 1H), 3.953 (s,2H), 3.801 (t, J=4.8 Hz, 1H), 2.705 (t, J=4.6 Hz, 1H); MS (m/e): 363.2 (M+1).

EXAMPLE 85

Compound 85: 2,2,2-trifluoro-N-((3-(3-(imidazo[1,2-b]pyridazin-2-yl)phenyl)-1,2,4-oxadiazol-5-yl)methyl)acetamide was prepared in a manner similar to that described in Example 4.
¹H NMR (DMSO, 400 MHz): δ 10.447 (bro s, 1H), 9.001 (s, 1H), 8.732 (t, J=1.6 Hz, 1H), 8.545-8.530(m, 1H), 8.282-8.256 (m, 1H), 8.202-8.174 (m, 1H), 8.000-7.974 (m, 1H), 7.682 (t, J=7.6 Hz, 1H),7.295-7.260 (m, 1H), 4.878 (d, J=4.0 Hz, 2H); MS (m/e): 389.2 (M+1).

EXAMPLE 86

Compound 86: ethyl 2-((3-(3-(imidazo[1,2-b]pyridazin-2-yl) phenyl)-1,2,4-oxadiazol-5-yl)methyl- amino)-2-oxoacetate was prepared in a manner similar to that described in Example 4.
¹H NMR (CDCl₃, 400 MHz): δ 8.654 (t, J=1.4 Hz, 1H), 8.386 (s, 1H), 8.332-8.317(m, 1H), 8.195-8.172 (m, 1H), 8.078-8.055 (m, 1H), 8.012-7.987 (m, 1H), 7.596 (t, J=7.8 Hz, 1H), 7.091-7.057 (m, 1H), 4.900 (d, J=6.0 Hz, 2H), 4.453-4.400 (m, 2H), 1.428 (t, J=7.0 Hz, 3H); MS (m/e): 393.2 (M+1).

EXAMPLE 87

Compound 87: N-((3-(3-(imidazo[1,2-b]pyridazin-2-yl)phenyl)-1,2,4-oxadiazol-5-yl)methyl)-2-methoxyacetamide was prepared in a manner similar to that described in Example 4.

$^1$H NMR (DMSO, 400 MHz): δ 8.995 (s, 1H), 8.727 (t, J=1.6 Hz, 1H), 8.543-8.528(m, 1H), 8.271-8.245 (m, 1H), 8.197-8.171 (m, 1H), 7.994-7.968 (m, 1H), 7.672 (t, J=7.8 Hz, 1H), 7.294-7.259 (m, 1H), 4.701 (d, J=6.0 Hz, 2H), 3.955 (s, 2H), 3.389 (s, 3H); MS (m/e): 365.2 (M+1).

EXAMPLE 88

Compound 88: N-((3-(3-(imidazo[1,2-b]pyridazin-2-yl)phenyl)-1,2,4-oxadiazol-5-yl)methyl)cyclopentanecarboxamide was prepared in a manner similar to that described in Example 4.

$^1$H NMR (CDCl$_3$, 400 MHz): δ 8.647 (t, J=1.4 Hz, 1H), 8.370 (s, 1H), 8.329-8.314(m, 1H), 8.177-8.150 (m, 1H), 8.065-8.040 (m, 1H), 8.006-7.980 (m, 1H), 7.585 (t, J=7.8 Hz, 1H), 7.089-7.055 (m, 1H), 6.548 (bro s, 1H), 4.809 (d, J=5.2 Hz, 2H), 2.771-2.690 (m, 1H), 1.973-1.592 (m, 8H); MS (m/e): 389.2 (M+1).

EXAMPLE 89

Compound 89: ethyl 3-((3-(3-(imidazo[1,2-b]pyridazin-2-yl) phenyl)-1,2,4-oxadiazol-5-yl)methyl- amino)-3-oxopropanoate was prepared in a manner similar to that described in Example 4.

$^1$H NMR (CDCl$_3$, 400 MHz): δ 8.654 (s, 1H), 8.390 (s, 1H), 8.337-8.322(m, 1H), 8.192 (d, J=7.6 Hz, 1H), 8.118 (bro s, 1H), 8.077 (d, J=8.0 Hz, 1H), 8.002 (d, J=9.6 Hz, 1H), 8.192 (t, J=7.8 Hz, 1H), 7.096-7.061 (m, 1H), 4.855 (d, J=5.6 Hz, 2H), 4.248-4.301 (m, 2H), 3.487 (s, 2H), 1.337 (t, J=7.2 Hz, 3H); MS (m/e): 407.2 (M+1).

EXAMPLE 90

Compound 90: N-((3-(3-(imidazo[1,2-b]pyridazin-2-yl)phenyl)-1,2,4-oxadiazol-5-yl)methyl)cyclopropanecarboxamide was prepared in a manner similar to that described in Example 4.

$^1$H NMR (CDCl$_3$, 400 MHz): δ 8.691 (s, 1H), 8.397 (s, 1H), 8.337 (d, J=4.4 Hz, 1H), 8.193 (d, J=7.6 Hz, 1H), 8.092 (d, J=8.0 Hz, 1H), 8.008 (d, J=9.2 Hz, 1H), 7.610 (t, J=8.0 Hz, 1H), 7.101-7.067 (m, 1H), 4.849 (d, J=5.6 Hz, 2H), 1.608-1.557 (m, 1H), 1.113-1.075 (m, 2H), 0.897-0.849 (m, 2H); MS (m/e):361.2 (M+1).

EXAMPLE 91

Compound 91: N-((3-(3-(imidazo[1,2-b]pyridazin-2-yl)phenyl)-1,2,4-oxadiazol-5-yl)methyl)isobutyramide was prepared in a manner similar to that described in Example 4.

$^1$H NMR (CDCl$_3$, 400 MHz): δ 8.653 (t, J=1.6 Hz, 1H), 8.373 (s, 1H), 8.311-8.327 (m, 1H), 8.169-8.196 (m, 1H), 8.052-8.078 (m, 1H), 7.969-7.996 (m, 1H), 7.594 (t, J=8.0 Hz, 1H), 7.050-7.083 (m, 1H), 6.198 (bro s, 1H), 4.798 (d, J=5.2 Hz, 2H), 2.511-2.564 (m, 1H), 1.259 (d, J=7.2 Hz, 1H); MS (m/e): 363.2 (M+1).

EXAMPLE 92

Compound 92: 3-((3-(imidazo[1,2-b]pyridazin-2-yl)benzylamino)methyl)benzonitrile was prepared in a manner similar to that described in Example 2.

$^1$H NMR (CD3OD, 400 MHz): δ 8.566 (s, 1H), 8.445 (d, J=2.4Hz, 1H), 7.946~8.425 (m, 3H), 7.225~7.839 (m, 5H), 6.105~6.132( t, 1H), 5.600( m, 1H), 4.090(s, 2H), 4.079(s, 2H); MS (m/e): 340 (M+1).

EXAMPLE 93

Compound 93: N-(3-(imidazo[1,2-b]pyridazin-2-yl)benzyl)-4-chlorobenzamide was prepared in a manner similar to that described in Example 2.

$^1$H NMR (CD30D, 400 MHz): δ 8.535 (s, 1H), 8.430~8.415 (q, J1=4.6 Hz, J2=1.6 Hz, 1H), 7.980~7.960 (t, J=6.0 Hz, 2H), 7.888(d, J=8.4 Hz, 2H), 7.494~7.428 (m, 4H), 7.393 (d, J=7.2 Hz, 1H), 7.248 (m, 1H), 4.658 (s, 2H); MS (m/e): 363 (M+1).

EXAMPLE 94

Compound 94: N-(3-(imidazo[1,2-b]pyridazin-2-yl)benzyl)-2-methoxyacetamide was prepared in a manner similar to that described in Example 2.

$^1$H NMR (CD30D, 400 MHz): δ 8.510 (s, 1H), 8.413 (s, 1H), 7.986~7.866 (m, 3H), 7.413(m, 3H), 4.503 (s, 2H), 3.971( s, 2H), 3.429 (s, 3H); MS (m/e): 297 (M+1).

EXAMPLE 95

Compound 95: N-(3-(imidazo[1,2-b]pyridazin-2-yl)benzyl)-3-cyanobenzenesulfonamide was prepared in a manner similar to that described in Example 2.

$^1$H NMR (CD30D, 400 MHz): δ 8.4580 (s, 1H), 8.456 (s, 1H), 7.982~8.012 (m, 3H), 7.700~7.715(m, 3H), 7.534~7.563 (t, 1H ), 7.215~7.309(m,3H ), 4.257 (s, 2H); MS (m/e): 390 (M+1).

EXAMPLE 96

Compound 96: 1-(3-(imidazo[1,2-b]pyridazin-2-yl)benzyl)-3-(thiophen-2-ylmethyl)urea was prepared in a manner similar to that described in Example 2.

$^1$H NMR (CD30D, 400 MHz): δ 8.497 (s, 1H), 8.432 (d, J=3.2Hz, 1H), 7.998 (d, J=9.2 Hz, 1H), 7.886 (s, 1H), 7.975 (d, J=7.6 Hz, 2H ), 7.417 (t, 1H), 7.319 (d, J=7.6 Hz, 1H), 7.249(m, 2H), 6.960 (s, 1H ), 6.925 (t, J=5.2 Hz, 1H), 4.523 (s, 2H ), 4.423 (s, 2H); MS (m/e): 364 (M+1).

EXAMPLE 97

Compound 97: 3-bromo-N-((3-(2-methylimidazo[2,1-b]thiazol-6-yl)phenyl)methyl)benzamide was prepared in a manner similar to that described in Example 2.

$^1$H NMR (CD$_3$OD, 400 MHz): δ 7.949 (s, 1H), 7.819 (s, 1H), 7.640 (m, 4H), 7.359 (t, J=10.0 Hz, 1H), 7.265 (m, 2H ), 7.128 (s,1H), 4.645 (d, J=7.6 Hz, 2H), 2.414 (s,3H); MS (m/e): 427 (M+1).

EXAMPLE 98

Compound 98: 4-chloro-N-((3-(2-methylimidazo[2,1-b]thiazol-6-yl)phenyl)methyl)benzamide was prepared in a manner similar to that described in Example 2.

¹H NMR (CD₃OD, 400 MHz): δ 7.835 (s, 1H), 7.726 (m, 3H), 7.640 (s, 1H), 7.388 (m, 3H), 7.270 (bs, 1H ), 7.143 (d, J=1.6 Hz, 1H ), 4.670(d, J=6.4 Hz, 2H), 2.430 (s, 3H); MS (m/e): 383 (M+1).

EXAMPLE 99

Compound 99: N-((3-(2-methylimidazo[2,1-b]thiazol-6-yl)phenyl)methyl)butyramide was prepared in a manner similar to that described in Example 2.

¹H NMR (CD₃OD, 400 MHz): δ 7.738 (s, 1H), 7.670 (d, J=7.8 Hz, 1H), 7.616 (s, 1H), 7.337 (t, J=7.8 Hz, 1H), 7.180 (d, J=8.0 Hz, 1H), 7.133 (s, 1H), 4.464(d, J=6.4 Hz, 2H), 2.419 (s,3H), 2.192(t, J=8.0 Hz, 2H), 1.689(m, 2H), 0.951(t, J=7.8 Hz, 2H); MS (m/e): 314 (M+1).

EXAMPLE 100

Compound 100: N-((3-(2-methylimidazo[2,1-b]thiazol-6-yl)phenyl)methyl)cyclopropanecarboxamide was prepared in a manner similar to that described in Example 2.

¹H NMR (CD₃OD, 400 MHz): δ 7.773 (s, 1H), 7.684 (d, J=8.0 Hz, 1H), 7.634 (s, 1H), 7.353(t, J=8.0 Hz, 1H), 7.207 (d, J=8.0 Hz, 1H), 7.142( s, 1H), 4.492(d, J=6.4 Hz, 2H), 2.427 (s, 3H), 1.355(m, 1H), 1.013(m, 2H), 0.755(m, 2H); MS (m/e): 312 (M+1).

EXAMPLE 101

Compound 101: N-((3-(3-(2-methylimidazo[2,1-b]thiazol-6-yl)phenyl)-1,2,4-oxadiazol-5-yl)methyl)(4-(methylsulfonyl)phenyl)methanamine was prepared in a manner similar to that described in Example 4.

¹H NMR (CDCl₃, 400 MHZ): δ 8.447 (s, 1H), 7.943-7.995 (m, 2H), 7.896 (d, J=8.4 Hz, 2H), 7.711 (s, 1H), 7.851 (d, J=8.4 Hz, 2H), 7.486 (t, J=7.6-8.0 Hz, 1H), 7.153 (s, 1H), 4.123 (s, 2H), 4.017 (s, 2H), 3.017 (s, 3H), 2.418 (s, 3H); MS (m/e): 480 (M+1).

EXAMPLE 102

Compound 102: 2-methoxy-N-((3-(3-(2-methylimidazo[2,1-b]thiazol-6-yl)phenyl)-1,2,4-oxadiazol-5-yl)methyl)ethanamine was prepared in a manner similar to that described in Example 4.

¹H NMR (CDCl₃, 400 MHZ): δ 8.444 (s, 1H), 7.730 (s, 1H), 7.954-8.019 (m, 2H), 7.715 (s, 1H), 7.477 (t, J=7.6-8.0 Hz, 1H), 7.137(s, 1H), 4.158(s, 2H), 3.540 (t, J=5.2, 2H), 3.364 (s,3H), 2.972 (t, J=4.8, 2H), 2.413 (s, 3H); MS (m/e): 370 (M+1).

EXAMPLE 103

Compound 103: N-((3-(H-imidazo[1,2-a]pyridin-2-yl)phenyl)methyl)-2-methoxyacetamide was prepared in a manner similar to that described in Example 2.

¹H NMR (CDCl₃, 300 MHz): δ 8.118 (d, J=6.6 Hz, 1H), 7.806~7.902 (m, 3H), 7.681 (d, J=9.3 Hz, 1H), 7.387 (t, J=15.3-7.5 Hz, 1H), 7.253 (s, 1H), 7.183 (t, J=15.6-7.8 Hz, 1H), 6.785 (t, J=13.8-5.7 Hz, 1H), 4.544 (d, J=5.7Hz, 2H), 3.953 (s, 2H), 3.390 (s, 3H); MS (m/e): 296.3 (M+1).

EXAMPLE 104

Compound 104: ethyl 2-((3-(H-imidazo[1,2-a]pyridin-2-yl)phenyl)methylamino)nicotinate was prepared in a manner similar to that described in Example 2.

¹H NMR (CDCl₃, 400 MHz): δ 8.303 (m, 1H), 8.292 (m, 1H), 8.154~8.092(m, 2H), 7.960 (s, 1H), 7.846 (s, 1H), 7.637 (d, J=10 Hz, 1H), 7.390~7.355 (m, 2H), 7.156 (m, 1H), 6.562 (m, 1H), 4.819 (d, J=5.2 Hz, 2H) , 4.326 (m, 2H), 1.351 (t, J=14.4-6.8 Hz, 3H); MS (m/e): 373.4 (M+1).

EXAMPLE 105

Compound 105: 1-((3-(H-imidazo[1,2-a]pyridin-2-yl)phenyl)methyl)-3-(2-chloro-4-fluorophenyl)urea was prepared in a manner similar to that described in Example 2.

¹H NMR (CDCl₃, 400 MHz): δ 8.273 (d, J=9.2Hz, 1H), 8.078 (d, J=6.8 Hz, 1H), 7.923~7.795 (m, 3H), 7.655 (d, J=8.4 Hz, 1H), 7.448~7.169 (m, 5H), 6.796 (t, J=13.6-6.4 Hz, 1H), 4.706 (s, 2H); MS (m/e): 395.8 (M+1).

EXAMPLE 106

Compound 106: 1-((3-(H-imidazo[1,2-a]pyridin-2-yl)phenyl)methyl)-3-(4-chloro-3-(trifluoromethyl)phenyl)urea was prepared in a manner similar to that described in Example 2.

¹H NMR (d-DMSO, 400 MHz): δ 9.496 (s, 1H), 8.544 (d, J=10.4 Hz, 1H),8.401 (s, 1H), 8.114 (s, 1H), 7.968 (s, 1H), 7.560-7.194 (m, 6H), 6.892 (t, 1H), 4.373 (d, 2H); MS (m/e): 445.8 (M+1).

EXAMPLE 107

In Vivo Assays

Balb/c mice (female, body weight 18 g-20 g) were used. Test compound suspension in 0.25% Tween 80 and 1% carboxymethylcellulose (CMC) was administered orally or parenterally, the negative control group being administered with the vehicle alone and the positive control group being administered with Prednisone (10 mg/kg). Half an hour later, all mice were injected intraperitoneally with lipopolysaccharide (LPS) (15 mg/kg, 10 mL/kg). Two hours after LPS injection, mice were bled for serum. Concentrations of TNF-α and IL-1β in the serum, stored at −20° C. overnight, were determined by ELISA. Tested compounds from this invention demonstrated significant inhibition of TNFα and IL-1β production at a dose ranging from 1 to 1000 mg/kg.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to compounds of Formula I can be made and screened for their inhibitory activities against the production of a cytokine (e.g., TNFα or interleukine) and treating cytokine-overproduction related disorders and used to practice this invention. Thus, other embodiments are also within the claims.

What is claimed is:

1. A compound of the formula:

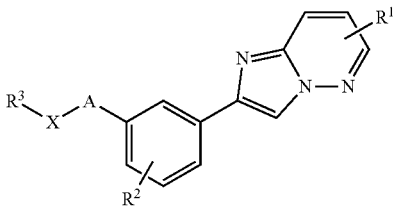

and/or at least one pharmaceutically acceptable salt thereof wherein

A is bond, (CR'R")$_n$ in which n is 1, 2, 3, 4, or 5, or a heteroaryl selected from

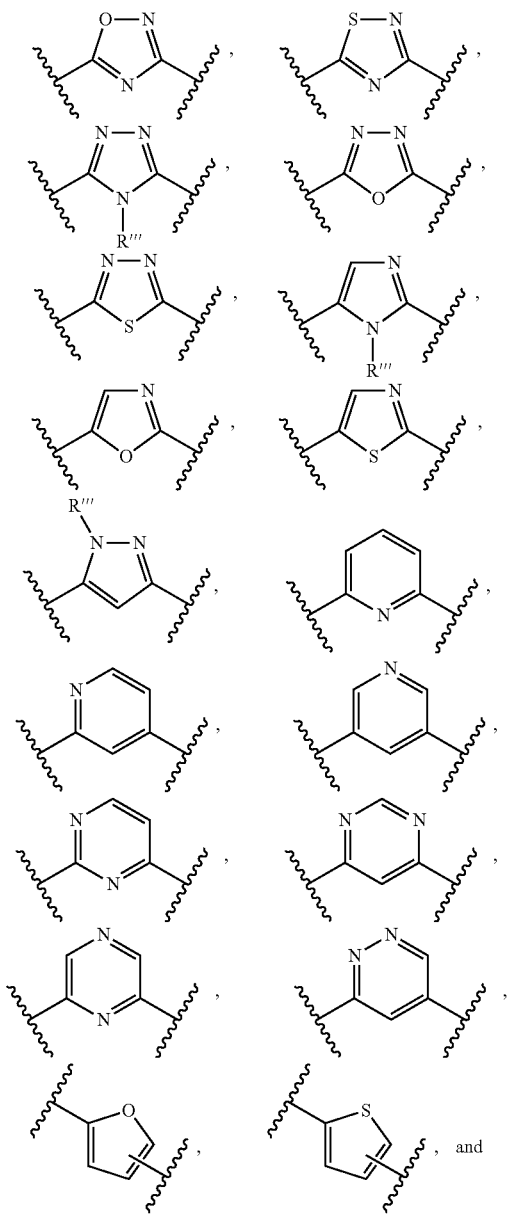

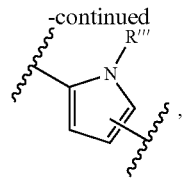

in which each of R' and R", independently, is H or $C_{1-10}$ alkyl, and R'" is H or $C_{1-10}$ alkyl, in which $C_{1-10}$ alkyl is optionally substituted by one or more groups chosen from halo, C(O)R$^a$, OR$^b$, SR$^b$, S(O)$_2$R$^b$, NR$^c$R$^d$, and C(O)NR$^c$NR$^d$, in which each of R$^a$ and R$^b$, independently, is H, $C_{1-10}$ alkyl, $C_{1-10}$ haloalkyl, aryl, or heteroaryl, and each of R$^c$ and R$^d$, independently, is H, $C_{1-10}$ alkyl, $C_{1-10}$ haloalkyl, aryl, or heteroaryl, or R$^c$ and R$^d$ together with the N atom to which they are attached form a 4-, 5-, 6- or 7-membered heterocycloalkyl group;

X is bond, (CR$^{a'}$R$^{b'}$)$_m$ in which m is 1, 2, 3, 4, or 5, SO, SO$_2$, CO, COO, CONR$^{c'}$, NR$^{c'}$, or NR$^{c'}$CNR$^{d'}$, in which each of R$^{a'}$, R$^{b'}$, R$^{c'}$, and R$^{d'}$, independently, is H or $C_{1-10}$ alkyl;

each of R$^1$ and R$^2$, independently, is H, NR$^{c1}$C(O)R$^{a1}$, OR$^{b1}$, NR$^{c1}$R$^{d1}$, NR$^{c1}$C(O)OR$^{b1}$, NR$^{c1}$S(O)$_2$R$^{b1}$, $C_{1-10}$ alkyl, or $C_{1-10}$ haloalkyl, in which each of R$^{a1}$ and R$^{b1}$, independently, is H, $C_{1-10}$ alkyl optionally substituted with $C_{1-6}$ alkoxy, $C_{1-10}$ haloalkyl, aryl, or heteroaryl, and each of R$^{c1}$ and R$^{d1}$, independently, is H, $C_{1-10}$ alkyl, $C_{1-10}$ haloalkyl, aryl, or heteroaryl, or R$^{c1}$ and R$^{d1}$ together with the N atom to which they are attached form a 4-, 5-, 6- or 7-membered heterocycloalkyl group; and R$^3$ is H, halo, OC(O)R$^{a2}$, C(O)OR$^{b2}$, OR$^{b2}$, SR$^{b2}$, SO$_2$R$^{b2}$, C(O)NR$^{c2}$R$^{d2}$, NR$^{c2}$R$^{d2}$, NR$^{c2}$C(O)R$^{a2}$, NR$^{c2}$C(O)C(O)OR$^{a2}$, NR$^{c2}$S(O)$_2$R$^{b2}$, $C_{1-10}$ alkyl, $C_{1-10}$ haloalkyl, aryl, haloaryl, cycloalkyl, heteroaryl, heterocycloalkyl, arylalkyl, heteroarylalkyl, cycloalkylalkyl or heterocycloalkylalkyl, in which $C_{1-10}$ alkyl, $C_{1-10}$ haloalkyl, aryl, haloaryl, cycloalkyl, heteroaryl, heterocycloalkyl, arylalkyl, heteroarylalkyl, cycloalkylalkyl or heterocycloalkylalkyl is optionally substituted by one or more groups chosen from halo, $C_{1-4}$ alkyl, $C_{1-4}$ haloalkyl, aryl, heteroaryl, CN, NO$_2$, OR$^{b2}$, C(O)OR$^{b2}$, C(O)NR$^{c2}$R$^{d2}$, and NR$^{c2}$R$^{d2}$, in which each of R$^{a2}$ and R$^{b2}$, independently, is H, $C_{1-6}$ alkyl, $C_{1-6}$ haloalkyl, aryl, cycloalkyl, heteroaryl, heterocycloalkyl, arylalkyl, or heteroarylalkyl in which $C_{1-6}$ alkyl, $C_{1-6}$ haloalkyl, aryl, cycloalkyl, heteroaryl, heterocycloalkyl, arylalkyl, or heteroarylalkyl is optionally substituted by one or more groups chosen from OH, $C_{1-6}$ alkoxyl, CN, NO$_2$, and halo, and each of R$^{c2}$ and R$^{d2}$, independently, is H, $C_{1-10}$ alkyl, $C_{1-10}$ haloalkyl, aryl, heteroaryl, cycloalkyl, heterocycloalkyl, arylalkyl, heteroarylalkyl, cycloalkylalkyl or heterocycloalkylalkyl, in which $C_{1-10}$ alkyl, $C_{1-10}$ haloalkyl, aryl, heteroaryl, cycloalkyl, heterocycloalkyl, arylalkyl, heteroarylalkyl, cycloalkylalkyl or heterocycloalkylalkyl is optionally substituted by one or more groups chosen from $C_{1-6}$ alkoxyl, OH, amino, $C_{1-4}$ alkylamino, $C_{2-8}$ dialkylamino, S(O)$_2$R$^{b2}$, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl, or R$^{c2}$ and R$^{d2}$ together with the N atom to which they are attached form a 4-, 5-, 6- or 7-membered heterocycloalkyl group.

2. The compound of claim 1, wherein A is absent, CH$_2$, or

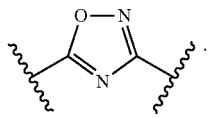

3. The compound of claim 1, wherein X is bond, (CR$^{a'}$R$^{b'}$)$_m$, CO, COO, NR$^{c'}$, CONR$^{c'}$, or NR$^{c'}$CONR$^{d'}$.

4. The compound of claim 3, wherein X is CH$_2$, NH, CO, COO, CONH, or NHCONH.

5. The compound of claim 2, wherein X is bond, (CR$^{a'}$R$^{b'}$)$_m$, CO, COO, NR$^{c'}$, CONR$^{c'}$, or NR$^{c'}$CONR$^{d'}$.

6. The compound of claim 5, wherein X is CH$_2$, NH, CO, COO, CONH, or NHCONH.

7. A compound chosen from
2-(3-(5-methyl-1,2,4-oxadiazol-3-yl)phenyl)imidazo[1,2-b]pyridazine;
1-(3-(imidazo[1,2-b]pyridazin-2-yl)benzyl)-3-(2-morpholinoethyl)urea;
1-(3-(imidazo[1,2-b]pyridazin-2-yl)benzyl)-3-(2-methoxyethy)urea;
N-((3-(3-(imidazo[1,2-b]pyridazin-2-yl)phenyl)-1,2,4-oxadiazol-5-yl)methyl)-2-methoxyethanamine;
N-((3-(3-(imidazo[1,2-b]pyridazin-2-yl)phenyl)-1,2,4-oxadiazol-5-yl)methyl)-2-morpholinoethanamine;
2-(3-(5-(morpholinomethyl)-1,2,4-oxadiazol-3-yl)phenyl)imidazo[1,2-b]pyridazine;
(3-(3-(imidazo[1,2-b]pyridazin-2-yl)phenyl)-1,2,4-oxadiazol-5-yl)-N,N-dimethylmethanamine;
2-((3-(3-(imidazo[1,2-b]pyridazin-2-yl)phenyl)-1,2,4-oxadiazol-5-yl) methylamino)ethanol;
N-((3-(3-(imidazo[1,2-b]pyridazin-2-yl)phenyl)-1,2,4-oxadiazol-5-yl) methyl)ethanamine;
2-(3-(5-((4-fluorophenoxy)methyl)-1,2,4-oxadiazol-3-yl)phenyl)imidazo[1,2-b]pyridazine;
2-(3-(5-(ethoxymethyl)-1,2,4-oxadiazol-3-yl)phenyl)imidazo[1,2-b]pyridazine;
2-(3-(5-(methoxymethyl)-1,2,4-oxadiazol-3-yl)phenyl)imidazo[1,2-b]pyridazine;
2-(3-(5-(trifluoromethyl)-1,2,4-oxadiazol-3-yl)phenyl)imidazo[1,2-b]pyridazine;
(3-(3-(imidazo[1,2-b]pyridazin-2-yl)phenyl)-1,2,4-oxadiazol-5-yl)methyl acetate;
2-(3-(5-isopropyl-1,2,4-oxadiazol-3-yl)phenyl)imidazo[1,2-b]pyridazine;
(3-(3-(imidazo[1,2-b]pyridazin-2-yl)phenyl)-1,2,4-oxadiazol-5-yl)methanol;
2-(3-(5-cyclopropyl-1,2,4-oxadiazol-3-yl)phenyl)imidazo[1,2-b]pyridazine;
2-(3-(5-(fluoromethyl)-1,2,4-oxadiazol-3-yl)phenyl)imidazo[1,2-b]pyridazine;
2-(3-(5-ethyl-1,2,4-oxadiazol-3-yl)phenyl)imidazo[1,2-b]pyridazine;
N-methyl-2-(3-(5-(trifluoromethyl)-1,2,4-oxadiazol-3-yl)phenyl)imidazo[1,2-b]pyridazin-6-amine;
ethyl 3-(3-(imidazo[1,2-b]pyridazin-2-yl)phenyl)-1,2,4-oxadiazole-5-carboxylate;
ethyl 2-(3-(3-(imidazo[1,2-b]pyridazin-2-yl)phenyl)-1,2,4-oxadiazol-5-yl)acetate;
3-(3-(imidazo[1,2-b]pyridazin-2-yOphenyl)-1,2,4-oxadiazole-5-carboxylic acid;
3-(3-(imidazo[1,2-b]pyridazin-2-yOphenyl)-1,2,4-oxadiazole-5-carboxamide;
2-(3-(3-(imidazo[1,2-b]pyridazin-2-yl)phenyl)-1,2,4-oxadiazol-5-yl)acetic acid;
2-(3-(5-(methylthiomethyl)-1,2,4-oxadiazol-3-yl)phenyl)imidazo[1,2-b]pyridazine;
2-(3-(5-(methylsulfonylmethyl)-1,2,4-oxadiazol-3-yl)phenyl)imidazo[1,2-b]pyridazine;
(3-(imidazo[1,2-b]pyridazin-2-yl)-5-(2-methoxyethoxy)phenyl)methanamine;
2-(3-(2-methoxyethoxy)-5-(5-(trifluoromethyl)-1,2,4-oxadiazol-3-yl)phenyl)imidazo[1,2-b]pyridazine;
2-(3-(2-methoxyethoxy)-5-(5-methyl-1,2,4-oxadiazol-3-yl)phenyl)imidazo[1,2-b]pyridazine;
2-(3-(5-(fluoromethyl)-1,2,4-oxadiazol-3-yl)-5-(2-methoxyethoxy)phenyl)imidazo[1,2-b]pyridazine;
2-(3-(2-methmethoxy)-5-(5-(methoxymethyl)-1,2,4-oxadiazol-3-yl)phenyl)imidazo[1,2-b]pyridazine;
2-(3-(5-(ethoxymethyl)-1,2,4-oxadiazol-3-yl)-5-(2-methoxyethoxy)phenyl)imidazo[1,2-b]pyridazine;
(3-(3-(imidazo[1,2-b]pyridazin-2-yl)-5-(2-methoxyethoxy)phenyl)-1,2,4-oxadiazol-5-yl)methanol;
3-(3-(imidazo[1,2-b]pyridazin-2-yl)-5-(2-methoxyethoxy)phenyl)-1,2,4-oxadiazole-5-carboxylic acid;
3-(3-(imidazo[1,2-b]pyridazin-2-yl)-5-(2-methoxyethoxy)phenyl)-1,2,4-oxadiazole-5-carboxamide;
3-(3-(imidazo[1,2-b]pyridazin-2-yl)-5-(2-methoxyethoxy)phenyl)-N-(pyridin-2-yl)-1,2,4-oxadiazole-5-carboxamide;
3-(3-(imidazo[1,2-b]pyridazin-2-yl)-5-(2-methoxyethoxy)phenyl)-N-(2,2,2-trifluoroethyl)-1,2,4-oxadiazole-5-carboxamide;
N-(3-(imidazo[1,2-b]pyridazin-2-yl)-5-(2-methoxyethoxy)benzyl)acetamide;
N-(3-(imidazo[1,2-b]pyridazin-2-yl)-5-(2-methoxyethoxy)benzyl)-2,2,2-trifluoroacetamide;
N-(3-(imidazo[1,2-b]pyridazin-2-yl)-5-(2-methoxyethoxy)benzyl)-2-chloroacetamide;
N-(3-(imidazo[1,2-b]pyridazin-2-yl)-5-(2-methoxyethoxy)benzyl)-4-chlorobenzamide;
N-(3-(imidazo[1,2-b]pyridazin-2-yl)-5-(2-methoxyethoxy)benzyl)-3-nitrobenzenesulfonamide;
N-(3-(imidazo[1,2-b]pyridazin-2-yl)-5-(2-methoxyethoxy)benzyl)-4-cyanobenzamide;
N-(3-(imidazo[1,2-b]pyridazin-2-yl)-5-(2-methoxyethoxy)benzyl)-3-bromobenzamide;
N-(3-(imidazo[1,2-b]pyridazin-2-yl)-5-(2-methoxyethoxy)benzyl)-4-fluorobenzenesulfonamide;
N-(3-(imidazo[1,2-b]pyridazin-2-yl)-5-(2-methoxyethoxy)benzyl)-3-chlorobenzenesulfonamide;
N-(3-(imidazo[1,2-b]pyridazin-2-yl)-5-(2-methoxyethoxy)benzyl)-4-methylbenzenesulfonamide;
N-(3-(imidazo[1,2-b]pyridazin-2-yl)-5-(2-methoxyethoxy)benzyl)-2-fluorobenzenesulfonamide;
N-(2-(diethylamino)ethyl)-2-(3-(3-(imidazo[1,2-b]pyridazin-2-yl)phenyl)-1,2,4-oxadiazol-5-yl)acetamide;
N-butyl-2-(3-(3-(imidazo[1,2-b]pyridazin-2-yl)phenyl)-1,2,4-oxadiazol-5-yl)acetamide;
2-(3-(3-(imidazo[1,2-b]pyridazin-2-yl)phenyl)-1,2,4-oxadiazol-5-yl)-N-(2-tetrahydrofuran-2-yl)methyl)acetamide;
N-cyclopentyl-2-(3-(3-(imidazo[1,2-b]pyridazin-2-yl)phenyl)-1,2,4-oxadiazol-5-yl)acetamide;
2-(3-(3-(imidazo[1,2-b]pyridazin-2-yl)phenyl)-1,2,4-oxadiazol-5-yl)-N-(2-methoxyethyl)acetamide;
2-(3-(3-(imidazo[1,2-b]pyridazin-2-yl)phenyl)-1,2,4-oxadiazol-5-yl)-1-morpholinoethanone;
N-cyclopropyl-2-(3-(3-(imidazo[1,2-b]pyridazin-2-yl)phenyl)-1,2,4-oxadiazol-5-yl)acetamide;

3-(3-(imidazo[1,2-b]pyridazin-2-yl)phenyl)-N-(2-mor-
pholinoethyl)-1,2,4-oxadiazole-5-carboxamide;
N-ethyl-3-(3-(imidazo[1,2-b]pyridazin-2-yl)phenyl)-1,2,
4-oxadiazole-5-carboxamide;
N-cyclopentyl-3-(3-(imidazo[1,2-b]pyridazin-2-yl)phe-
nyl)-1,2,4-oxadiazole-5-carboxamide;
(3-(3-(imidazo[1,2-b]pyridazin-2-yl)phenyl)-1,2,4-oxa-
diazol-5-yl)(morpholino)methanone;
3-(3-(imidazo[1,2-b]pyridazin-2-yl)phenyl)-N-(2-meth-
oxyethyl)-1,2,4-oxadiazole-5-carboxamide;
N-(2-(dimethylamino)ethyl)-3-(3-(imidazo[1,2-b]py-
ridazin-2-yl)phenyl)-1,2,4-oxadiazole-5-carboxamide;
(4-ethylpiperazin-1-yl)(3-(3-(imidazo[1,2-b]pyridazin-2-
yl)phenyl)-1,2,4-oxadiazol-5-yl)methanone;
3-(3-(imidazo[1,2-b]pyridazin-2-yl)phenyl)-N-(thiophen-
2-ylmethyl)-1,2,4-oxadiazole-5-carboxamide;
N-(2-hydroxyethyl)-3-(3-(imidazo[1,2-b]pyridazin-2-yl)
phenyl)-1,2,4-oxadiazole-5-carboxamide;
3-(3-(imidazo[1,2-b]pyridazin-2-yl)phenyl)-N,N-dim-
ethyl-1,2,4-oxadiazole-5-carboxamide;
(3-(3-(imidazo[1,2-b]pyridazin-2-yl)phenyl)-1,2,4-oxa-
diazol-5-yl)(pyrrolidin-1-yl)methanone;
3-(3-(imidazo[1,2-b]pyridazin-2-yl)phenyl)-N-methyl-1,
2,4-oxadiazole-5-carboxamide;
2-(3-(imidazo[1,2-b]pyridazin-2-yl)phenylamino)nicoti-
namide;
(2-(3-(imidazo[1,2-b]pyridazin-2-yl)phenylamino)pyri-
din-3-yl)(pyrrolidin-1-yl)methanone;
N-(2-hydroxyethyl)-2-(3-(imidazo[1,2-b]pyridazin-2-yl)
phenylamino)nicotinamide;
ethyl 2-(3-(imidazo[1,2-b]pyridazin-2-yl)phenylamino)
nicotinate;
N-cyclopropyl-2-(3-(imidazo[1,2-b]pyridazin-2-yl)phe-
nylamino)nicotinamide;
(2-(3-(imidazo[1,2-b]pyridazin-2-yl)phenylamino)pyri-
din-3-yl)(morpholino)methanone;
N-(3-(imidazo[1,2-b]pyridazin-2-yl)-5-(5-(morpholi-
nomethyl)-1,2,4-oxadiazol-3-yl)phenyl)methane-
sulfonamide;
N-(3-(imidazo[1,2-b]pyridazin-2-yl)-5-(5-(piperidin-1-
ylmethyl)-1,2,4-oxadiazol-3-yl)phenyl)methane-
sulfonamide;
N-(3-(imidazo[1,2-b]pyridazin-2-yl)-5-(5-((2-methoxy-
ethylamino)methyl)-1,2,4-oxadiazol-3-yl)phenyl)
methanesulfonamide;
N-(3-(5-((2-(dimethylamino)ethylamino)methyl)-1,2,4-
oxadiazol-3-yl)-5-(imidazo[1,2-b]pyridazin-2-yl)phe-
nyl)methanesulfonamide;
N-(3-(imidazo[1,2-b]pyridazin-2-yl)-5-(5-(piperazin-1-
ylmethyl)-1,2,4-oxadiazol-3-yl)phenyl)methane-
sulfonamide;
N-(3-(5-(aminomethyl)-1,2,4-oxadiazol-3-yl)-5-(imidazo
[1,2-b]pyridazin-2-yl)phenyl)methanesulfonamide;
2-(3-(5-(piperazin-1-ylmethyl)-1,2,4-oxadiazol-3-yl)phe-
nyl)imidazol[1,2-b]pyridazine;
N1-((3-(3-(imidazo[1,2-b]pyridazin-2-yl)phenyl)-1,2,4-
oxadiazol-5-yl)methyl)ethane-1,2-diamine;
N1-((3-(3-(imidazo[1,2-b]pyridazin-2-yl)phenyl)-1,2,4-
oxadiazol-5-yl)methyl)-N2,N2-dimethylethane-1,2-di-
amine;
2-(3-(5-(morpholinomethyl)-1,2,4-oxadiazol-3-yl)phe-
nyl)imidazol[1,2-b]pyridazine;
2,2,2-trifluoro-N-((3-(3-(imidazo[1,2-b]pyridazin-2-yl)
phenyl)-1,2,4-oxadiazol-5-yl)methyl)acetamide;
ethyl 2-((3-(3-(imidazo[1,2-b]pyridazin-2-yl) phenyl)-1,
2,4-oxadiazol-5-yl)methyl-amino) -2-oxoacetate;

N-((3-(3-(imidazo[1,2-b]pyridazin-2-yl)-phenyl)-1,2,4-
oxadiazol-5-yl)methyl)-2-methoxyacetamide;
N-((3-(3-(imidazo[1,2-b]pyridazin-2-yl)-phenyl)-1,2,4-
oxadiazol-5-yl)methyl)cyclopentanecarboxamide;
ethyl 3-((3-(3-(imidazo[1,2-b]pyridazin-2-yl)phenyl)-1,2,
4-oxadiazol-5-yl)methyl-amino) -3-oxopropanoate;
N-((3-(3-(imidazo[1,2-b]pyridazin-2-yl)-phenyl)-1,2,4-
oxadiazol-5-yl)methyl)cyclopropanecarboxamide;
N-((3-(3-(imidazo[1,2-b]pyridazin-2-yl)phenyl)-1,2,4-
oxadiazol-5-yl)methyl)isobutyramide;
3-((3-(imidazo[1,2-b]pyridazin-2-yl)benzylamino)me-
thyl)benzonitrile;
N-(3-(imidazo[1,2-b]pyridazin-2-yl)benzyl)-4-chlo-
robenzamide;
N-(3-(imidazo[1,2-b]pyridazin-2-yl)benzyl)-2-methoxy-
acetamide;
N-(3-(imidazo[1,2-b]pyridazin-2-yl)benzyl)-3-cyanoben-
zenesulfonamide; and
1-(3-(imidazo[1,2-b]pyridazin-2-yl)benzyl)-3-(thiophen-
2-ylmethyl)urea; and/or at least one pharmaceutically
acceptable salt thereof.

8. A pharmaceutical composition comprising a pharma-
ceutically acceptable carrier and a compound of the formula:

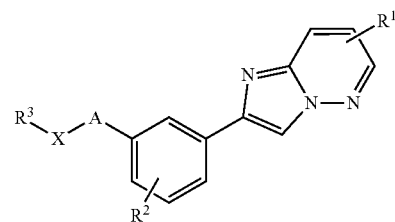

and/or at least one pharmaceutically acceptable salt thereof
wherein

A is bond, (CR'R")$_n$ in which n is 1, 2, 3, 4, or 5, or a
heteroaryl selected from

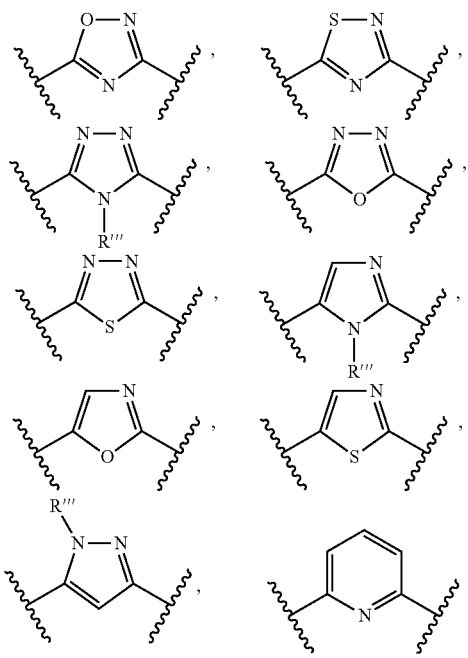

-continued

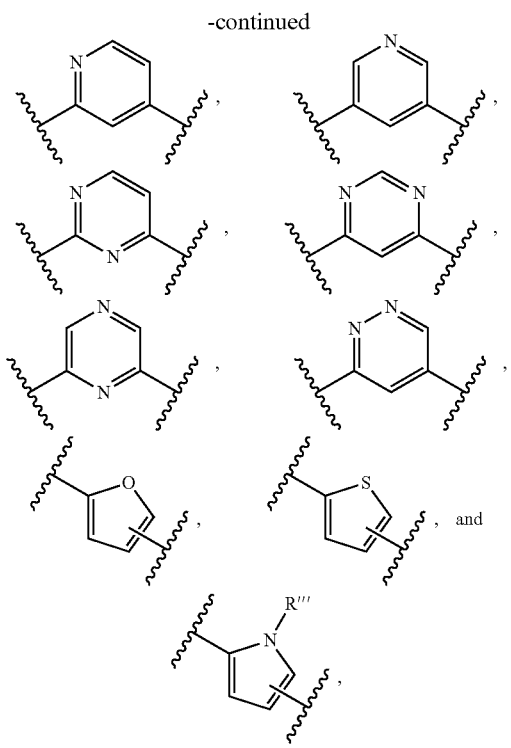

in which each of R' and R", independently, is H or $C_{1-10}$ alkyl, and R'" is H or $C_{1-10}$ alkyl, in which $C_{1-10}$ alkyl is optionally substituted by one or more groups chosen from halo, $C(O)R^a$, $OR^b$, $SR^b$, $S(O)_2R^b$, $NR_cR^d$, and $C(O)NR^cNR^d$, in which each of $R^a$ and $R^b$, independently, is H, $C_{1-10}$ alkyl, $C_{1-10}$ haloalkyl, aryl, or heteroaryl, and each of $R^c$ and $R^d$, independently, is H, $C_{1-10}$ alkyl, $C_{1-10}$ haloalkyl, aryl, or heteroaryl, or $R^c$ and $R^d$ together with the N atom to which they are attached form a 4-, 5-, 6- or 7-membered heterocycloalkyl group;

X is bond, $(CR^{a'}R^{b'})_m$ in which m is 1, 2, 3, 4, or 5, SO, $SO_2$, CO, COO, $CONR^{c',NRc'}$, or $NR^{c'}CONR^{d'}$, in which each of $R^{a'}$, $R^{b'}$, $R^{c'}$, and $R^{d'}$, independently, is H or $C_{1-10}$ alkyl;

each of $R^1$ and $R^2$, independently, is H, $NR^{c1}C(O)R^{a1}$, $OR^{b1}$, $NR^{c1}R^{d1}$, $NR^{c1}C(O)OR^{b1}$, $NR^{c1}S(O)_2R^{b1}$, $C_{1-10}$ alkyl or $C_{1-10}$ haloalkyl, in which each of $R^{a1}$ and $R^{b1}$, independently, is H, $C_{1-10}$ alkyl optionally substituted with $C_{1-6}$ alkoxyl, $C_{1-10}$ haloalkyl, aryl, or heteroaryl, and each of $R^{c1}$ and $R^{d1}$, independently, is H, $C_{1-10}$ alkyl, $C_{1-10}$ haloalkyl, aryl, or heteroaryl, or $R^{c1}$ and $R^{d1}$ together with the N atom to which they are attached form a 4-, 5-, 6- or 7-membered heterocycloalkyl group; and $R^3$ is H, halo, $OC(O)R^{a2}$, $C(O)OR^{b2}$, $OR^{b2}$, $SR^{b2}$, $SO_2R^{b2}$, $C(O)NR^{c2}R^{d2}$, $NR^{c2}R^{d2}$, $NR^{c2}C(O)R^{a2}$, $NR^{c2}C(O)C(O)OR^{a2}$, $NR^{c2}S(O)_2R^{b2}$, $C_{1-10}$ alkyl, $C_{1-10}$ haloalkyl, aryl, haloaryl, cycloalkyl, heteroaryl, heterocycloalkyl, arylalkyl, heteroarylalkyl, cycloalkylalkyl or heterocycloalkylalkyl, in which $C_{1-10}$ alkyl, $C_{1-10}$ haloalkyl, aryl, haloaryl, cycloalkyl, heteroaryl, heterocycloalkyl, arylalkyl, heteroarylalkyl, cycloalkylalkyl or heterocycloalkylalkyl is optionally substituted by one or more groups chosen from halo, $C_{1-4}$ alkyl, $C_{1-4}$ haloalkyl, aryl, heteroaryl, CN, $NO_2$, $OR^{b2}$, $C(O)OR^{b2}$, $C(O)NR^{c2}R^{d2}$, and $NR^{c2}R^{d2}$, in which each of $R^{a2}$ and $R^{b2}$, independently, is H, $C_{1-6}$ alkyl, $C_{1-6}$ haloalkyl, aryl, cycloalkyl, heteroaryl, heterocycloalkyl, arylalkyl, or heteroarylalkyl in which $C_{1-6}$ alkyl, $C_{1-6}$ haloalkyl, aryl, cycloalkyl, heteroaryl, heterocycloalkyl, arylalkyl, or heteroarylalkyl is optionally substituted by one or more groups chosen from OH, $C_{1-6}$ alkoxyl, CN, $NO_2$, and halo, and each of $R^{c2}$ and $R^{d2}$, independently, is H, $C_{1-10}$ alkyl, $C_{1-10}$ haloalkyl, aryl, heteroaryl, cycloalkyl, heterocycloalkyl, arylalkyl, heteroarylalkyl, cycloalkylalkyl or heterocycloalkylalkyl, in which $C_{1-10}$ alkyl, $C_{1-10}$ haloalkyl, aryl, heteroaryl, cycloalkyl, heterocycloalkyl, arylalkyl, heteroarylalkyl, cycloalkylalkyl or heterocycloalkylalkyl is optionally substituted by one or more groups chosen from $C_{1-6}$ alkoxyl, OH, amino, $C_{1-4}$ alkylamino, $C_{2-8}$ dialkylamino, $S(O)_2R^{b2}$, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl, or $R^{c2}$ and $R^{d2}$ together with the N atom to which they are attached form a 4-, 5-, 6- or 7-membered heterocycloalkyl group.

9. The pharmaceutical composition of claim 8, wherein A is bond, $CH_2$, or

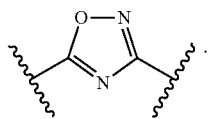

10. The pharmaceutical composition of claim 8, wherein X is bond, $(CR^{a'}R^{b'})_m$, CO, COO, $NR^{c'}$, $CONR^{c'}$, or $NR^{c'}CONR^{d'}$.

11. The pharmaceutical composition of claim 10, wherein X is $CH_2$, NH, CO, COO, CONH, or NHCONH.

12. The pharmaceutical composition of claim 9, wherein X is bond, $(CR^{a'}R^{b'})_m$, CO, COO, $NC^{c'}$, $CONR^{c'}$, or $NR^{c'}CONR^{d'}$.

13. The pharmaceutical composition of claim 12, wherein X is $CH_2$, NH, CO, COO, CONH, or NHCONH.

14. A pharmaceutical composition comprising a pharmaceutically acceptable carrier and the compound of claim 7, and/or at least one pharmaceutically acceptable salt thereof.

15. A compound that is 2-(3-(5-(piperazin-1-ylmethyl)-1,2,4-oxadiazol-3-yl)phenyl)imidazo[1,2-b]pyridazine, and/or at least one pharmaceutically acceptable salt thereof.

16. A pharmaceutical composition comprising a pharmaceutically acceptable carrier and 2-(3-(5-(piperazin-1-ylmethyl)-1,2,4-oxadiazol-3-yl)phenyl)imidazo[1,2-b]pyridazine, and/or at least one pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 7,868,001 B2 | |
| APPLICATION NO. | : 11/934154 | |
| DATED | : January 11, 2011 | |
| INVENTOR(S) | : Wei Deng et al. | |

It is certified that error appears in the above-identified patent and that said Letters Patent is hereby corrected as shown below:

On the Title Page, Item (57), in the Abstract, line 5, "interlukine" should read --interleukin--.

In claim 1, column 62, line 12, "R" is" should read --R'" is--.

In claim 1, column 62, line 22, "$NR^{c'}CNR^{d'}$," should read --$NR^{c'}CONR^{d'}$,--.

In claim 1, column 62, line 27, "$NR^{c1}S(O)_2R^{b1}$," should read --$NR^{c1}S(O)_2R^{b1}$,--.

In claim 2, column 63, line 1, "absent," should read --bond,--.

In claim 7, column 63, lines 23-24,
"1-(3-(imidazo[1,2-b]pyridazin-2-yl)benzyl)-3-(2-methoxyethy)urea;" should read
--1-(3-(imidazo[1,2-b]pyridazin-2-yl)benzyl)-3-(2-methoxyethyl)urea;--.

In claim 7, column 63, lines 64-65,
"3-(3-(imidazo[1,2-b]pyridazin-2-yOphenyl)-1,2,4-oxadiazole-5-carboxylic acid;" should read
--3-(3-(imidazo[1,2-b]pyridazin-2-yl)phenyl)-1,2,4-oxadiazole-5-carboxylic acid;--.

In claim 7, column 63, lines 66-67,
"3-(3-(imidazo[1,2-b]pyridazin-2-yOphenyl)-1,2,4-oxadiazole-5-carboxamide;" should read
--3-(3-(imidazo[1,2-b]pyridazin-2-yl)phenyl)-1,2,4-oxadiazole-5-carboxamide;--.

In claim 7, column 64, lines 15-16,
"2-(3-(2-methmethoxy)-5-(5-(methoxymethyl)-1,2,4-oxadiazol-3-yl)phenyl)imidazo[1,2-b]pyridazine;" should read
--2-(3-(2-methoxyethoxy)-5-(5-(methoxymethyl)-1,2,4-oxadiazol-3-yl)phenyl)imidazo[1,2-b]pyridazine;--.

Signed and Sealed this
Tenth Day of May, 2011

David J. Kappos
*Director of the United States Patent and Trademark Office*

CERTIFICATE OF CORRECTION (continued)
U.S. Pat. No. 7,868,001 B2

In claim 7, column 64, lines 57-59,
"2-(3-(3-(imidazo[1,2-b]pyridazin-2-yl)phenyl)-1,2,4-oxadiazol-5-yl)-N-(2-tetrahydrofuran-2-yl)methyl)acetamide;" should read
--2-(3-(3-(imidazo[1,2-b]pyridazin-2-yl)phenyl)-1,2,4-oxadiazol-5-yl)-N-(((S)-tetrahydrofuran-2-yl)methyl)acetamide;--.

In claim 7, column 66, lines 11-12,
"3-((3-(imidazo[1 ,2-b]pyridazin-2-yl)benzylamino)methyl)benzonitrile;" should read
--3-((3-(imidazo[1,2-b]pyridazin-2-yl)benzylamino)methyl)benzonitrile;--.

In claim 8, column 67, line 34, "$^{NRc}R^d$," should read --$NR^cR^d$,--.

In claim 8, column 67, line 41, "$(CR^{a'}R^{b')}{}_m$" should read --$(CR^{a'}R^{b'})_m$--.

In claim 8, column 67, line 42, "$CONR^{c',\ NRc'}$," should read --$CONR^{c'}, NR^{c'}$,--.

In claim 8, column 67, line 47, "$R^{bl}$," should read --$R^{b1}$,--.

In claim 12, column 68, line 43, "$(CR^{a'}R^{b'}{}_m$," should read --$(CR^{a'}R^{b'})_m$,--.